United States Patent
Jun et al.

(10) Patent No.: US 10,459,627 B2
(45) Date of Patent: Oct. 29, 2019

(54) MEDICAL IMAGE DISPLAY APPARATUS AND METHOD OF PROVIDING USER INTERFACE

(71) Applicant: Samsung Electronics Co., Ltd., Gyeonggi-do (KR)

(72) Inventors: Yoon-woo Jun, Seoul (KR); Ji-woo Kim, Seoul (KR); Jin-gyu Seo, Namyangju-si (KR); Min-Ju Lee, Seoul (KR); Seung-ju Lee, Ansan-si (KR); Jin-ho Yim, Suwon-si (KR)

(73) Assignee: Samsung Electronics Co., Ltd., Yeongtong-gu, Suwon-si, Gyeonggi-do (KR)

(*) Notice: Subject to any disclaimer, the term of this patent is extended or adjusted under 35 U.S.C. 154(b) by 74 days.

(21) Appl. No.: 15/906,138

(22) Filed: Feb. 27, 2018

(65) Prior Publication Data

US 2018/0188946 A1    Jul. 5, 2018

Related U.S. Application Data

(63) Continuation of application No. 14/956,508, filed on Dec. 2, 2015, now Pat. No. 9,946,841.

(30) Foreign Application Priority Data

May 26, 2015   (KR) ................... 10-2015-0073092

(51) Int. Cl.
*G06F 3/0488*    (2013.01)
*G16H 40/63*    (2018.01)
(Continued)

(52) U.S. Cl.
CPC .......... *G06F 3/04883* (2013.01); *A61B 8/462* (2013.01); *A61B 8/463* (2013.01);
(Continued)

(58) Field of Classification Search
CPC ............ G06F 3/04883; G06F 3/04847; G06F 3/04886; G06F 2200/1637; A61B 8/462;
(Continued)

(56) References Cited

U.S. PATENT DOCUMENTS 9,092,069 B2   7/2015   Ferren
2002/0087061 A1   7/2002   Lifshitz et al.
(Continued)

FOREIGN PATENT DOCUMENTS

EP   1 662 358 A1   5/2006
EP   2 602 702 A2   6/2013
(Continued)

OTHER PUBLICATIONS

European Search Report dated Apr. 20, 2018.
European Search Report dated Jan. 16, 2019.

*Primary Examiner* — Nitin Patel
*Assistant Examiner* — Amy Onyekaba
(74) *Attorney, Agent, or Firm* — Cha & Reiter, LLC

(57) ABSTRACT

A medical image display apparatus including a touch screen configured to display a medical image and receive input from a user; and a controller configured to acquire first information about a first region of the touch screen, the first region corresponding to a touch range of a finger of the user, to select, based on the first information, a first user interface from among a plurality of user interfaces related to the medical image, the first user interface corresponding to a size of the first region, and to control the touch screen to display the selected first user interface.

20 Claims, 74 Drawing Sheets

(51) Int. Cl.
   *A61B 8/00* (2006.01)
   *G06F 3/0484* (2013.01)
(52) U.S. Cl.
   CPC ............. *A61B 8/465* (2013.01); *A61B 8/54* (2013.01); *G06F 3/04847* (2013.01); *G06F 3/04886* (2013.01); *G16H 40/63* (2018.01); *G06F 2200/1637* (2013.01)
(58) Field of Classification Search
   CPC ........... A61B 8/54; A61B 8/463; A61B 8/465; G16H 40/63
   See application file for complete search history.

(56) References Cited

U.S. PATENT DOCUMENTS

| | | | |
|---|---|---|---|
| 2007/0256029 A1 | 11/2007 | Maxwell | |
| 2009/0043195 A1 | 2/2009 | Poland | |
| 2009/0109187 A1* | 4/2009 | Noma | G06F 3/04883 345/173 |
| 2010/0145195 A1* | 6/2010 | Hyun | A61B 8/00 600/437 |
| 2010/0179427 A1* | 7/2010 | Yamamoto | A61B 8/00 600/443 |
| 2013/0141366 A1* | 6/2013 | Ritter | G06F 3/041 345/173 |
| 2013/0203469 A1 | 8/2013 | Cho et al. | |
| 2013/0212529 A1 | 8/2013 | Amarnath | |
| 2013/0265235 A1 | 10/2013 | Cai et al. | |
| 2014/0164997 A1* | 6/2014 | Lee | G06F 3/04883 715/810 |
| 2014/0289642 A1* | 9/2014 | Prasad | G06F 3/048 715/745 |
| 2014/0303501 A1* | 10/2014 | Jin | A61B 8/4477 600/459 |
| 2014/0365803 A1 | 12/2014 | Pham et al. | |
| 2015/0025386 A1* | 1/2015 | Ninomiya | A61B 8/4427 600/443 |
| 2015/0054761 A1* | 2/2015 | Kim | G16H 40/63 345/173 |
| 2015/0297185 A1* | 10/2015 | Mander | A61B 8/463 600/443 |
| 2016/0120507 A1* | 5/2016 | Ninomiya | A61B 8/4405 345/1.3 |
| 2019/0142382 A1* | 5/2019 | Kann | A61B 8/463 |

FOREIGN PATENT DOCUMENTS

| | | |
|---|---|---|
| EP | 2 631 774 A1 | 8/2013 |
| EP | 2 752 744 A1 | 7/2014 |
| JP | 2008-515583 A | 5/2008 |
| KR | 10-2010-0065720 A | 6/2010 |
| KR | 10-2011-0018589 A | 2/2011 |
| KR | 10-2013-0093043 A | 8/2013 |
| KR | 10-1364881 B1 | 2/2014 |
| KR | 10-1432483 B1 | 8/2014 |

* cited by examiner

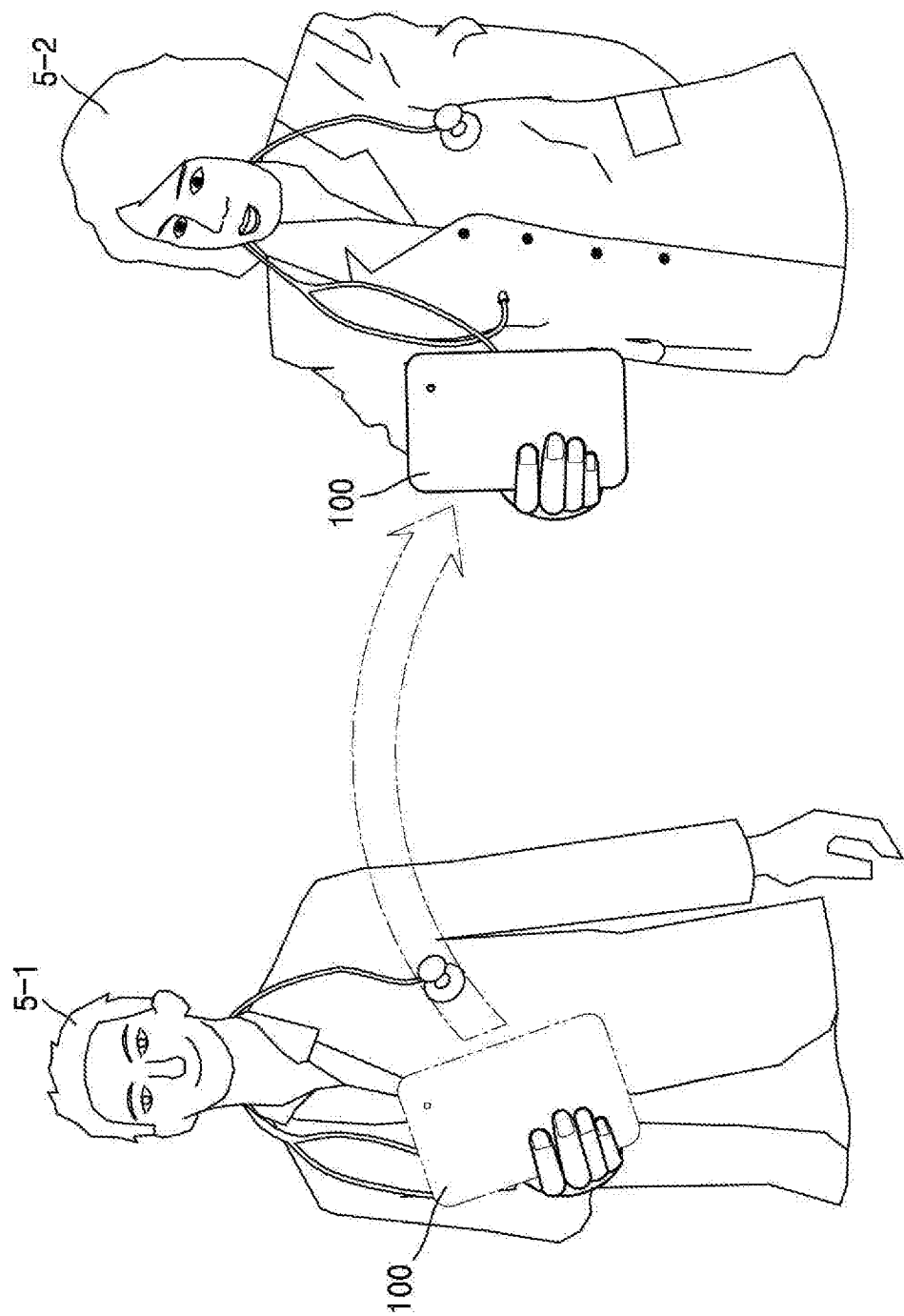

FIG. 42
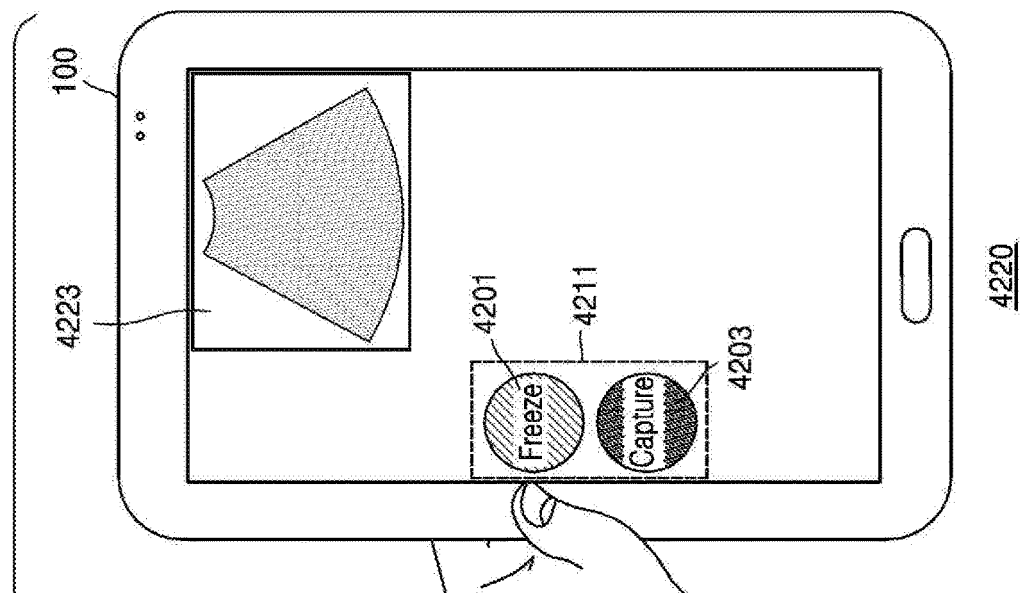
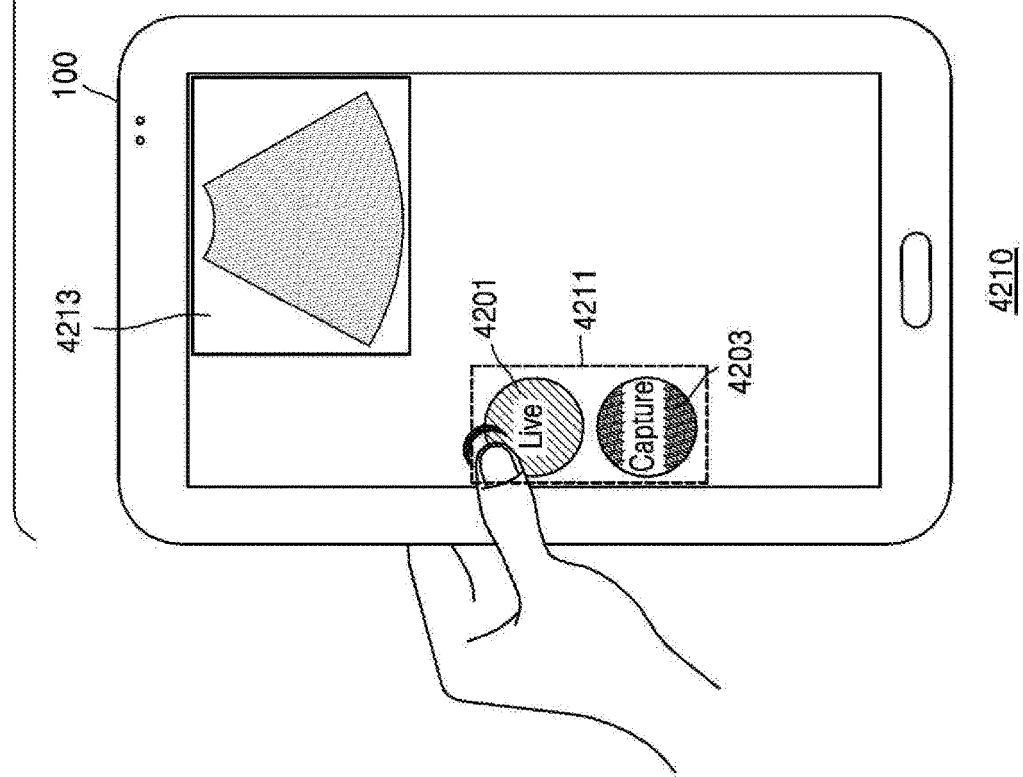

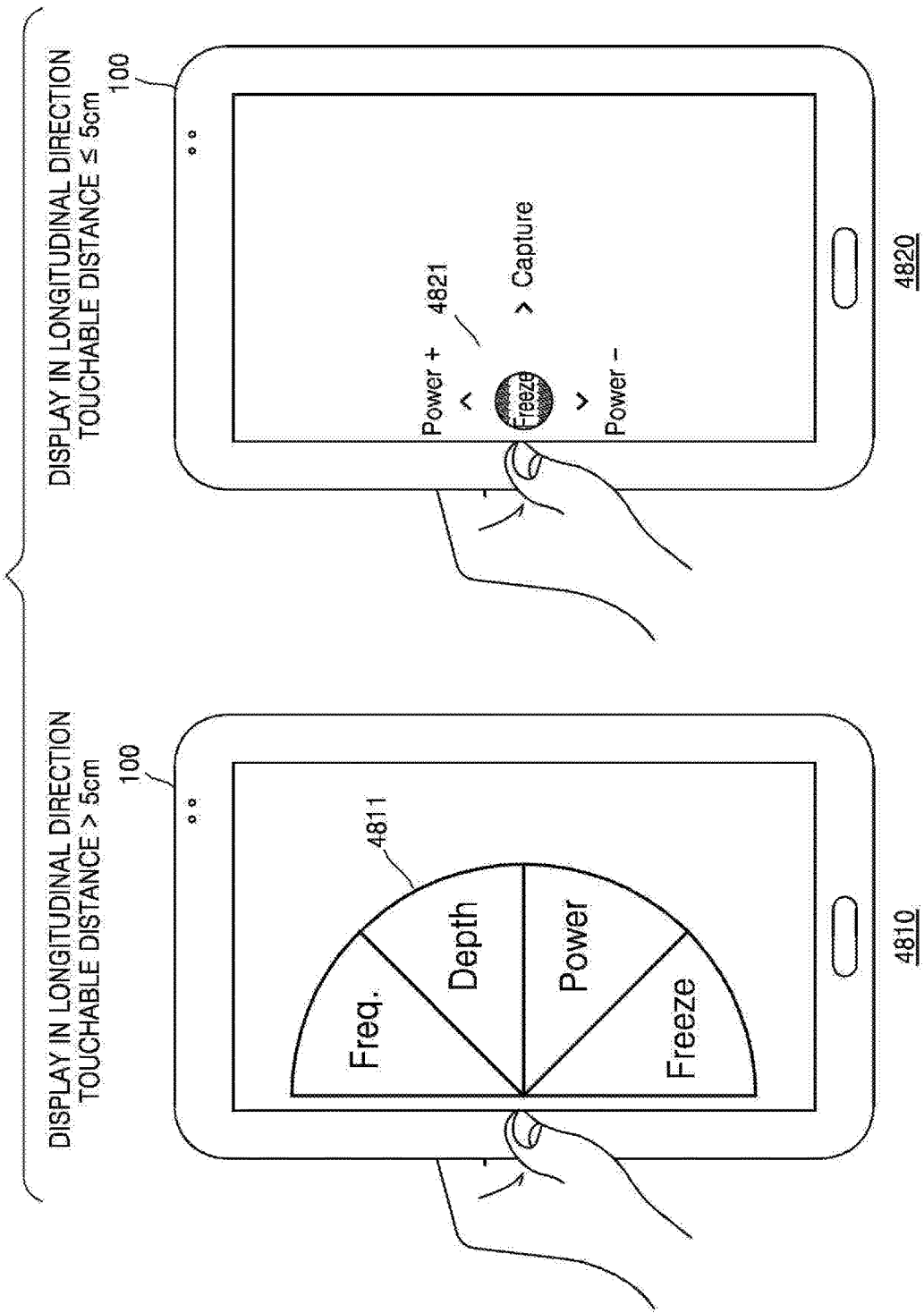

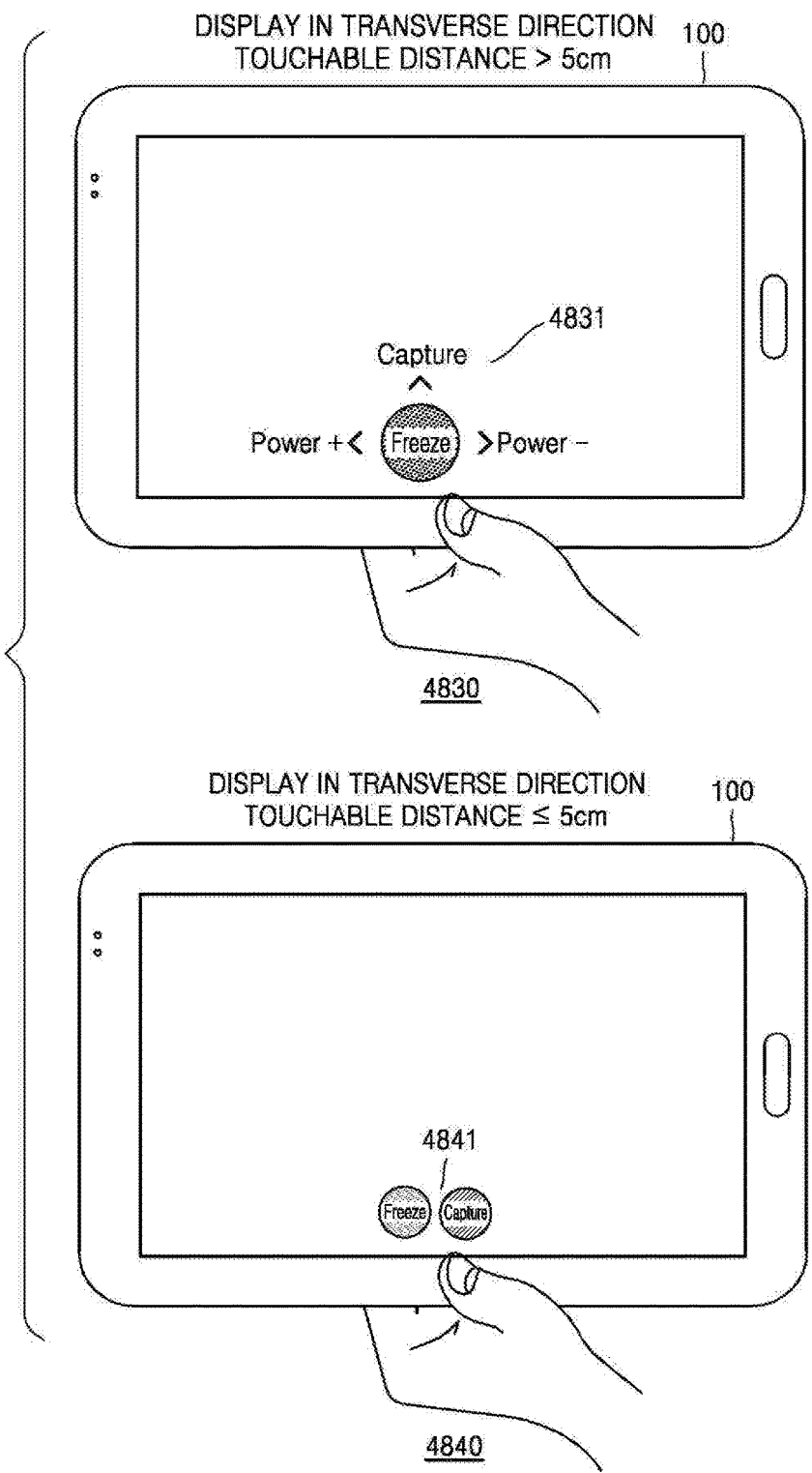

MEDICAL IMAGE DISPLAY APPARATUS AND METHOD OF PROVIDING USER INTERFACE

CROSS-REFERENCE TO RELATED APPLICATION

This application is a Continuation of U.S. patent application Ser. No. 14/956,508 filed on Dec. 2, 2015 which claims benefit from Korean Patent Application No. 10-2015-0073092, filed on May 26, 2015, in the Korean Intellectual Property Office, the disclosure of which is incorporated herein in its entirety by reference.

BACKGROUND

1. Field

The present disclosure relates to medical image display apparatuses and methods of providing a user interface via the medical image display apparatuses, and more particularly, to medical image display apparatuses and methods of providing a user interface suitable for a user.

2. Description of the Related Art

A medical imaging system acquires medical image data of an object, displays a medical image generated based on the acquired medical image data, and provides the medical image to a user. The medical imaging system may include a medical image acquisition apparatus and a medical image display apparatus.

The medical image acquisition apparatus emits a signal toward an object and acquires medical image data related to a cross-section of an object or blood flow by using a signal received from the object in response to the emitted signal.

For example, the medical image acquisition apparatus may acquire ultrasound image data, X-ray image data, computerized tomography (CT) image data, magnetic resonance (MR) image data, positron emission tomography (PET) image data, and the like.

The medical imaging system may generate a medical image from medical image data acquired by the medical image acquisition apparatus and display the generated medical image to the user on a screen of the medical image display apparatus.

A medical image may be used to diagnose or treat a disease in a patient. To use the medical image for diagnosis and treatment of a disease, it may be necessary to move a medical image display apparatus so as to provide a medical image close to a patient or user. However, since a medical image display apparatus is generally bulky and heavy, the medical image display apparatus has to be fixedly installed at a specific place and is difficult to carry. Thus, to solve this problem, a medical image display apparatus that can be carried by a user is being developed.

As medical image display apparatuses become lighter and smaller, the user may use one hand to grip and carry a medical image display apparatus. When the user handles the medical image display apparatus using one hand, the other hand is left free. Thus, the user may conveniently use the other hand to perform other activities related to diagnosis and treatment of a patient with a disease. Thus, it is necessary to develop a user interface that allows a user to hold and use a medical image display apparatus using one hand.

SUMMARY

Provided are methods and medical image display apparatuses for providing a user interface based on a size of a finger-touchable range such that the user interface is suitable for the user who uses one hand to hold and use the medical image display apparatus.

Additional aspects will be set forth in part in the description which follows and, in part, will be apparent from the description, or may be learned by practice of the presented exemplary embodiments.

According to an aspect of an exemplary embodiment, a medical image display apparatus includes a touch screen configured to display a medical image and receive input from a user; and a controller configured to acquire first information about a first region of the touch screen, the first region corresponding to a touch range of a finger of the user, to select, based on the first information, a first user interface from among a plurality of user interfaces related to the medical image, the first user interface corresponding to a size of the first region, and to control the touch screen to display the selected first user interface.

The controller may be configured to receive identification (ID) information corresponding to the user, and to acquire the first information by retrieving information about a finger-touchable range corresponding to the received ID information from a memory.

The touch screen may be configured to display a guide image and to receive a touch gesture from the finger, the touch gesture corresponding to the guide image, and the controller may be configured to acquire the first information by analyzing the received touch gesture.

The touch screen may be further configured to detect a swipe touch of the finger, and the controller may be further configured to obtain a swipe speed at which the detected swipe touch moves, and to acquire the first information by determining a distance on the touch screen between a reference point and a point at which the swipe speed corresponds to a threshold speed.

The controller may be further configured to acquire the first information by determining at least one from among a maximum finger-touchable distance, a maximum angle formed between a first line connecting a reference point to a first point and a second line connecting the reference point to a second point, the first point and the second point being touchable by the finger, and a maximum area of a finger-touchable region.

The controller may be further configured to select the first user interface from among the plurality of user interfaces based on a result of comparing the size of the first region to a threshold size.

The controller may be further configured to select at least one function from among a plurality of functions provided by the medical image display apparatus in relation to the medical image, the at least one function corresponding to the size of the first region, and to select the first user interface based on the selected at least one function.

The controller may be further configured to select a first type of touch gesture from among a plurality of types of touch gestures, the first type of touch gesture corresponding to the size of the first region, and to select the first user interface based on the selected first type of touch gesture.

The controller may be further configured to select the first user interface from among the plurality of user interfaces based on at least one from among a direction in which the medical image display apparatus displays content and a side of the medical image display apparatus at which a hand of the user is located.

The controller may be further configured to control the touch screen to display the first user interface including a plurality of icons corresponding to a plurality of parameters related to the medical image, and, in response to the touch screen receiving a touch gesture selecting a first icon from among the plurality of icons, to display in the first region a second user interface for adjusting a first parameter from among the plurality of parameters, the first parameter corresponding to the first icon.

The second user interface may include a plurality of sections corresponding to a plurality of values, the plurality of sections being displayed so that the plurality of values increase along a certain direction, and in response to the touch screen receiving a touch gesture performed by moving the finger from a first section from among the plurality of sections to a second section from among the plurality of sections, the controller may be further configured to change the first parameter from a first value corresponding to the first section to a second value corresponding to the second section.

The controller may be further configured to control the touch screen to display the first user interface including a first icon, and in response to the touch screen receiving a predetermined first touch gesture corresponding to the first icon, to control an ultrasound probe to transmit ultrasound signals to an object at predetermined time intervals and to receive echo signals from the object.

The controller may be further configured to control the touch screen to display the medical image in a second region of the touch screen, and in response to the touch screen receiving a predetermined second touch gesture corresponding to the first icon, the controller may be further configured to reduce the medical image into a reduced medical image, to control the touch screen to display the reduced medical image in a third region of the touch screen, and to control a memory to store the medical image.

The controller may be further configured to: control the touch screen to display the first user interface including a first icon, in response to the touch screen receiving a predetermined first touch gesture corresponding to the first icon, select a first parameter from among a plurality of parameters related to the medical image, and in response to the touch screen receiving a predetermined second touch gesture corresponding to the first icon, change the selected parameter based on a direction of the predetermined second touch gesture.

The touch screen may be further configured to display the selected first user interface at a position determined based on a position of at least one from among a hand or the finger of the user.

The touch screen may be further configured to change a first position at which the medical image is displayed based on a second position at which the selected first user interface is displayed, the first position and the second position being determined so that the selected first user interface and the medical image do not overlap each other.

The controller may be further configured to acquire information about a contact area of the finger of the user, and to select the first user interface based on the contact area, wherein the first user interface includes at least one icon having an icon size corresponding to the contact area.

The controller may be further configured to acquire the first information, to select the first user interface, and to display the first user interface in response to determining that the medical image display apparatus is detached from a medical image acquisition apparatus configured to acquire medical image data from an object.

The medical image display apparatus may further include sensors configured to detect motion information of the medical image display apparatus, wherein the controller may be further configured to acquire the first information, to select the first user interface, and to display the first user interface in response to determining that the medical image display apparatus is moving based on the detected motion information.

According to another aspect of an exemplary embodiment, a method of providing a user interface on a touch screen in a medical image display apparatus for displaying a medical image, includes acquiring first information about a first region of the touch screen, the first region corresponding to a touch range of a finger of a user; selecting a first user interface from among a plurality of user interfaces related to the medical image, the first user interface corresponding to a size of the first region and displaying the selected first user interface on the touch screen.

The acquiring of the first information about the first region may include: receiving identification (ID) information corresponding to the user; and acquiring the first information by retrieving from a memory information about a finger-touchable range corresponding to the received ID information.

The acquiring of the first information about the first region may include: displaying a guide image; receiving a touch gesture corresponding to the guide image from the finger, and acquiring the first information by analyzing the received touch gesture.

The acquiring of the first information about the first region may include: detecting a swipe touch of the finger, and acquiring the first information by determining a distance on the touch screen between a reference point and a point where a speed at which the swipe touch moves corresponds to a threshold speed.

The acquiring of the first information about the first region may include determining at least one from among a maximum finger-touchable distance, a maximum angle formed between a first line connecting a reference point to a first point and a second line connecting the reference point to a second point, the first point and the second point being touchable by the finger, and a maximum area of a finger-touchable region.

The selecting of the first user interface may include selecting the first user interface from among the plurality of user interfaces based on a result of comparing the size of the first region to a threshold size.

The selecting of the first user interface may include: selecting at least one function from among a plurality of functions provided by the medical image display apparatus in relation to the medical image, the at least one function corresponding to the size of the first region; and selecting the first interface based on the at least one function.

The selecting of the first user interface may include: selecting a first type of touch gesture from among a plurality of types of touch gestures, the first type of touch gesture corresponding to the size of the first region; and selecting the first user interface based on the first type of touch gesture.

The selecting of the first user interface may include selecting the first user interface from among the plurality of user interfaces based on at least one from among a direction in which the medical image display apparatus displays content and a side of the medical image display apparatus at which a hand of the user is located.

The displaying of the selected first user interface may include: displaying the first user interface including a plurality of icons corresponding to a plurality of parameters related to the medical image; and when a touch gesture selecting a first icon from among the plurality of icons is received, displaying in the first region a second user interface for adjusting a first parameter from among the plurality of parameters, the first parameter corresponding to the first icon.

The second user interface may include a plurality of sections corresponding to a plurality of values, the plurality of sections being displayed so that the plurality of values increase along a certain direction, and the method may further include, in response to the touch screen receiving a touch gesture performed by moving the finger from a first section from among the plurality of sections to a second section from among the plurality of sections, changing the first parameter from a first value corresponding to the first section to a second value corresponding to the second section.

The method may further include, in response to the touch screen receiving a predetermined first touch gesture with corresponding to a first icon, controlling an ultrasound probe to transmit ultrasound signals to an object at predetermined time intervals and receive echo signals from the object.

The method may further include: displaying the medical image in a second region of the touch screen; in response to the touch screen receiving a predetermined second touch gesture with corresponding to the first icon, reducing the medical image into a reduced medical image and displaying the reduced medical image in a third region of the touch screen; and storing the medical image in the memory.

The method may further include in response to the touch screen receiving a predetermined first touch gesture corresponding to a first icon included in the first user interface, selecting a first parameter from among a plurality of parameters related to the medical image; and in response to the touch screen receiving a predetermined second touch gesture corresponding to the first icon changing the selected parameter based on a direction of the predetermined second touch gesture.

The displaying of the first user interface may include displaying the first user interface at a position determined based on at least one from among a position of a hand or the finger of the user.

The method may further include changing a first position at which the medical image is displayed based on a second position at which the first user interface is displayed, the first position and the second position being determined so that the first user interface and the medical image do not overlap each other.

The first user interface may include at least one icon having a size corresponding to a contact area of the finger of the user.

The acquiring of the first information about the first region may include acquiring the first information about the first region when the medical image display apparatus is detached from a medical image acquisition apparatus configured to acquire medical image data from an object.

The method may further include detecting motion information of the medical image display apparatus; and determining, based on the detected motion information, that the medical image display apparatus is moving, wherein the acquiring of the first information about the first region may include acquiring the first information about the first region in response to the determining.

According to another aspect of an exemplary embodiment, non-transitory computer-readable recording medium may have recorded thereon a program for performing the methods above.

BRIEF DESCRIPTION OF THE DRAWINGS

These and other aspects will become apparent and more readily appreciated from the following description of the exemplary embodiments, taken in conjunction with the accompanying drawings in which:

FIG. 12A and FIG. 12B are diagrams for explaining a method of acquiring information about a first region when a user holding a medical image display apparatus is changed, according to an exemplary embodiment;

FIG. 42 and FIG. 43 illustrate an example of a UI provided by a medical image display apparatus, according to an exemplary embodiment;

FIG. 48A and FIG. 48B illustrate examples of UIs provided based on a direction in which a medical image display apparatus displays content and a size of a first region, according to an exemplary embodiment;

DETAILED DESCRIPTION

Figure 1:
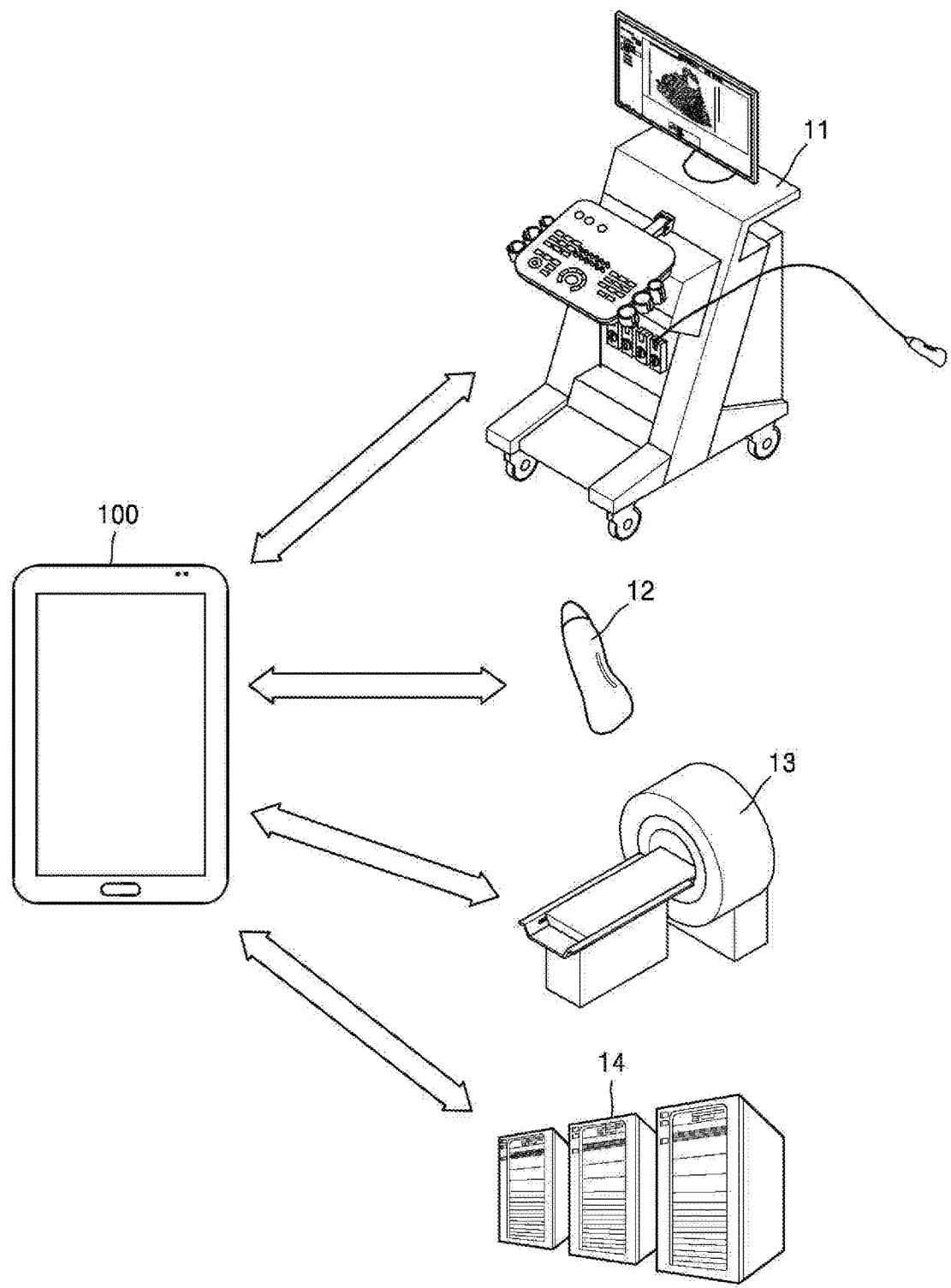
FIG. 1 illustrates a medical image display apparatus which receives medical image data from various devices, according to various exemplary embodiments.

The terms used in this specification are those general terms currently widely used in the art, but the terms may vary according to the intention of those of ordinary skill in the art, precedents, or new technology in the art. Also, some terms may be arbitrarily selected by the applicant, and in this case, the meaning of the selected terms will be described in detail in the detailed description of the present specification. Thus, the terms used herein have to be defined based on the meaning of the terms together with the description throughout the specification.

Throughout the specification, it will also be understood that when a component "includes" an element, unless there is another opposite description thereto, it should be understood that the component does not exclude another element and may further include another element. In addition, terms such as " . . . unit", " . . . module", or the like refer to units that perform at least one function or operation, and the units may be implemented as hardware or software or as a combination of hardware and software.

Throughout the specification, it will be understood that when an element is referred to as being "connected" or "coupled" to another element, it can be directly connected or coupled to the other element, or electrically connected or coupled thereto with one or more intervening elements interposed therebetween. When a part "includes" or "comprises" an element, unless there is a particular description contrary thereto, the part can further include other elements, not excluding the other elements.

In the present specification, an "object" may be a human, an animal, or a portion of a human or animal. For example, the object may include an organ (e.g., the liver, heart, womb, brain, breast, or abdomen), a cell, a tissue, or a blood vessel. Also, the object may include a phantom. The phantom means a material having a density and an effective atomic number that are approximately the same as those of an organism.

In the present specification, a "user" may be, but is not limited to, a medical expert, such as a medical doctor, a nurse, a medical laboratory technologist, a medical image expert, a radiologist, a sonographer, or a technician who repairs a medical apparatus. For example, the "user" may be an ordinary person who uses a medical image display apparatus or a patient being examined.

Throughout the specification, a "medical image" may include any image used for diagnosis and treatment of a disease and which represents a cross-section and volume data of an object based on a signal projected onto the object. For example, the "medical image" may include an ultrasound image, a Magnetic Resonance (MR) image, a Computed Tomography (CT) image, or a Positron Emission Tomography (PET) image. Furthermore, the "medical image" may include any of a two-dimensional (2D) image of a cross-section of an object, a three-dimensional image representing an object in 3D space, a moving image, and a stereoscopic image giving a viewer a sense of depth.

Reference will now be made in detail to exemplary embodiments, examples of which are illustrated in the accompanying drawings wherein like reference numerals may generally refer to like elements throughout. In this regard, the present exemplary embodiments may have different forms and should not be construed as being limited to the descriptions set forth herein. Furthermore, parts not related to the present disclosure are omitted to clarify the description of exemplary embodiments. As used herein, the term "and/or" includes any and all combinations of one or more of the associated listed items. Expressions such as "at least one of," when preceding a list of elements, modify the entire list of elements and do not modify the individual elements of the list.

FIG. 1 illustrates a medical image display apparatus 100 which receives medical image data from various devices 11 through 14, according to an exemplary embodiment.

According to various exemplary embodiments, the medical image display apparatus 100 may receive medical image data stored therein or in the various devices 11 through 14 and display a medical image generated using the received medical image data. For example, the medical image display apparatus 100 may display an ultrasound image, an X-ray image, a CT mage, an MR image, a PET image, or the like. A medical image displayed via the medical image display apparatus 100 may be used to diagnose or treat a disease in a patient.

The medical image display apparatus may be a handheld, portable apparatus. In some exemplary embodiments, the medical image display apparatus may be temporarily attached to another device or fixedly installed at a certain position. The medical image display apparatus 100 may be a device manufactured only to diagnose and treat a disease, but is not limited thereto. Examples of the medical image display apparatus 100 may include various types of devices for displaying an image, such as a smart phone, a laptop computer, a personal digital assistant (PDA), a tablet PC, an electronic book (e-book) terminal, a digital broadcasting terminal, a portable multimedia player (PMP), a navigation device, a smart TV, consumer electronics (CE), etc.

According to various exemplary embodiments, the medical image display apparatus 100 may be connected, by wire or wirelessly, to the various devices 11 through 14 for providing medical image data related to an object. The various devices 11 through 14 include an ultrasound diagnosis device 11, an ultrasound probe 12, a medical image acquisition device 13 configured to acquire medical image data other than ultrasound image data, and a server 14.

The medical image display apparatus 100 may receive medical image data from the various devices 11 through 14. The medical image display apparatus 100 may display a medical image generated using the received medical image data. The medical image display apparatus 100 may display various pieces of information processed by the various devices 11 through 14, as well as the medical image, via a graphical user interface (GUI). The various pieces of information processed by the medical image display apparatus 100 may include information related to functions and parameters used for the medical image display apparatus 100 to display a medical image and information necessary for controlling the various devices 11 through 14.

The medical image display apparatus 100 may transmit a control signal to the various devices 11 through 14. The ultrasound diagnosis device 11, the ultrasound probe 12, or the medical image acquisition device 13 may emit a signal toward an object in response to the control signal received from the medical image display apparatus 100 and acquire medical image data related to a cross-section of an object or blood flow by using a signal received from the object in response to the emitted signal. The server 14 may acquire medical image data regarding an object from a medical image acquisition apparatus, a memory, or another server according to the control signal received from the medical image display apparatus 100.

For example, as shown in FIG. 1, the medical image display apparatus 100 may be connected to the ultrasound diagnosis device 11 by wire or wirelessly.

The ultrasound diagnosis device 11 may be a device that transmits ultrasound signals generated by transducers of an ultrasound probe from a surface of an object to a part inside a body and acquires ultrasound image data related to a cross-section of soft tissue or blood flow based on echo signals reflected from an internal tissue.

The medical image display apparatus 100 may be included in the ultrasound diagnosis device 11 and may be attached to or detached from the ultrasound diagnosis device 11. In some exemplary embodiments, the medical image display apparatus 100 may be a separate device that is connected to the ultrasound diagnosis device 11 by wire or wirelessly and receives ultrasound image data from the ultrasound diagnosis device 11.

The medical image display apparatus 100 may display an ultrasound image by using the ultrasound image data received from the ultrasound diagnosis device 11. The medical image display apparatus 100 may also provide a GUI for controlling the medical image display apparatus 100 or for setting a function related to an operation of displaying an ultrasound image by the medical image display apparatus 100. Furthermore, the medical image display apparatus 100 may provide a GUI for controlling the ultrasound diagnosis device 11 or for setting a function related to an operation of acquiring ultrasound image data by the ultrasound diagnosis device 11.

As another example, the medical image display apparatus 100 may be connected to the ultrasound probe 12 by wire or wirelessly.

The ultrasound probe 12 may transmit an ultrasound signal to an object according to a driving signal applied by the medical image display apparatus 100 and receive an echo signal reflected by the object. The ultrasound probe 12 may include a plurality of transducers that oscillate in response to transmitted electrical signals and generate acoustic energy in the form of ultrasound waves. The ultrasound probe 12 may acquire ultrasound image data associated with a cross-section of soft tissue or blood flow based on the received echo signal.

The medical image display apparatus 100 may be connected to a plurality of ultrasound probes 12 according to its implemented configuration. The ultrasound probe 12 according to an exemplary embodiment may include at least one of a 1-dimensional (1D) probe, a 1.5-dimensional (1.5D) probe, and a two-dimensional (2D) (matrix) probe.

The medical image display apparatus 100 may display an ultrasound image by using ultrasound image data received from the ultrasound probe 12. The medical image display apparatus 100 may also provide a GUI for controlling the medical image display apparatus 100 or for setting a function related to an operation of displaying an ultrasound image by the medical image display apparatus 100. Furthermore, the medical image display apparatus 100 may provide a GUI for controlling the ultrasound probe 12 or for setting a function related to an operation of acquiring ultrasound image data by the ultrasound probe 12.

As another example, the medical image display apparatus 100 may be connected, by wire or wirelessly, to the medical image acquisition device 13 for acquiring medical image data other than ultrasound image data. The medical image acquisition device 13 may include, but is not limited to, an MRI image acquisition device, a CT image acquisition device, an X-ray image acquisition device, an angiography apparatus, etc. For example, the medical imaging acquisition device 13 may include in-vitro diagnostic (IVD) medical devices.

An X-ray acquisition device may be configured to image an internal structure of a human body by passing an X-ray through the human body.

A CT image acquisition device may provide medical image data regarding a cross-section of an object by passing an X-ray through the human body. Furthermore, the CT image acquisition device may acquire CT image data that represents an internal structure (e.g., an organ such as a kidney, a lung, etc.) of the object without superimposition of adjacent structures, as compared to a general X-ray apparatus. The CT image acquisition device may provide a relatively accurate cross-sectional image of an object by acquiring several tens to several hundreds of images having a thickness not more than 2 mm per second and processing the images.

An MRI image acquisition device may be a device for acquiring medical image data related to a cross-section of an object by expressing, in a contrast comparison, a strength of a MR signal with respect to a radio frequency (RF) signal generated in a magnetic field having a specific strength.

An angiography apparatus may be used to acquire medical image data related to blood vessels (an artery, a vein, etc.) of an examinee, into which a contrast medium is injected through a catheter (a tube of less than 2 mm in diameter).

According to exemplary embodiments, the medical image display apparatus 100 may be located outside a shielded room or connected to the medical image acquisition device 13 inside the shielded room.

The medical image display apparatus 100 may display a medical image by using medical image data received from the medical image acquisition device 13. The medical image display apparatus 100 may also provide a GUI for controlling the medical image display apparatus 100 or for setting a function related to an operation of displaying an ultrasound image by the medical image display apparatus 100. Furthermore, the medical image display apparatus 100 may provide a GUI for controlling the medical image acquisition device 13 or for setting a function related to an operation of acquiring medical image data by the medical image acquisition device 13.

As another example, the medical image display apparatus 100 may be connected to the server 14 by wire or wirelessly. For example, the medical image display apparatus 100 may transmit and receive data to and from a hospital server connected through a picture archiving and communication system (PACS), and perform data communication with the server 14 according to the digital imaging and communications in medicine (DICOM) standard.

The server 14 may be a server for managing medical image data. For example, the server 14 may store or update medical image data and medical records associated with each patient. The server 14 may transmit medical image data to the medical image display apparatus 100. In some exemplary embodiments, the server 14 may authenticate the medical image display apparatus 100 that attempts to access the medical image data and provide the medical image data only to the authenticated medical image display apparatus 100.

The medical image display apparatus 100 may display a medical image by using medical image data received from the server 14. The medical image display apparatus 100 may also provide a GUI for controlling the medical image display apparatus 100 or for setting a function related to an operation of displaying an ultrasound image by the medical image display apparatus 100. Furthermore, the medical image display apparatus 100 may provide a GUI for controlling the server 14 or for setting functions related to operations of acquiring, storing, and managing medical image data by the server 14.

The medical image display apparatus 100 may include an input device which may be configured to receive a user input for controlling the medical image display apparatus 100 and various devices connected to the medical image display apparatus 100. For example, the medical image display apparatus 100 may include various input devices such as a plurality of function keys, a trackball, buttons and a keyboard. However, if the various input devices are disposed on an outer surface of the medical image display apparatus 100, the medical image display apparatus 100 may become bulky.

Thus, to increase utilization of a limited space in the medical image display apparatus 100, a touch pad for performing functions of various input devices may be disposed on the outer surface of the medical image display apparatus 100 instead of the various input devices being all disposed thereon.

In particular, if the medical image display apparatus 100 includes a touch screen in which a display unit for displaying a medical image forms a layer structure with a touch pad, the medical image display apparatus 100 may become smaller and lighter in weight because the touch screen may serve as both input and output devices.

Figure 2:
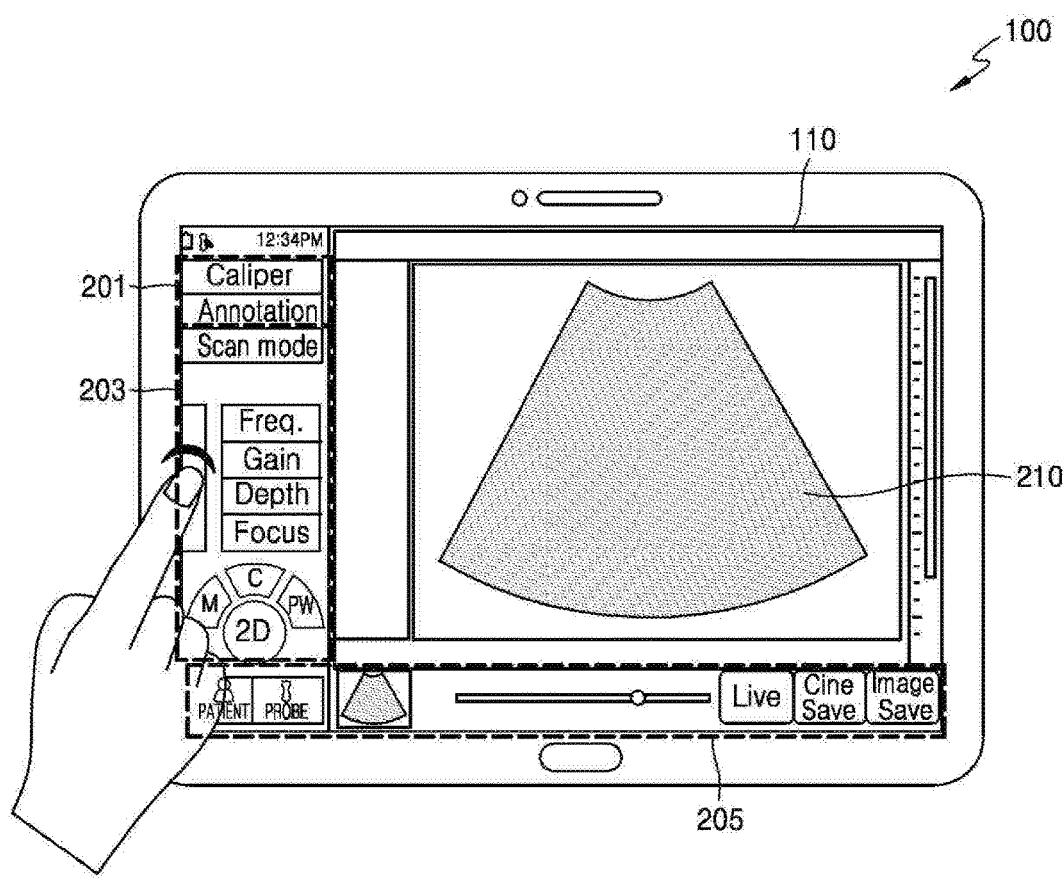
FIG. 2 shows an example of a touch screen provided in the medical image display apparatus 100 according to an exemplary embodiment.

As shown in FIG. 2, according to various exemplary embodiments, the medical image display apparatus 100 may include a touch screen 110.

FIG. 2 shows an example of a touch screen provided in the medical image display apparatus 100, according to an exemplary embodiment. Although FIG. 2 shows an example where the medical image display apparatus 100 displays an ultrasound image and a UI related to the ultrasound image on the touch screen 110, exemplary embodiments are not limited thereto. According to various exemplary embodiments, the medical image display apparatus 100 may provide various types of medical images and UIs related thereto.

According to various exemplary embodiments, the medical image display apparatus 100 may display via the touch screen 110 a medical image 210 and various pieces of information being processed by the medical image display apparatus 100. For example, the medical image display apparatus 100 may display a GUI 201 for displaying information about the medical image 210 currently being displayed, a GUI 203 for setting parameters related to the medical image 210, and a GUI 205 for controlling a medical image acquisition apparatus, an external device, or a server connected to the medical image display apparatus 100.

The information about the medical image 210 may include any desired information, for example a position of a region of an object depicted in the medical image 210, a position or a size of a lesion, a position or a size of a region of interest (ROI) designated by a user, information about a text or a body marker stored together with the medical image 210, or any other desired information or combination thereof.

The parameters related to the medical image 210 may include at least one piece of information among pieces of information relating to numerical values that are set with respect to acquiring the medical image 210 displayed via the medical image display apparatus 100, numerical values that are set with respect to displaying the acquired medical image 210, and numerical values related to an object depicted in the medical image 210. The parameters related to the medical image 210 may include parameters for setting a brightness, a zoom ratio, and a color of the medical image 210 and a parameter related to correction of the medical image 210. For example, the GUI 203 may include a GUI for changing parameters related to a frequency at which an ultrasound signal is transmitted, a gain, a depth, a focus, or any other desired parameter, in order to acquire the medical image or a GUI for changing a scan mode.

A GUI for controlling a medical image acquisition apparatus, an external device, or a server connected to the medical image display apparatus 100 may include a GUI for setting a method of acquiring medical image data or a method of managing the medical image data. For example, the GUI 205 may include a GUI for setting an operating mode in which a probe connected to the medical image display apparatus 100 operates or a GUI for controlling a memory to store medical image data.

Figure 3:
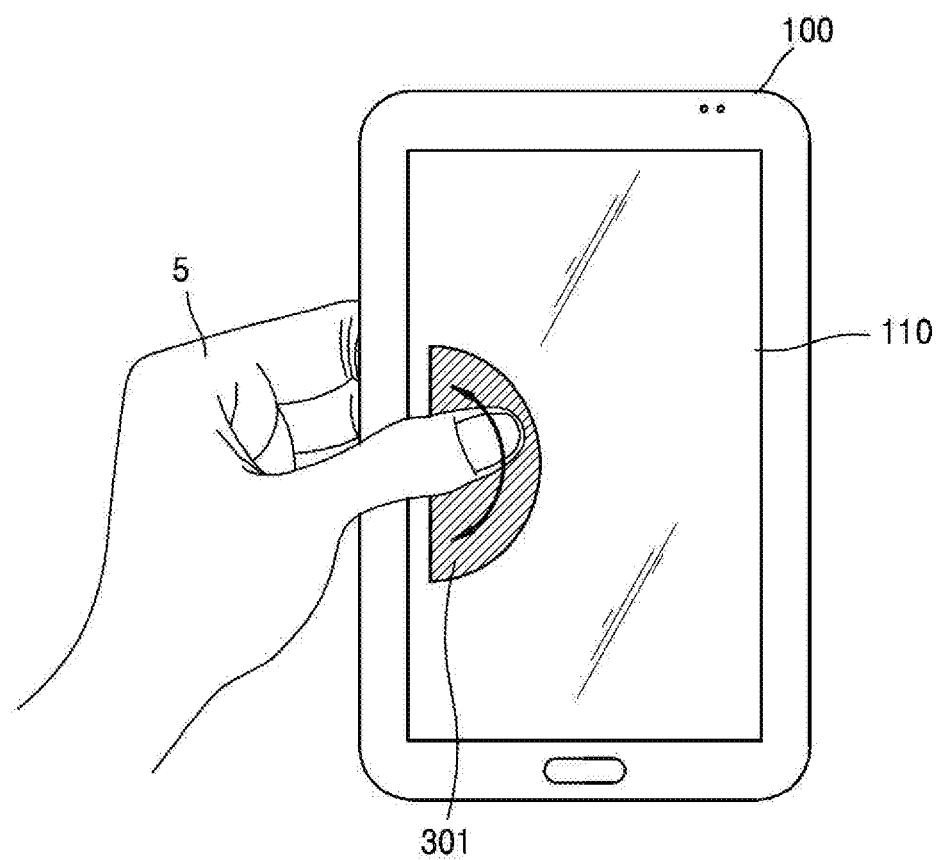
FIG. 3 is a diagram for explaining a finger-touchable range when the user grips a medical image display apparatus with one hand.

As the medical image display apparatus 100 becomes lighter and smaller, the user may use one hand to grip and carry the medical image display apparatus 100. As shown in FIG. 3, a user 5 may use the medical image display apparatus 100 by touching a touch screen 110 with one hand. When the user 5 uses the medical image display apparatus 100 with one hand, the user 5 may conveniently use the other hand to perform other activities related to diagnosis and treatment of a patient with a disease.

For example, if the medical image display apparatus 100 is connected to an ultrasound diagnosis device, the user 5 may grip an ultrasound probe of the ultrasound diagnosis device with one hand and the medical image display apparatus 100 with the other hand. The user 5 may move the ultrasound probe to a position corresponding to an area of interest in a patient so that the ultrasound probe may acquire ultrasound image data of the area of interest. Simultaneously, in order to be provided with an optimized ultrasound image, the user 5 may control operations of the ultrasound diagnosis device and the medical image display apparatus 100 related to acquisition and display of an ultrasound image by using the medical image display apparatus 100. Thus, the medical image display apparatus 100 may provide the user 5 with an optimized ultrasound image of a desired area in real-time.

In some exemplary embodiments, while the user grips the medical image display apparatus 100 with one hand, a region that may be touched or covered by a finger of the user 5 may be limited. For example, as shown in FIG. 3, a region that may be accessible to a finger of the user 5 may be limited to a region 301, marked with diagonal lines. Thus, according to exemplary embodiments, a method and a medical image display apparatus for providing a UI based on a touch range of a finger of the user 5 may be provided.

According to various exemplary embodiments, the medical image display apparatus 100 may provide a UI based on a touch range of a finger of the user 5. For example, referring to FIG. 4, a medical image display apparatus 100 according to an exemplary embodiment may display a UI 401 within a region 301 that may be touched by a finger of a user 5.

Figure 4:
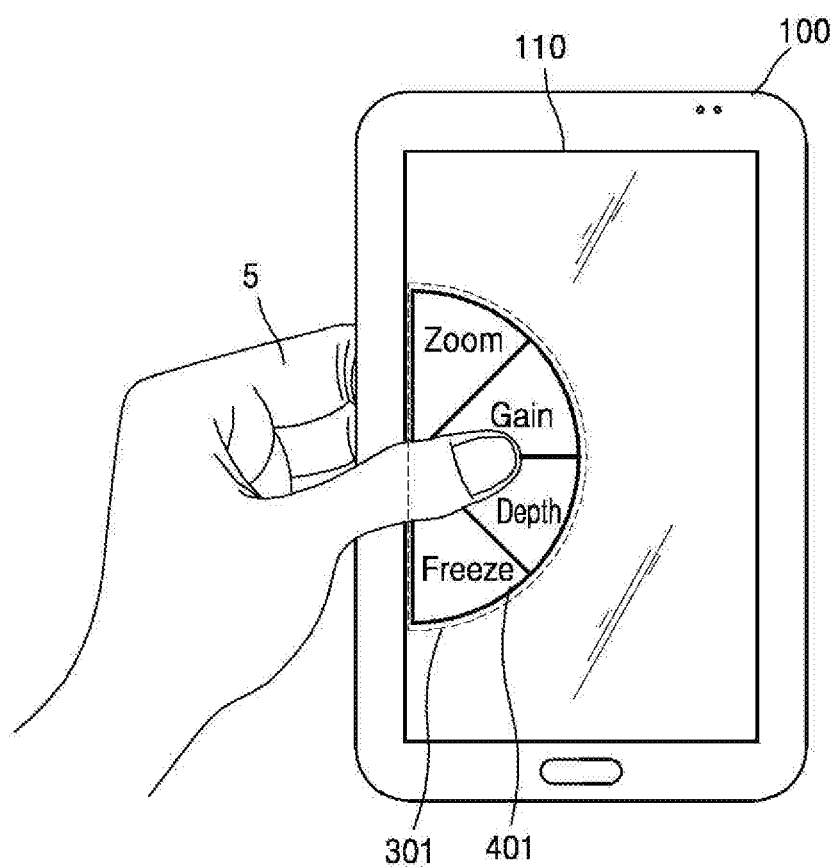
FIG. 4 illustrates a medical image display apparatus that provides a user interface (UI) based on a size of a finger-touchable range, according to an exemplary embodiment.

A method of providing, by the medical image display apparatus 100 of FIG. 4, a UI based on a size of a touch range of a finger of a user according to an exemplary embodiment will now be described in more detail with reference to FIG. 5.

Figure 5:
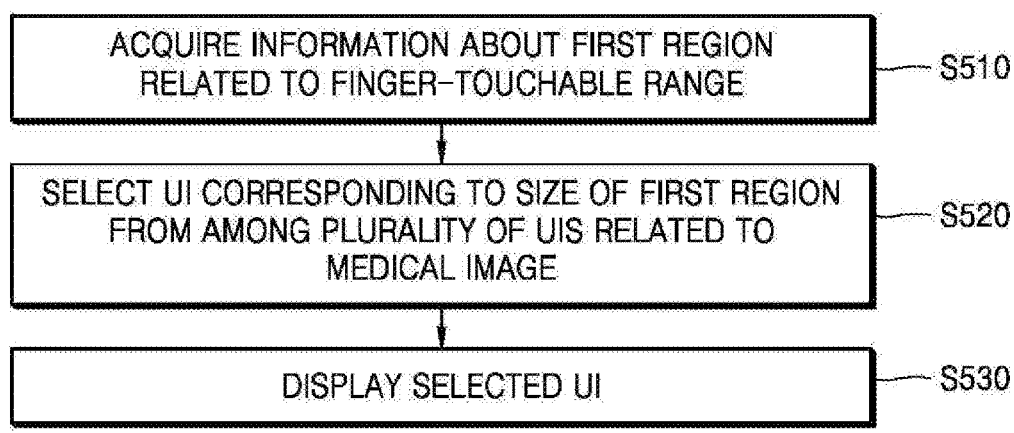
FIG. 5 is a flowchart of a method of providing, by a medical image display apparatus, a UI based on a size of a finger-touchable range, according to an exemplary embodiment.

FIG. 5 is a flowchart of an exemplary method of providing, by the medical image display apparatus 100, a UI based on a size of a finger-touchable range, according to an exemplary embodiment. In some exemplary embodiments, "finger-touchable" may be used to indicate, for example, accessible by a finger, or "finger-accessible."

Referring to FIG. 5, the medical image display apparatus 100 may acquire information about a first region related to a finger-touchable range (S510). The touch range of the user's finger may mean a touch range on a touch screen that may be touched by a finger of a hand used by a user to grip the medical image display apparatus 100. The medical image display apparatus 100 may acquire information about the first region that defines a touch range on a touch screen that may be touched by a finger of a hand used by a user to grip the medical image display apparatus 100.

The information about the first region that defines a finger-touchable range may include information about at least one of a maximum distance between a reference point and a point that may be touched by the user's finger (hereinafter, referred to as a 'maximum finger-touchable distance'), a maximum angle formed at the intersection between a line connecting a reference point to a first point that may be touched by the user's finger and a line connecting the reference point to a second point that may be touched by the user's finger (hereinafter, referred to as a 'maximum finger-touchable angle'), a maximum area of a finger-touchable region, and a shape of the region.

Figure 6:
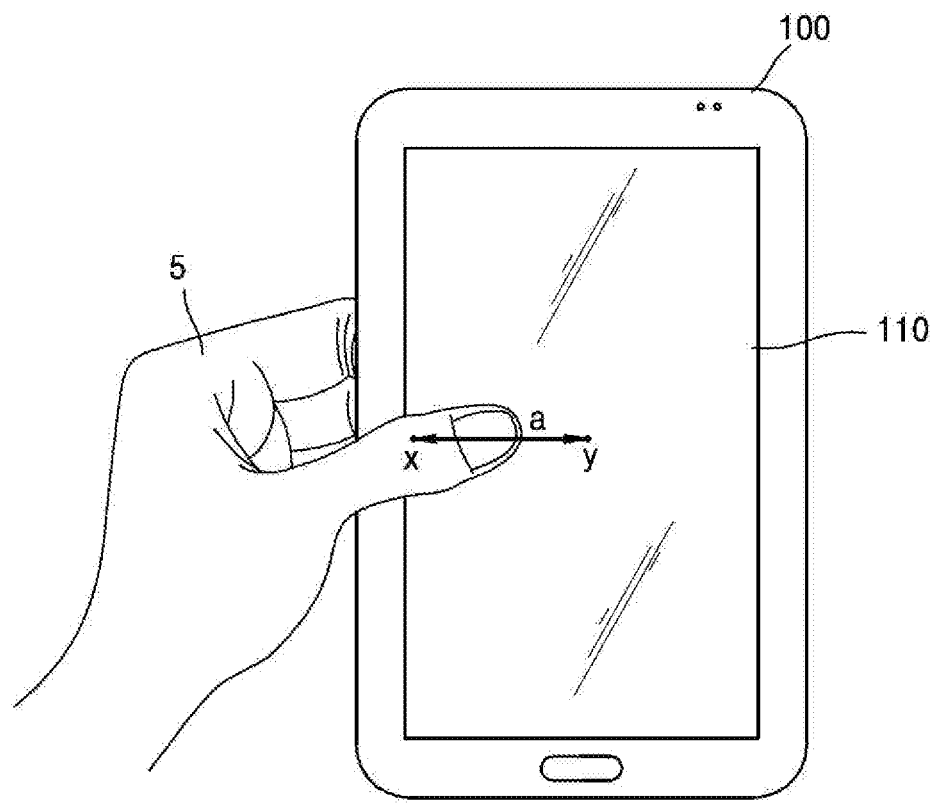
FIG. 6, FIG. 7 and FIG. 8 illustrate examples of pieces of information about a first region for defining a finger-touchable range.
Figure 7:
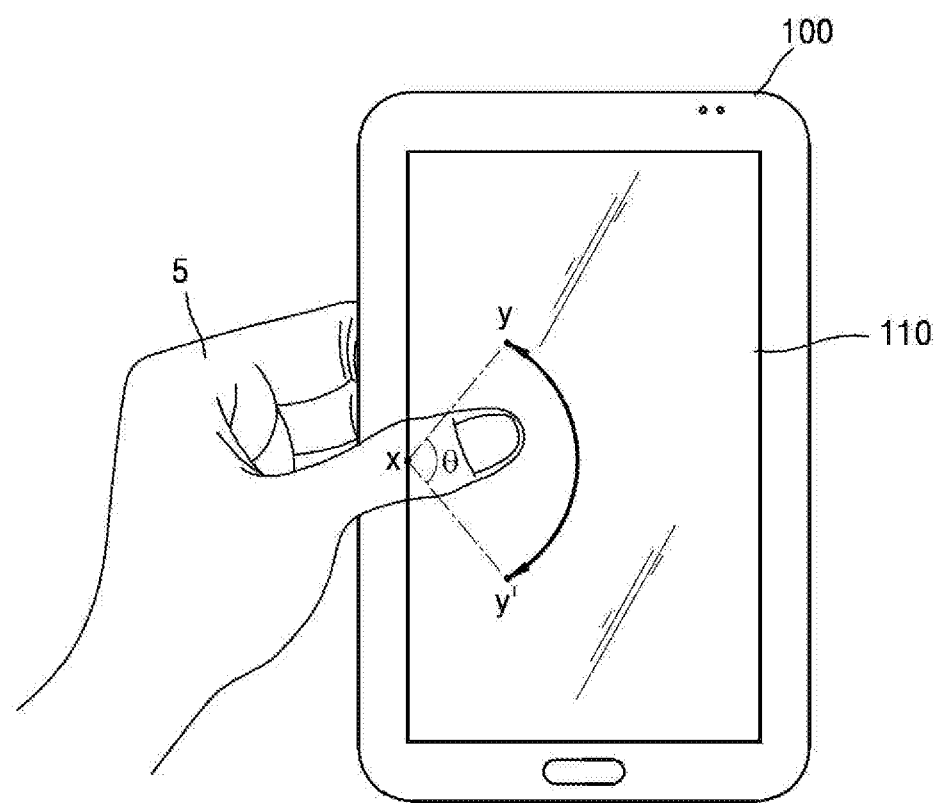
Figure 8:
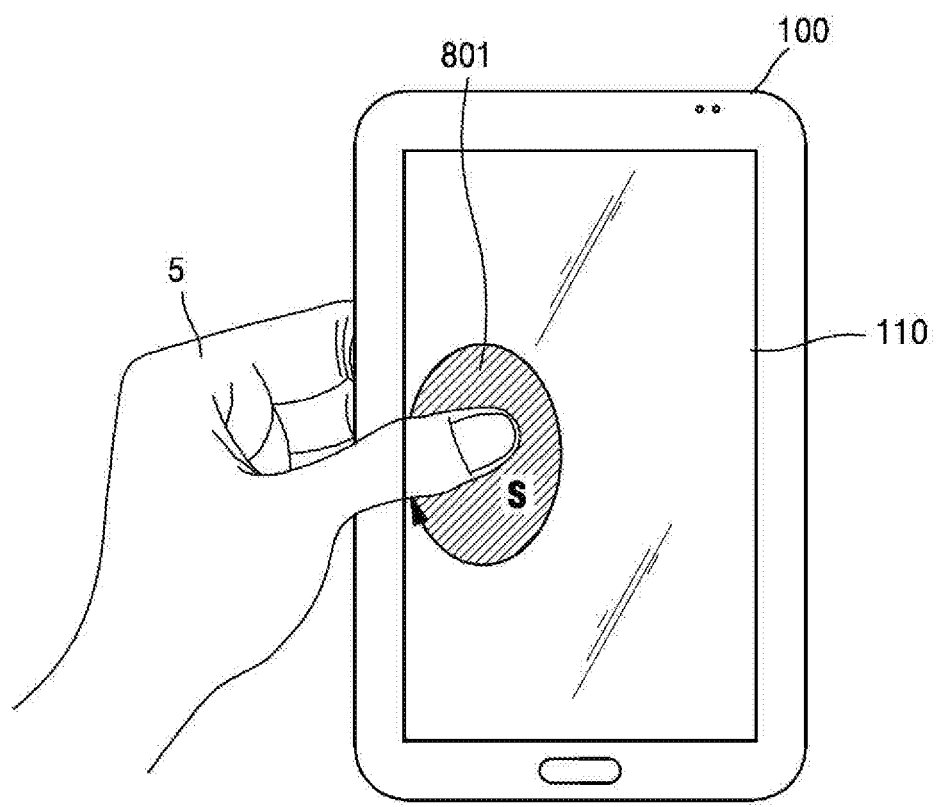

FIGS. 6 through 8 illustrate examples of pieces of information about a first region for defining a finger-touchable range.

Referring to FIG. 6, a medical image display apparatus 100 may acquire a maximum distance between a reference point x and a point y that may be touched by a finger of a user 5 as information about the first region.

The reference point may be predetermined as a default value or be set by the user 5. In some exemplary embodiments, the medical image display apparatus 100 may detect a position of a hand of the user 5 which is used to grip the medical image display apparatus 100 and determine the reference point based on the position of the hand of the user 5. The medical image display apparatus 100 may detect the position of the hand of the user 5 used to grip the medical image display apparatus 100 by using, for example, a sensor provided on a bezel surrounding a touch screen 110.

For example, the medical image display apparatus 100 may determine the reference point based on a position where the hand of the user 5 used to grip the medical image display apparatus 100 is in contact with the bezel, or a position where a finger touching the touch screen 110 of the medical image display apparatus 100 meets an edge of the touch screen 110.

Referring to FIG. 7, the medical image display apparatus 100 may acquire a maximum angle θ formed at the intersection between a line xy from a reference point x to a first point y that may be touched by the finger of the user 5 and a line xy' from the reference point x to a second point y' that may be touched by the finger of the user 5 as information about the first region.

Referring to FIG. 8, the medical image display apparatus 100 may acquire a maximum area s or a shape of a region 801 that may be touched by the finger of the user 5 as information about the first region.

The medical image display apparatus 100 may acquire information about the first region by receiving the information about the first region from the outside or analyzing a user input.

For example, the medical image display apparatus 100 may identify a user of the medical image display apparatus 100 and acquire information about a first region prestored for the identified user. To acquire information about the first region, the medical image display apparatus 100 may receive user identification (ID) information and read out information about a touch range corresponding to the received user ID information from a memory. The medical image display apparatus 100 may acquire the information about the first region from a memory included in the medical image display apparatus 100, a memory of an external device, and an external server. Methods of receiving user ID information will be described in greater detail below with reference to FIGS. 13 through 16.

As another example, the medical image display apparatus 100 may acquire information about the first region by analyzing a touch gesture received from a user. The medical image display apparatus 100 may display a guide image for guiding a touch gesture from the user and receive the touch gesture corresponding to the guide image from the user. The medical image display apparatus 100 may then acquire information about the first region by analyzing the received touch gesture. Methods of acquiring information about the first region based on a touch gesture from a user will be described in greater detail below with reference to FIGS. 17 through 24.

As another example, the medical image display apparatus 100 may receive information about the first region directly from the user. The medical image display apparatus 100 may display a UI for receiving information about the first region and acquire a user input received from the user as the information about the first region. For example, the medical image display apparatus 100 may receive from the user information about at least one of a maximum finger-touchable distance, a maximum finger-touchable angle, a maximum area of a finger-touchable region, and a shape of the region. A method of receiving information about the first region from the user will be described in greater detail below with reference to FIGS. 25 and 26.

According to an exemplary embodiment, the medical image display apparatus 100 may be temporarily fixed at a certain position or be carried by the user when it is used. For example, the medical image display apparatus 100 may be temporarily fixed at a certain position for use thereof by being attached to another device or mounted on a stationary object. If the medical image display apparatus 100 is held and moved by the user, the medical image display apparatus 100 may acquire information about a finger-touchable range and provide a UI suitable for the touch range.

For example, if the medical image display apparatus 100 is detached from a medical image acquisition apparatus for acquiring medical image data from an object, the medical image display apparatus 100 may acquire information about a first region.

As another example, the medical image display apparatus 100 may detect motion information of the medical image display apparatus 100. If it is determined, based on the motion information, that the medical image display apparatus 100 is moving, the medical image display apparatus 100 may acquire information about the first region. For example, the medical image display apparatus 100 may detect at least one of a speed, an acceleration, and a slope thereof and, if the detected value is greater than or equal to a threshold value thereof, the medical image display apparatus 100 may determine that the medical image display apparatus 100 is moving.

As another example, if the medical image display apparatus 100 senses a user's hand used to grip the medical image display apparatus 100, the medical image display apparatus 100 may acquire information about the first region. In this case, the medical image display apparatus 100 may detect the user's hand used to grip the medical image display apparatus 100 via a sensor disposed on the bezel surrounding the touch screen 110.

According to an exemplary embodiment, if a user holding the medical image display apparatus 100 is changed, the medical image display apparatus 100 may acquire information about a touch range of a new user's finger. The medical image display apparatus 100 may provide a UI suitable for the new user based on the newly acquired information. In some exemplary embodiments, if a position of a user's hand used to grip the medical image display apparatus 100 is changed, the medical image display apparatus 100 may acquire again information about a finger-touchable range. The medical image display apparatus 100 may provide, based on the newly acquired information, a UI suitable for a new position of the user's hand.

Referring back to FIG. 5, the medical image display apparatus 100 may select a UI corresponding to a size of the first region from among a plurality of UIs related to a medical image (S520).

The plurality of UIs related to a medical image may include at least one of a GUI for setting parameters related to the medical image, a GUI for controlling an external device or server connected to the medical image display apparatus 100, and a UI for displaying information about the medical image.

The medical image display apparatus 100 may select a UI corresponding to a size of the first region from among the plurality of UIs, based on a result of comparing the size of the first region with a threshold value. The threshold value may be predetermined as a default value or may be set by the user.

For example, the medical image display apparatus 100 may compare at least one of a maximum finger-touchable distance, a maximum finger-touchable angle, and a maximum area of a finger-touchable region, with a threshold value and select a UI based on a comparison result. Methods of selecting, by the medical image display apparatus 100, a UI corresponding to a size of the first region will be described in greater detail below with reference to FIGS. 27 and 28.

The medical image display apparatus 100 may perform a function selected by the user from among all functions provided by the medical image display apparatus 100 in relation to a medical image. The medical image display apparatus 100 may provide a UI that allows the user to select at least one function. Each of the plurality of UIs related to a medical image may include at least one icon that allows the user to select a different number of functions.

The medical image display apparatus 100 may select a number of functions corresponding to a size of the first region from among all functions related to a medical image, which are provided by the medical image display apparatus 100. The medical image display apparatus 100 may select, from among the plurality of UIs, a UI including at least one icon corresponding to the selected functions. For example, as the size of the first region increases, the medical image display apparatus 100 may select a UI including more functions.

According to an exemplary embodiment, the medical image display apparatus 100 may provide a plurality of UIs capable of receiving user inputs based on various touch gestures.

Examples of a user's touch gesture may include tap, touch and hold, double tap, drag, panning, flick, drag and drop, pinch, swipe, etc.

"Tap" may be performed by touching a screen with a finger or touch instrument (e.g., an electronic pen) and immediately lifting the finger or touch instrument off the screen without moving it around.

"Touch and hold" may occur when a user touches a screen with a finger or touch instrument (e.g., an electronic pen) and holds the touch input for a threshold time (e.g., 2 seconds) or longer. In other words, a time difference between a touch-in time point and a touch-out time point is greater than or equal to the threshold time (e. g., 2 seconds).

"Double tap" may occur when a user touches a screen with the user's finger or a touch instrument (e.g., a stylus) twice in less than a threshold time (e.g., 2 seconds).

"Drag" may occur when a user places a finger or touch instrument on a screen moves the finger or the touch tool to another location on the screen without lifting it from the screen. The drag gesture may be used to move an object or perform a pan gesture as described below.

"Panning" may be a gesture in which a user performs a drag without selecting an object. Because the panning gesture is performed without selecting a specific object, the panning may move a page in a screen or an object group in the page instead of moving an object in the page.

"Flick" may occur when a user performs a drag at a threshold speed (e.g., 100 pixels/s) or faster by using a finger or touch instrument. Drag and Flick gestures may be distinguished from each other based on whether the finger or the touch instrument moves at the threshold speed (e.g., 100 pixels/s) or higher.

"Drag and drop" may occur when a user drags an object to a certain location on a screen and drops the object thereon by using a finger or touch instrument.

"Pinch" may be a gesture where a user places two fingers on a screen and moves the two fingers in different directions without lifting the two fingers from the screen. The pinch gesture is used to zoom in an object or page (Pinch Open) or zoom out the object or page (Pinch Close). In this case, a zoom-in ratio or zoom-out ratio is determined according to a distance between the two fingers.

"Swipe" may be performed by touching an object on a screen with a finger or touch instrument and moving the finger or touch instrument in a certain direction by a certain distance.

A size of a region on a touch screen that a user may use to input a touch gesture varies depending on the type of touch gesture. For example, when the user inputs touch gestures involving moving a finger or touch instrument, such as drag, panning, flick, and swipe gestures, the user may use a greater region on a touch screen than when he or she inputs a tap, touch and hold, or double tap gesture. Thus, according to an exemplary embodiment, the medical image display apparatus 100 may provide a plurality of UIs configured to receive different touch gestures according to a size of a finger-touchable range.

The medical image display apparatus 100 may select a touch gesture corresponding to a size of the first region from among different types of touch gestures. The medical image display apparatus 100 may select a UI configured to receive the selected touch gesture from among a plurality of UIs. For example, if the size of the first region is greater than a threshold value, the medical image display apparatus 100 may select a first UI configured to receive at least one touch gesture among drag, panning, flick, and swipe gestures. Otherwise, if the size of the first region is less than or equal to the threshold value, the medical image display apparatus 100 may select a second UI configured to receive at least one touch gesture among tap, touch and hold, and double tap gestures.

In addition, a thickness of a finger, a strength of a finger touching the touch screen 110, or a posture of a finger touching the touch screen 110 may vary according to user. Thus, a contact area of a finger with the touch screen 110 when the finger touches the touch screen 110 (hereinafter, referred to as a 'finger contact area') may vary according to users. Furthermore, even for the same user, a finger contact area may vary according to, for example, which finger touches the touch screen 110, or a posture of a finger touching the touch screen 110.

For example, as a thickness of a finger touching the touch screen 110 increases, a finger contact area may increase. Furthermore, as a strength of a touch on the touch screen 110 increases, the finger contact area may increase. As a finger touching the touch screen 110 becomes more perpendicular to the touch screen 110, the finger contact area may decrease.

Thus, the medical image display apparatus 100 may display a UI by further taking into account a user's finger contact area. The medical image display apparatus 100 may select a UI including at least one icon having a size corresponding to a user's finger contact area from among a plurality of UIs. For example, as the user's finger contact area decreases, the medical image display apparatus 100 may select a UI including a smaller icon, as described in more detail below with reference to FIGS. 58 and 59.

According to an exemplary embodiment, the medical image display apparatus 100 may select one UI from among a plurality of UIs by further taking into account at least one of a direction in which the medical image display apparatus 100 displays content and a side of the medical image display apparatus 100 where a user's hand used to grip the medical image display apparatus 100 is located, as described in more detail below with reference to FIGS. 44 through 52.

The medical image display apparatus 100 may display the UI selected in operation S520 previously (S530).

The medical image display apparatus 100 may display the selected UI at a position determined based on a position of a user's hand or finger.

To ensure a medical image provided via the medical image display apparatus 100 may be used for diagnosis or treatment of a disease, the medical image has to be provided to the user without distortion. For example, if a UI is displayed to overlap a medical image, accuracy of diagnosis and treatment of a disease may be degraded. Thus, the medical image display apparatus 100 may change a position where the medical image is to be displayed so that a selected UI and the medical image do not overlap each other, based on a position where the selected UI is displayed.

According to various exemplary embodiments, to provide a UI suitable for a user who holds and uses the medical image display apparatus 100, if the medical image display apparatus 100 determines that the user is holding and using the medical image display apparatus 100, the medical image display apparatus 100 may acquire information about a finger-touchable range. In some exemplary embodiments, to provide a UI suitable for each user, if a posture of a user's hand used to grip the medical image display apparatus 100 or a user is changed, the medical image display apparatus 100 may acquire information about a finger-touchable range.

Figure 9A:
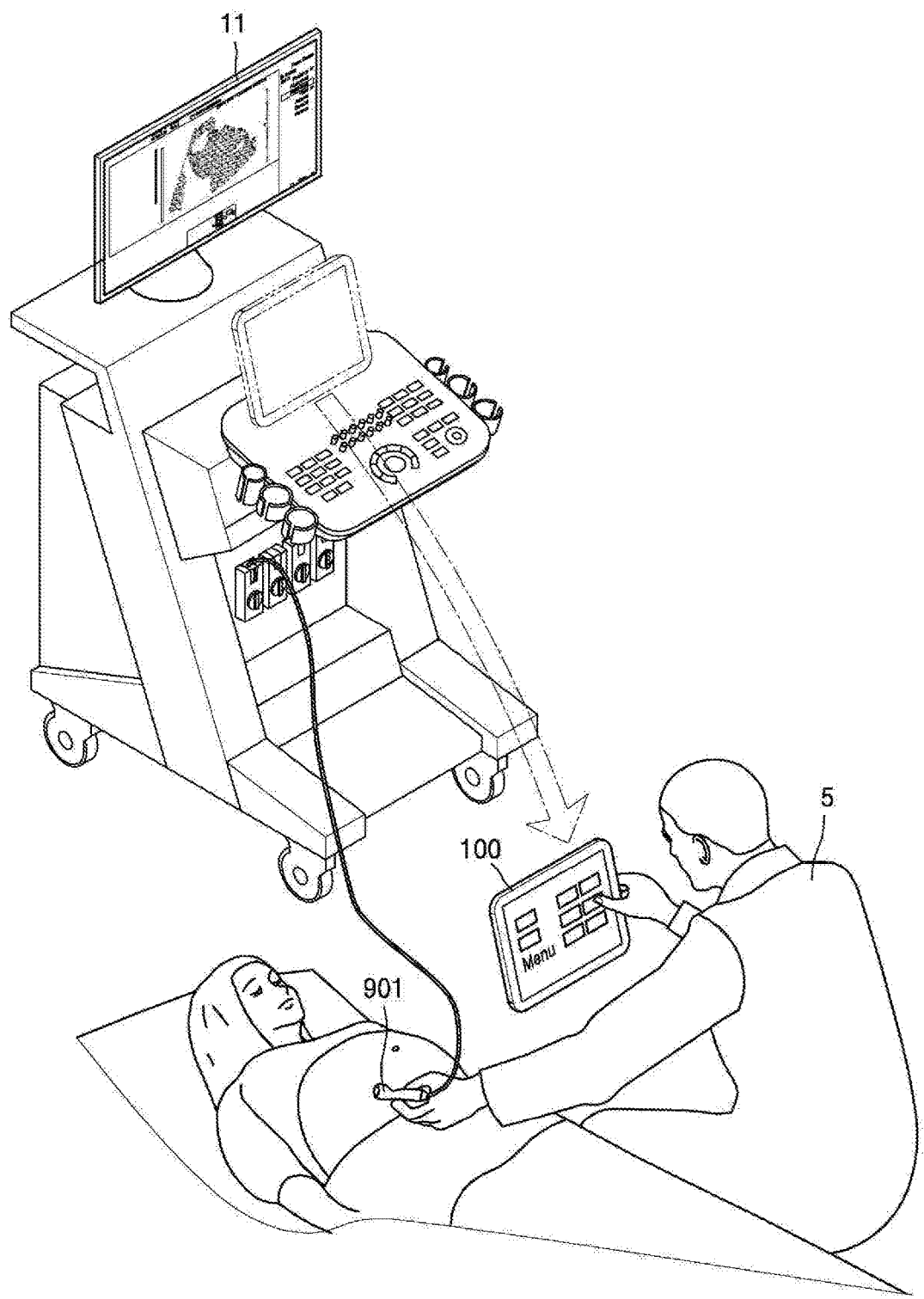
FIG. 9A and FIG. 9B are diagrams for explaining a method of acquiring information about a first region when a medical image display apparatus is detached from a medical image acquisition apparatus, according to an exemplary embodiment.
Figure 9B:
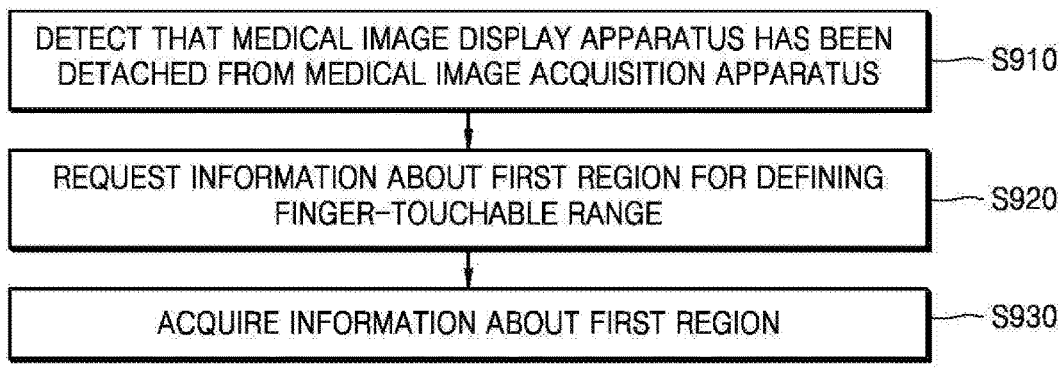

FIGS. 9A and 9B are diagrams for explaining a method of acquiring information about a first region when a medical image display apparatus 100 is detached from a medical image acquisition apparatus, according to an exemplary embodiment.

As shown in FIG. 9A, the medical image display apparatus 100 may be attached to or detached from an ultrasound diagnosis device 11.

The ultrasound diagnosis device 11 may transmit an ultrasound signal to an object via an ultrasound probe 901 and generate ultrasound image data based on an ultrasound signal reflected from the object. The ultrasound probe 901 may be connected to the ultrasound diagnosis device 11 by wire or wirelessly. The medical image display apparatus 100 may be included in the ultrasound diagnosis device 11 or may be a separate device that is connected to the ultrasound diagnosis device 11 by wire or wirelessly. The medical image display apparatus 100 may generate an ultrasound image by using ultrasound image data received from the ultrasound diagnosis device 11 and display the generated ultrasound image.

When the ultrasound diagnosis device 11 is located far away from a user 5 or the object as shown in FIG. 9A, the user 5 may detach the medical image display apparatus 100 from the ultrasound diagnosis device 11 to be provided with an ultrasound image of the object at a position close to the user 5 or the object.

The user 5 may grip the detached medical image display apparatus 100 with one hand while using the ultrasound probe 901 with the other hand. Thus, if the medical image display apparatus 100 is detached from the ultrasound diagnosis device 11, the medical image display apparatus 100 may determine that the user 5 is holding and using the medical image display apparatus 100 with one hand. When being detached from the ultrasound diagnosis device 11, the medical image display apparatus 100 may acquire information about a finger-touchable range and provide a UI based on the acquired information.

FIG. 9A illustrates an example where the medical image display apparatus 100 is connected to the ultrasound diagnosis device 11 by wire or wirelessly, and is attached to or detached from the ultrasound diagnosis device 11. However, exemplary embodiments are not limited to the example shown in FIG. 9A, and the medical image display apparatus 100 may be attached to or detached from not only the ultrasound diagnosis device 11 but also to or from other various medical image acquisition devices for acquiring medical image data from an object FIG. 9B is a flowchart of a method of acquiring information about a first region when the medical image display apparatus 100 is detached from a medical image acquisition apparatus, according to an exemplary embodiment.

The medical image display apparatus 100 may detect that the medical image display apparatus 100 has been detached from a medical image acquisition apparatus (S910).

To attach the medical image display apparatus 100 to the medical image acquisition apparatus, the medical image display apparatus 100 may include a fixing device for fixing the medical image display apparatus 100 on the medical image acquisition apparatus. In some exemplary embodiments, the medical image acquisition apparatus may include a fixing device for fixing the medical image display apparatus 100, a support for supporting the medical image display apparatus 100, or a groove for accommodating the medical image display apparatus 100 therein.

The medical image display apparatus 100 may acquire information about whether the medical image display apparatus 100 has been detached from the medical image acquisition apparatus by using a sensing unit or sensors provided in the medical image display apparatus 100. For example, the medical image display apparatus 100 may acquire the information about whether the medical image display apparatus 100 has been detached from the medical image acquisition apparatus by using a magnetic sensor, an acceleration sensor, a gyroscope sensor, a proximity sensor, an optical sensor, a depth sensor, an infrared sensor, or an ultrasound sensor included therein.

The medical image display apparatus 100 may request information about the first region for defining a finger-touchable range (S920).

The medical image display apparatus 100 may request the information about the first region from a memory included in the medical image display apparatus 100, a memory of an external device, or an external server. In some exemplary embodiments, the medical image display apparatus 100 may request the information about the first region from the user by displaying a guide image that elicits a touch gesture from the user. In addition, the medical image display apparatus 100 may request information about the first region from the user by displaying a UI for receiving the information about the first region.

The medical image display apparatus 100 may acquire the information about the first region for defining a finger-touchable range (S930).

The medical image display apparatus 100 may acquire the information about the first region from a memory included therein, a memory of an external device, or an external server. In some exemplary embodiments, the medical image display apparatus 100 may acquire the information about the first region by analyzing a touch gesture received from the user in response to a guide image. In other exemplary embodiments, the medical image display apparatus 100 may receive the information about the first region directly from the user. Because operation S930 illustrated in FIG. 9B may correspond to operation S510 illustrated in FIG. 5, the same descriptions as provided above with respect to operation S510 will be omitted below.

Figure 10A:
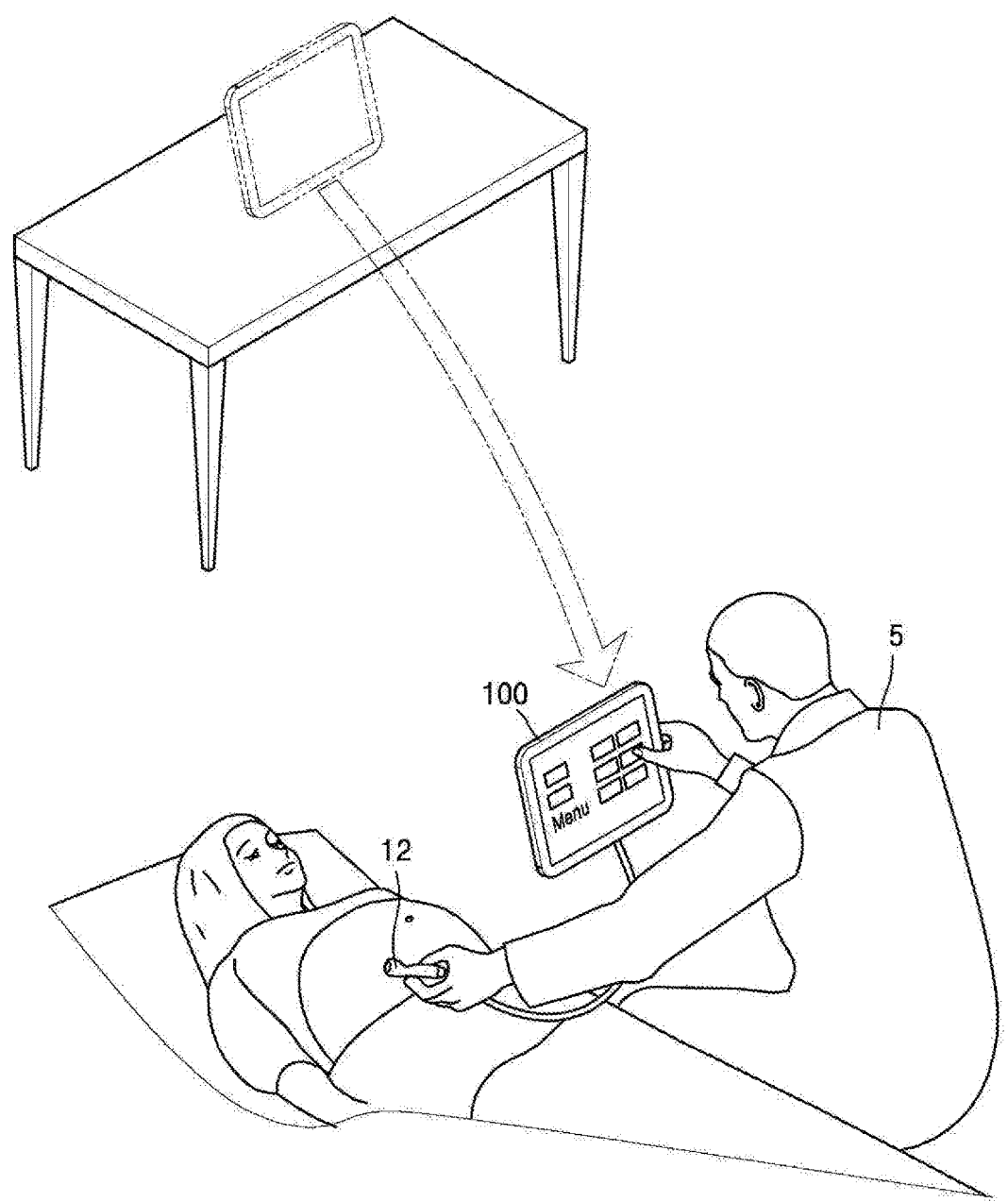
FIG. 10A and FIG. 10B are diagrams for explaining a method of acquiring information about a first region when a medical image display apparatus is moved by a user, according to an exemplary embodiment.
Figure 10B:
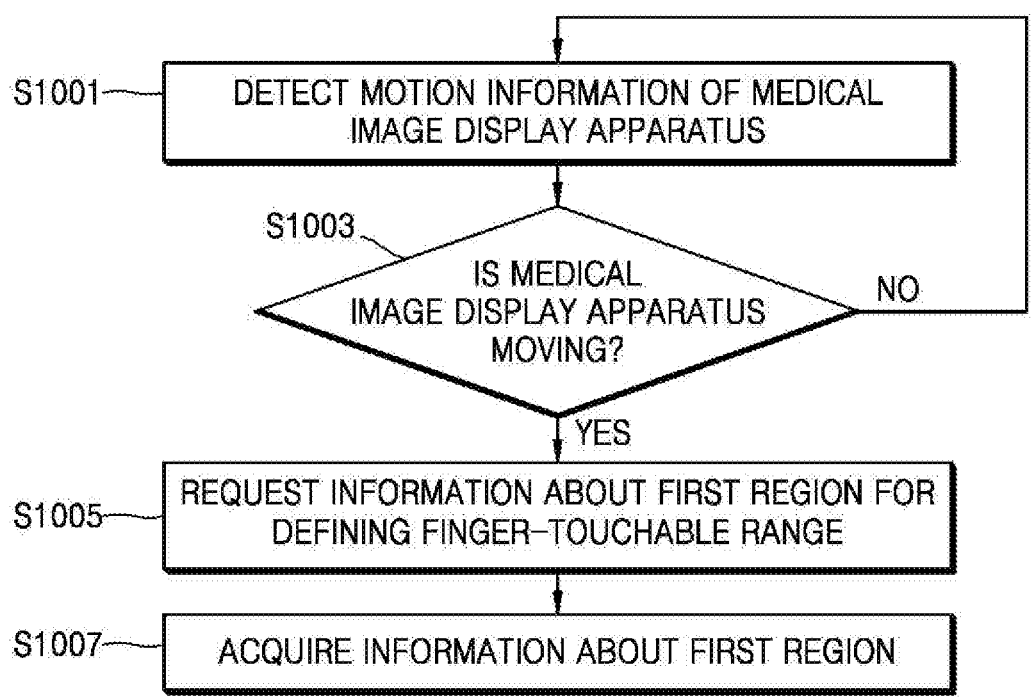

FIGS. 10A and 10B are diagrams for explaining a method of acquiring information about a first region when the medical image display apparatus 100 is moved by a user 5, according to an exemplary embodiment.

According to an exemplary embodiment, the medical image display apparatus 100 may be temporarily fixed at a certain position for use thereof by being attached to another device or mounted on a stationary object. For example, as shown in FIG. 10A, the medical image display apparatus 100 may be temporarily fixed at a certain position during its use by being placed on a stationary object such as a desk. The medical image display apparatus 100 may be connected to an ultrasound probe 12 by wire or wirelessly. The ultrasound probe 12 may transmit an ultrasound signal to an object according to a driving signal applied by the medical image display apparatus 100 and receive an echo signal reflected by the object. The ultrasound probe 12 may acquire ultrasound image data based on the received echo signal and transmit the acquired ultrasound image data to the medical image display apparatus 100. The medical image display apparatus 100 may display an ultrasound image by using the ultrasound image data received from the ultrasound probe 12.

As shown in FIG. 10A, in order to be provided with an ultrasound image of the object at a position close to the user 5 or the object, the user 5 may move near the object the medical image display apparatus 100 that has been temporarily fixed at a certain position to be used.

The user 5 may grip the detached medical image display apparatus 100 with one hand while using the ultrasound probe 12 with the other hand. Thus, if the medical image display apparatus 100 is moved by the user 5, the medical image display apparatus 100 may determine that the user 5 is holding and using the medical image display apparatus 100 with one hand. If it is determined that the medical image display apparatus is being moved by the user 5, the medical image display apparatus 100 may acquire information about a finger-touchable range and provide a UI based on the acquired information.

FIG. 10B is a flowchart of a method of acquiring information about a first region when the medical image display apparatus 100 is moved by the user, according to an exemplary embodiment.

According to an exemplary embodiment, the medical image display apparatus 100 may detect motion information of the medical image display apparatus 100 (S1001).

The medical image display apparatus 100 may include a fixing device for fixing the medical image display apparatus 100 on another device for attachment to the other device. In some exemplary embodiments, the medical image display apparatus 100 may include a support for placing it on a stationary object.

The medical image display apparatus 100 may acquire motion information of the medical image display apparatus 100 by using a sensing unit provided in the medical image display apparatus 100. For example, the medical image display apparatus 100 may acquire the motion information of the medical image display apparatus 100 by using a magnetic sensor, an acceleration sensor, a gyroscope sensor, a proximity sensor, an optical sensor, a depth sensor, an infrared sensor, or an ultrasound sensor included therein. The motion information of the medical image display apparatus 100 may include at least one of information about whether a position of the medical image display apparatus 100 has changed, a speed at which the medical image display apparatus 100 moves, an acceleration with which the medical image display apparatus 100 moves, information about whether the medical image display apparatus 100 is rotating, and a slope of the medical image display apparatus 100.

The medical image display apparatus 100 may determine whether the medical image display apparatus 100 is moving based on the detected motion information (S1003).

For example, the medical image display apparatus 100 may detect at least one of a speed, an acceleration, and a slope of the medical image display apparatus 100 as the motion information. The medical image display apparatus 100 may determine whether it is moving by comparing the detected value to a threshold value. The threshold value may be predetermined as a default value or may be set by the user.

If it is determined, based on the motion information that the medical image display apparatus 100 is moving, the medical image display apparatus 100 may request information about a first region (See S1005). Otherwise, if it is not determined, based on the motion information, that the medical image display apparatus 100 is moving, the medical image display apparatus 100 returns to operation S1001 and detects motion information thereof again.

The medical image display apparatus 100 may request information about a first region for defining a touch range of a finger of the user (S1005). The medical image display apparatus 100 may request the information about the first region from a memory included in the medical image display apparatus 100, a memory of an external device, or an external server. In some exemplary embodiments, the medical image display apparatus 100 may request the information about the first region from the user by displaying a guide image that elicits a touch gesture from the user. In addition, the medical image display apparatus 100 may request the information about the first region from the user by displaying a UI for receiving the information about the first region.

The medical image display apparatus 100 may acquire the information about the first region for defining the touch range of the finger of the user (S1007).

The medical image display apparatus 100 may acquire the information about the first region from a memory included therein, a memory of an external device, or an external server. In some exemplary embodiments, the medical image display apparatus 100 may acquire the information about the first region by analyzing a touch gesture received from the user in response to a guide image. In some exemplary embodiments, the medical image display apparatus 100 may receive the information about the first region directly from the user 5. Because operation S1007 illustrated in FIG. 10B may correspond to operation S510 illustrated in FIG. 5, the same descriptions as provided above with respect to operation S510 will be omitted below.

Figure 11A:
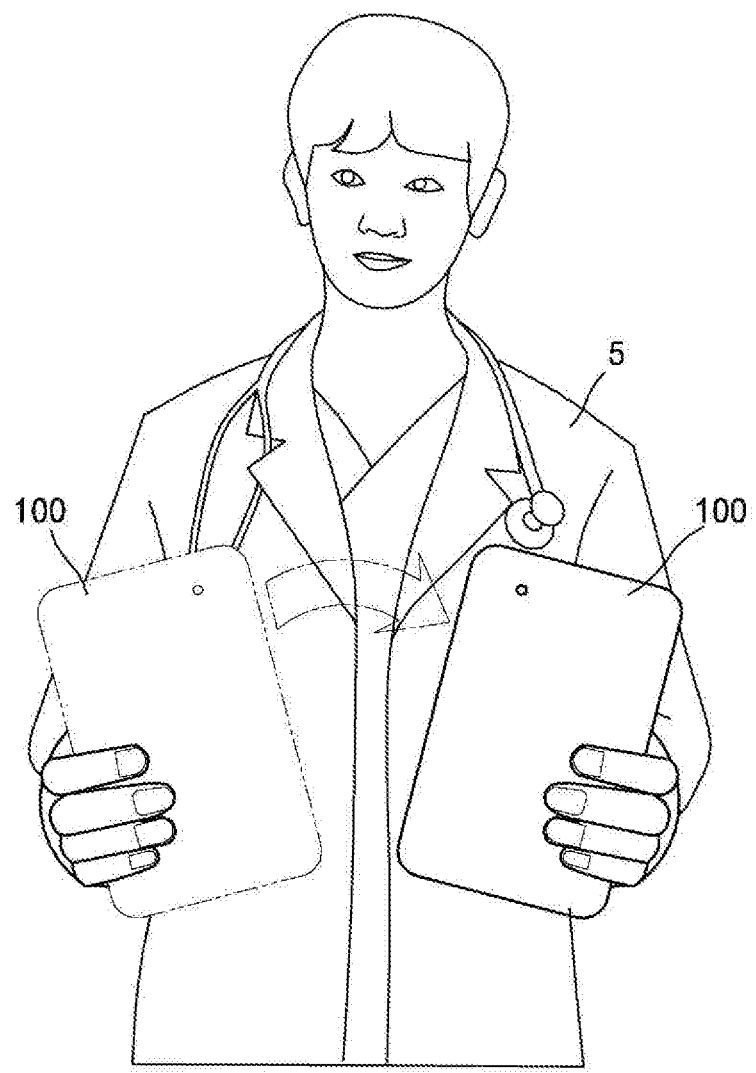
FIG. 11A and FIG. 11B are diagrams for explaining a method of acquiring information about a first region when a position of a user's hand, which is used to grip a medical image display apparatus, is changed, according to an exemplary embodiment.
Figure 11B:
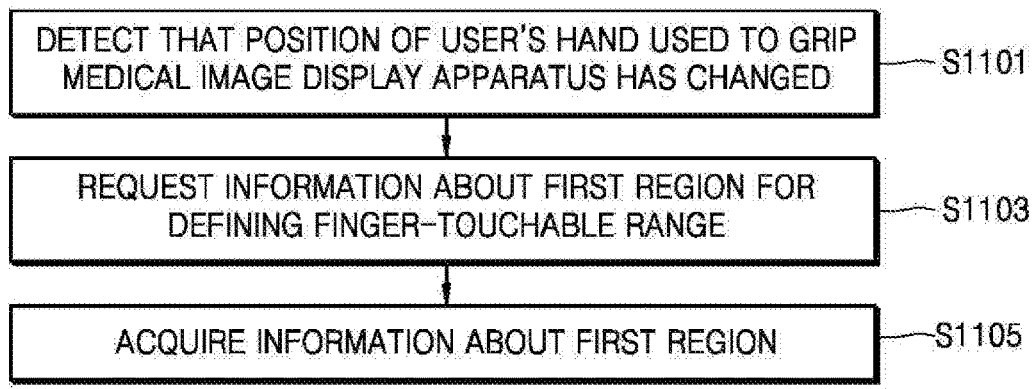

FIGS. 11A and 11B are diagrams for explaining a method of acquiring information about a first region when a position of a hand of a user 5, which is used to grip a medical image display apparatus 100, is changed, according to an exemplary embodiment.

As shown in FIG. 11A, when the user 5 changes a hand used to grip the medical image display apparatus 100, a posture of a hand of the user 5, which is used to grip the medical image display apparatus 100, may be changed. If the posture of the hand used to grip the medical image display apparatus 100 is changed, a touch range of a finger of the user 5 may be varied.

Thus, to provide a UI suitable for a posture of a hand of the user 5, the medical image display apparatus 100 may detect whether a position of a hand of the user 5 used to grip the medical image display apparatus 100 has changed. If the position of the hand of the user 5 is changed, the medical image display apparatus 100 may acquire information about a touch range of a finger of the user 5. The medical image display apparatus 100 may provide a UI based on the acquired information.

FIG. 11A illustrates an example where the user 5 changes a hand used to grip the medical image display apparatus 100 from the right hand to the left hand. However, exemplary embodiments are not limited thereto the example illustrated in FIG. 11A. The medical image display apparatus 100 may detect not only a change in a hand used to grip the medical image display apparatus 100 but also various changes in a position of the hand of the user 5 used to grip the medical image display apparatus 100, such as adjustment of a grip of the user 5 on the medical image display apparatus 100.

FIG. 11B is a flowchart of a method of acquiring information about a first region when a position of a hand of the user 5, which is used to grip the medical image display apparatus 100 is changed, according to an exemplary embodiment.

The medical image display apparatus 100 may detect that a position of a hand of the user 5 used to grip the medical image display apparatus 100 has changed (S1101).

The medical image display apparatus 100 may detect whether a position of a hand of the user 5 used to grip the medical image display apparatus 100 has changed by using a sensing unit provided in the medical image display apparatus 100. For example, the medical image display apparatus 100 may detect whether the position of the hand of the user 5 used to grip the medical image display apparatus 100, has changed by using a magnetic sensor, an acceleration sensor, a gyroscope sensor, a proximity sensor, an optical sensor, a depth sensor, an infrared sensor, or an ultrasound sensor included therein. As another example, the medical image display apparatus 100 may detect the position of the hand of the user 5 used to grip the medical image display apparatus 100 via a sensor disposed on the bezel surrounding the touch screen 110. In some exemplary embodiments, the medical image display apparatus 100 may detect the position of the hand of the user 5 by sensing a finger that touches the touch screen 110.

When the medical image display apparatus 100 detects that the position of the hand of the user 5 used to grip the medical image display apparatus 100 has changed, the medical image display apparatus 100 may request information about a first region (S1103).

The medical image display apparatus 100 may request the information about the first region from a memory included in the medical image display apparatus 100, a memory of an external device, or an external server. In some exemplary embodiments, the medical image display apparatus 100 may request the information about the first region from the user 5 by displaying a guide image that elicits a touch gesture from the user 5. In other exemplary embodiments, the medical image display apparatus 100 may request the information about the first region from the user 5 by displaying a UI for receiving the information about the first region.

The medical image display apparatus 100 may acquire the information about the first region for defining a touch range on the touch screen 110 that may be touched by a finger of the user 5 (S1105).

The medical image display apparatus 100 may acquire the information about the first region from a memory included therein, a memory of an external device, or an external server. In some exemplary embodiments, the medical image display apparatus 100 may acquire the information about the first region by analyzing a touch gesture received from the user 5 in response to a guide image. In further exemplary embodiments, the medical image display apparatus 100 may receive the information about the first region directly from the user 5. Because operation S1105 illustrated in FIG. 11B corresponds to operation S510 illustrated in FIG. 5, the same descriptions as provided above with respect to operation S510 will be omitted below.

Figure 12B:
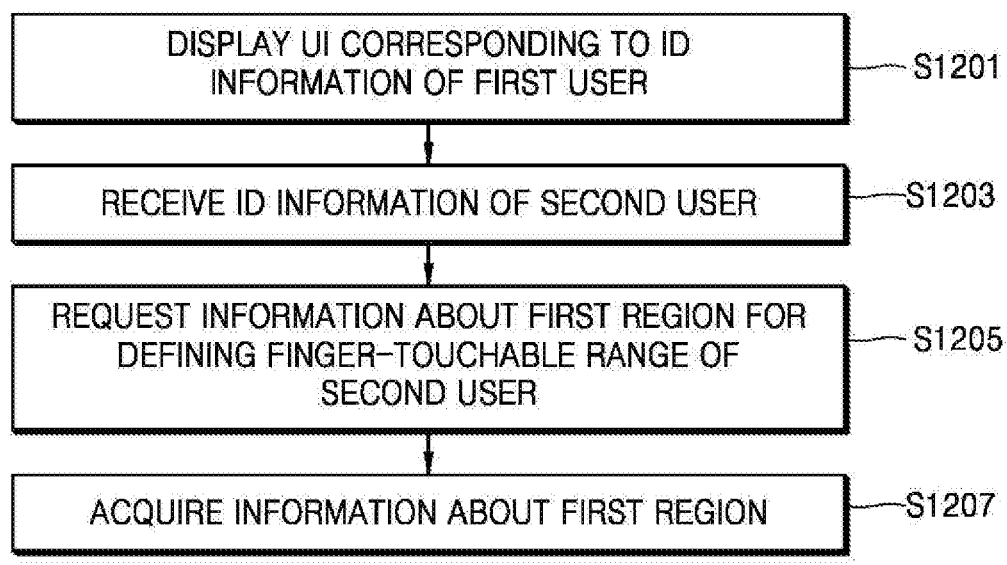

FIGS. 12A and 12B are diagrams for explaining a method of acquiring information about a first region when a user holding a medical image display apparatus 100 is changed, according to an exemplary embodiment.

As shown in FIG. 12A, when a user holding the medical image display apparatus 10 changes from a user 5-1 to a user 5-2, touch ranges of fingers of the users 5-1 and 5-2 may be different from each other.

Thus, to provide a UI suitable for each user, the medical image display apparatus 100 may detect whether a user holding the medical image display apparatus 100 has changed. If the user holding the medical image display apparatus 100 has changed, the medical image display apparatus 100 may acquire information about a touch range of a finger of a new user. The medical image display apparatus 100 may provide a UI suitable for the new user, based on the information about the touch range of the finger of the new user.

FIG. 12B is a flowchart of a method of acquiring information about a first region when a user holding the medical image display apparatus 100 is changed, according to an exemplary embodiment.

The medical image display apparatus 100 may display a UI corresponding to ID information of a first user holding the medical image display apparatus 100 (S1201).

The medical image display apparatus 100 may receive the ID information of the first user from the first user. In some exemplary embodiments, the medical image display apparatus 100 may receive the ID information of the first user via a predetermined operation performed by the first user. The predetermined operation may include bringing an ID card containing the ID information of the first user close to or into contact with the medical image display apparatus 100, entering a first user's name or ID via the medical image display apparatus 100, etc.

The medical image display apparatus 100 may acquire information about a first region corresponding to the ID information of the first user from a memory. The medical image display apparatus 100 may acquire the information about the first region from a memory included in the medical image display apparatus 100, a memory of an external device, or an external server. The information about the first region corresponding to the ID information of the first user may include information for defining a touch range of a finger of the first user. The medical image display apparatus 100 may display a UI corresponding to a size of the first region, based on the information about the first region.

When a user holding the medical image display apparatus 10 changes from the first user to a second user, the medical image display apparatus 100 may receive ID information of the second user (S1203).

For example, the medical image display apparatus 100 may detect whether a position of a user's hand used to grip the medical image display apparatus 100 has changed by using a sensing unit provided in the medical image display apparatus 100. In detail, the medical image display apparatus 100 may detect the position of the user's hand used to grip the medical image display apparatus 100 via a sensor disposed on the bezel surrounding the touch screen 110. In some exemplary embodiments, the medical image display apparatus 100 may detect the position of the user's hand by sensing a finger that touches the touch screen 110.

If it is detected that the position of the user's hand used to grip the medical image display apparatus 100 has changed, the medical image display apparatus 100 may determine that the user holding the medical image display apparatus 100 has changed. If the user holding the medical image display apparatus 100 has changed, the medical image display apparatus 100 may display a GUI for receiving ID information of a new user.

When the user holding the medical image display apparatus 100 changes from the first user to the second user, the medical image display apparatus 100 may receive ID information of the second user from the second user. In some exemplary embodiments, the medical image display apparatus 100 may receive the ID information of the second user via a predetermined operation performed by the second user. The predetermined operation may include bringing an ID card containing the ID information of the second user close to or into contact with the medical image display apparatus 100, or otherwise providing the ID card, or entering a second user's name or ID via the medical image display apparatus 100, etc.

The medical image display apparatus 100 may request information about a first region for defining a touch range of a finger of the second user (S1205).

The medical image display apparatus 100 may request the information about the first region corresponding to the second user from a memory included in the medical image display apparatus 100, a memory of an external device, or an external server. In some exemplary embodiments, the medical image display apparatus 100 may request the information about the first region from the second user by displaying a guide image that elicits a touch gesture from the second user. In other exemplary embodiments, the medical image display apparatus 100 may request the information about the first region from the second user by displaying a UI for receiving the information about the first region.

The medical image display apparatus 100 may acquire the information about the first region for defining a touch range on the touch screen 110 that may be touched by a finger of the second user (S1207).

The medical image display apparatus 100 may acquire the information about the first region from a memory included therein, a memory of an external device, or an external server. In some exemplary embodiments, the medical image display apparatus 100 may acquire the information about the first region by analyzing a touch gesture received from the second user in response to a guide image. In other exemplary embodiments, the medical image display apparatus 100 may receive the information about the first region directly from the second user. Because operation S1207 illustrated in FIG. 12B corresponds to operation S510 illustrated in FIG. 5, the same descriptions as provided above with respect to operation S510 will be omitted below.

According to various exemplary embodiments, to provide a UI suitable for a user, the medical image display apparatus 100 may acquire information about the first region prestored for the user. The medical image display apparatus 100 may receive ID information of the user and acquire the information about the first region corresponding to the ID information of the user from a memory. The medical image display apparatus 100 may acquire the information about the first region from a memory included in the medical image display apparatus 100, a memory of an external device, or an external server. Methods of receiving user ID information will now be described in more detail with reference to FIGS. 13 through 16.

Figure 13:
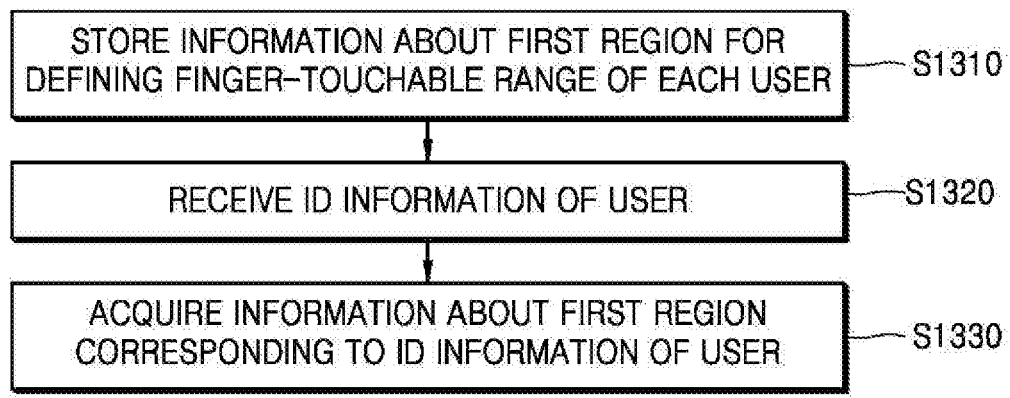
FIG. 13 is a flowchart of a method of acquiring, by a medical image display apparatus, information about a first region based on user identification (ID) information, according to an exemplary embodiment.

FIG. 13 is a flowchart of a method of acquiring, by the medical image display apparatus 100, information about a first region based on ID information of a user, according to an exemplary embodiment.

The medical image display apparatus 100 may store information about a first region for defining a touch range of a finger of each of a plurality of users (S1310).

The medical image display apparatus 100 may store information about the first region for defining a touch range of a finger of each of the users in a memory. In this case, the medical image display apparatus 100 may map information about the first region corresponding to each user to ID information of the user for storage in the memory.

The medical image display apparatus 100 may store information about the first region in a memory included in the medical image display apparatus 100, a memory of an external device, and an external server.

The medical image display apparatus 100 may receive ID information of a user holding the medical image display apparatus 100 (S1320).

When it is determined that the user is holding and using the medical image display apparatus 100 and if a posture of a hand of the user used to grip the medical image display apparatus 100 or the user himself/herself is changed, the medical image display apparatus 100 may receive the ID information of a corresponding new user.

The medical image display apparatus 100 may display a GUI for receiving ID information of a user and receive the ID information of the user from the user. The ID information of the user may include at least one of a user's name, ID, fingerprint, pattern, iris, voice, and face. The medical image display apparatus 100 may receive the ID information of the user via a predetermined operation performed by the user. The predetermined operation may include bringing an ID card containing the ID information of the user close to or into contact with the medical image display apparatus 100, or otherwise providing the ID card, or entering a user's name or ID via the medical image display apparatus 100, etc.

Figure 14:
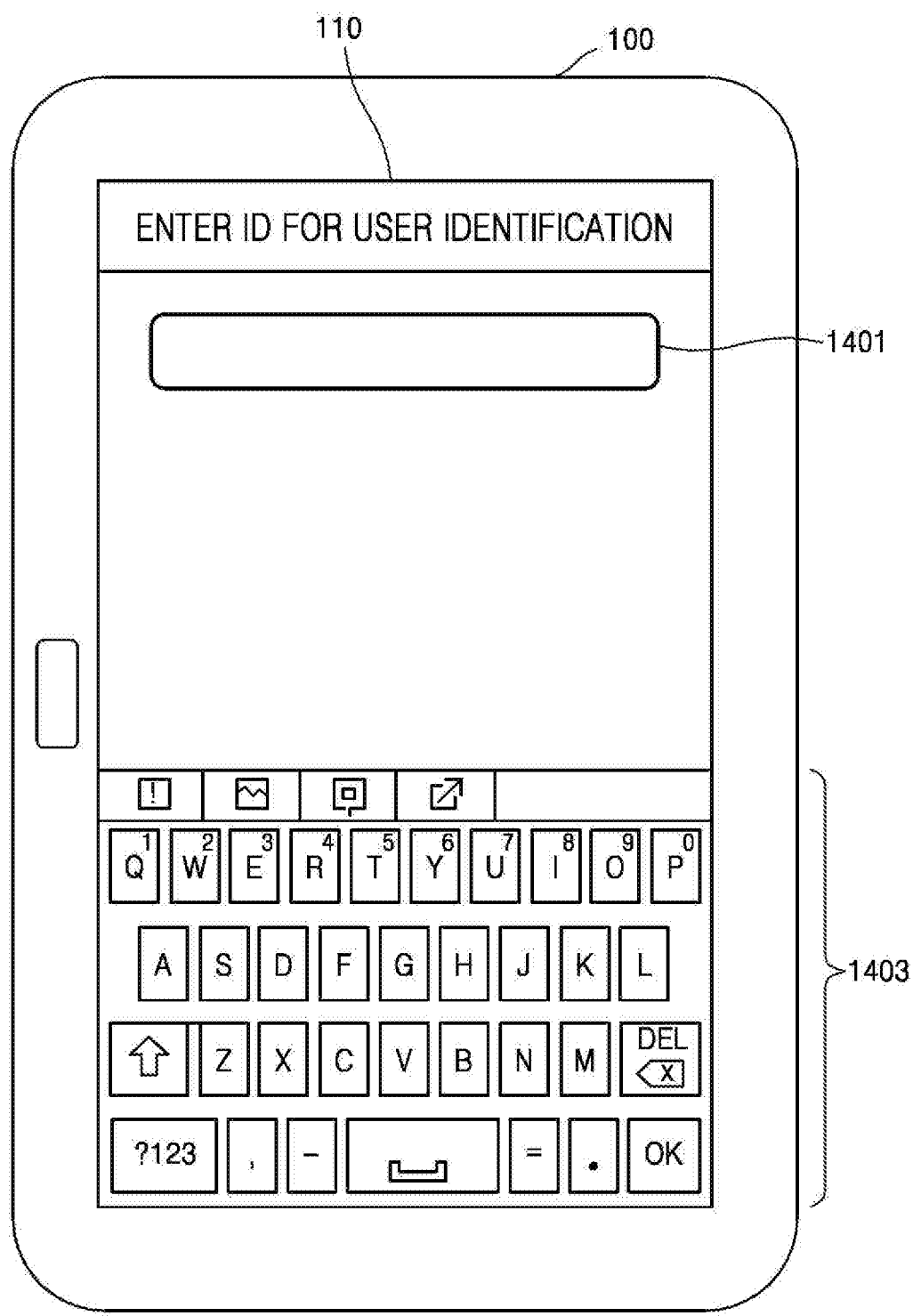
FIG. 14, FIG. 15 and FIG. 16 are diagrams for explaining a method of receiving, by a medical image display apparatus, various pieces of user ID information according to an exemplary embodiment.
Figure 15:
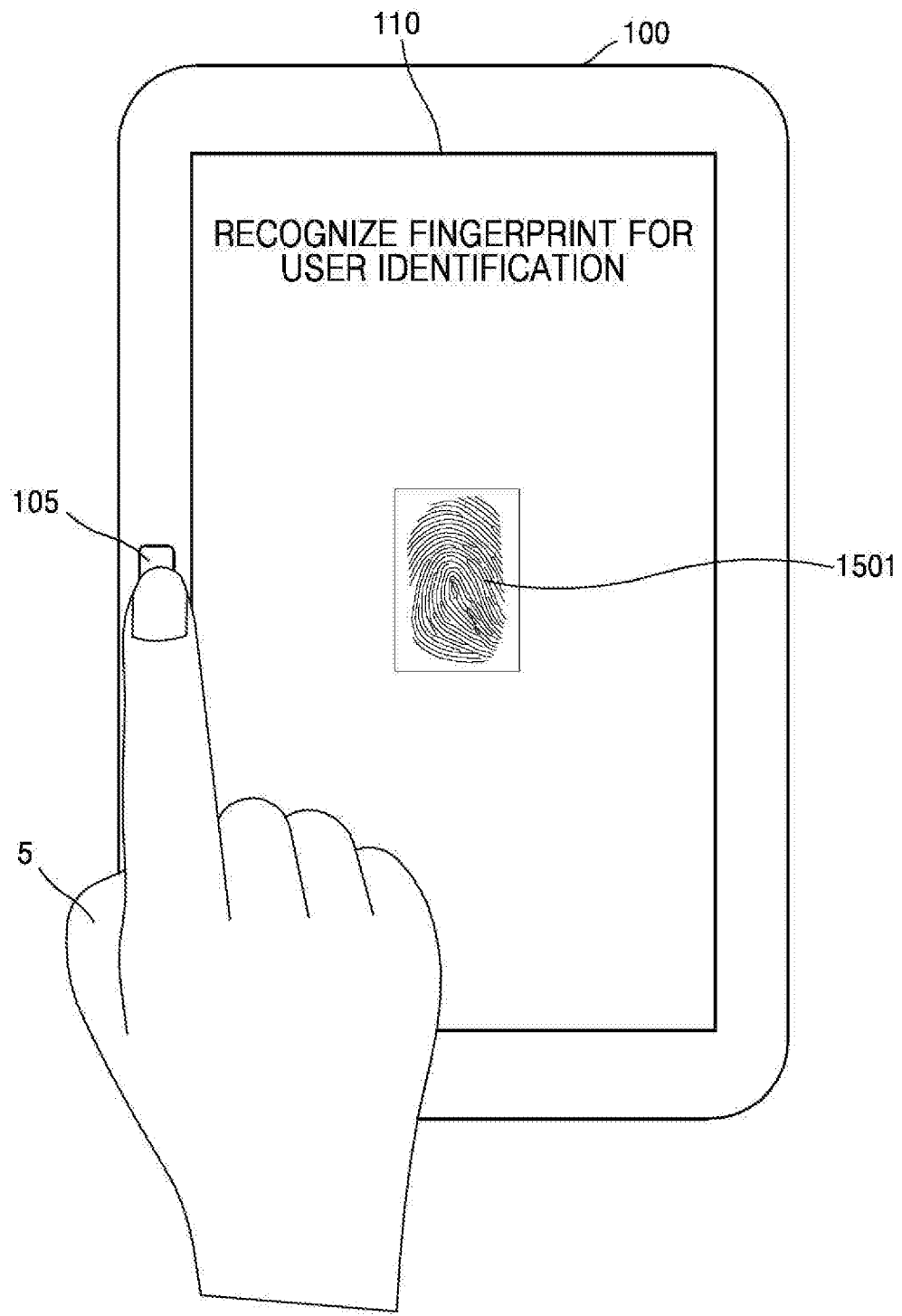
Figure 16:
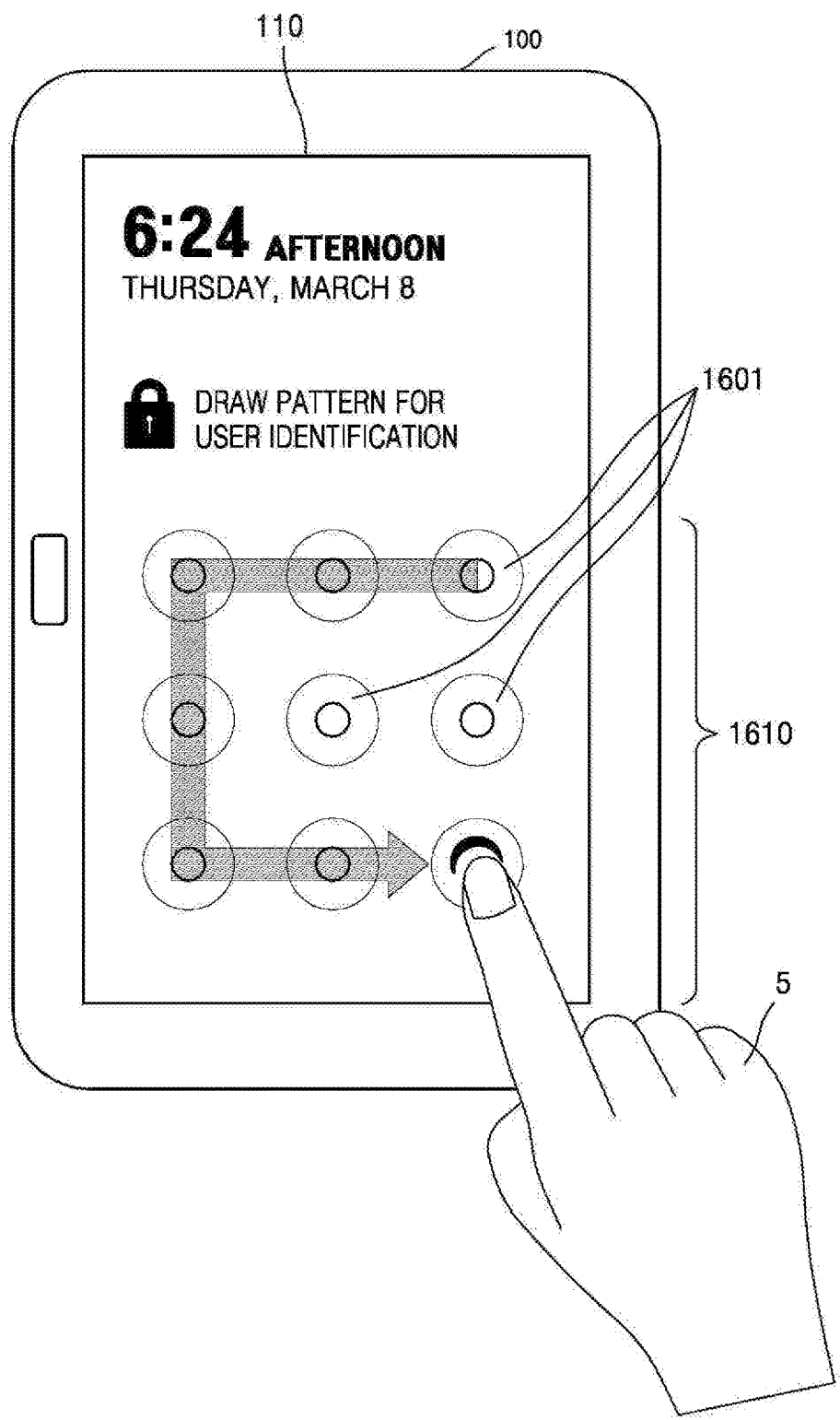

FIGS. 14 through 16 are diagrams for explaining methods of receiving, by a medical image display apparatus 100, various pieces of ID information of a user, according to an exemplary embodiment.

As shown in FIG. 14, the medical image display apparatus 100 may receive an ID for user identification from a user. The medical image display apparatus 100 may receive an ID for user identification based on a user input for selecting at least one key included in a virtual keyboard 1403 displayed on a touch screen 110. The ID input by the user via the virtual keyboard 1403 may be displayed in an ID entry region 1401.

In some exemplary embodiments, as shown in FIG. 15, the medical image display apparatus 100 may receive fingerprint information for user identification from a user 5. The medical image display apparatus 100 may detect a fingerprint in a finger located on a fingerprint recognition unit 105 provided in the medical image display apparatus 100. The detected fingerprint may be displayed in a fingerprint display region 1501.

As shown in FIG. 16, the medical image display apparatus 100 may receive a pattern for user identification from a user 5. The medical image display apparatus 100 may receive a pattern for user identification based on a user input performed by drawing a pattern that connects a plurality of dots among dots 1601 included in a pattern input region 1610. The medical image display apparatus 100 may display in the pattern input region 1610 a path along which the user 5 draws the pattern by connecting a plurality of dots.

Exemplary embodiments are not limited to the methods of receiving pieces of ID information shown in FIGS. 14 through 16. The medical image display apparatus 100 may receive various pieces of ID information of a user in various other ways.

The medical image display apparatus 100 may acquire information about the first region corresponding to the ID information of the user from a memory (S1330). The medical image display apparatus 100 may acquire the information about the first region by reading out information about a touch range corresponding to the received user ID information of the user from the memory. The medical image display apparatus 100 may acquire the information about the first region from a memory included in the medical image display apparatus 100, a memory of an external device, and an external server.

In addition, the medical image display apparatus 100 may acquire information about a first region by analyzing a touch gesture received from a user.

Figure 17:
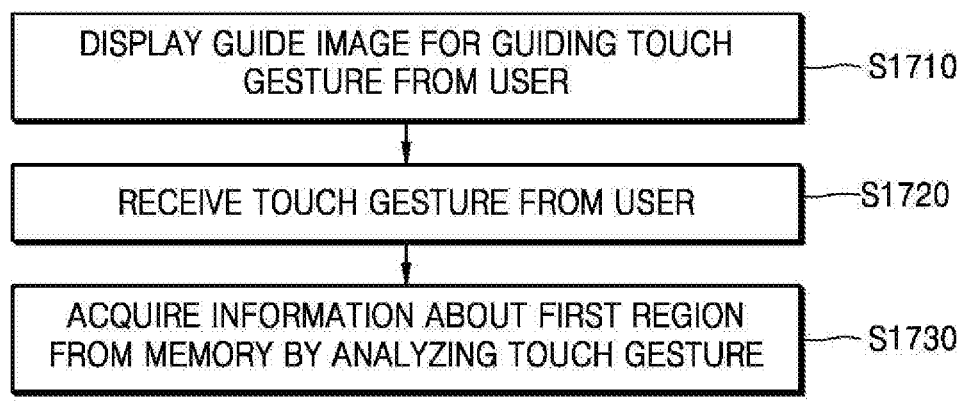
FIG. 17 is a flowchart of a method of acquiring, by a medical image display apparatus, information about a first region based on a user's touch gesture.

FIG. 17 is a flowchart of a method of acquiring, by the medical image display apparatus 100, information about a first region based on a touch gesture received from a user.

The medical image display apparatus 100 may display a guide image for guiding a touch gesture from a user (S1710).

When it is determined that the user is holding and using the medical image display apparatus 100 and if a posture of a hand of the user used to grip the medical image display apparatus 100 or the user himself/herself is changed, the medical image display apparatus 100 may display a guide image.

The medical image display apparatus 100 may display a guide image for guiding a touch gesture from a finger of a user's hand used to grip the medical image display apparatus 100.

Figure 18:
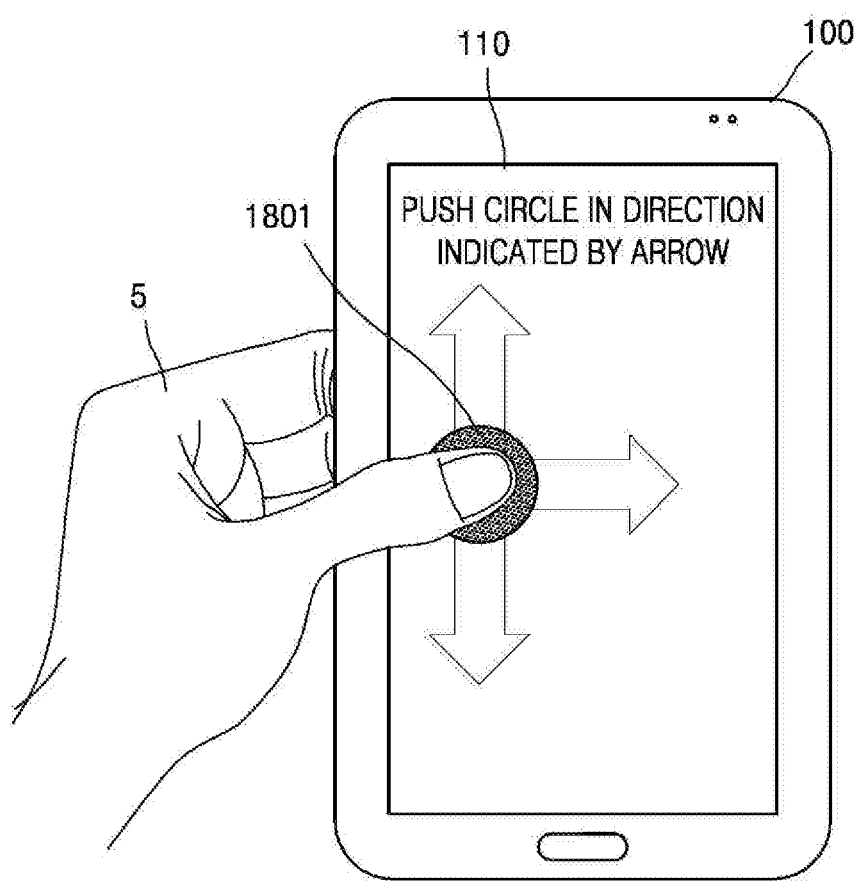
FIG. 18 illustrates an example of a guide image displayed by a medical image display apparatus to guide a touch gesture from a user, according to an exemplary embodiment.
Figure 22A:
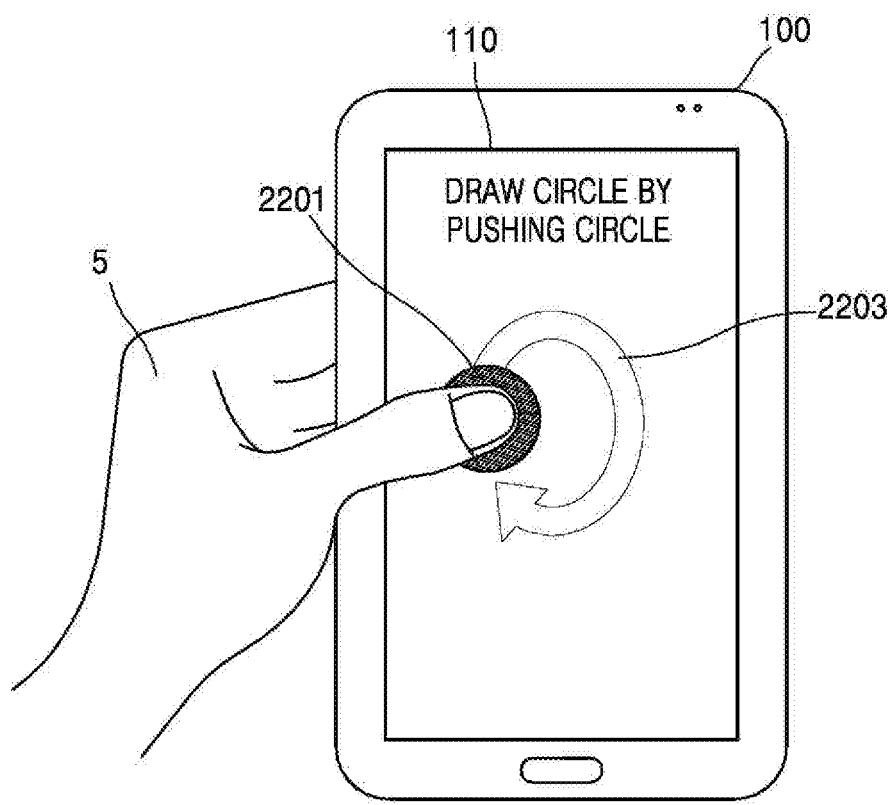
FIG. 22A illustrates an example of a guide image displayed by a medical image display apparatus to guide a touch gesture from a user, according to an exemplary embodiment.

For example, as shown in FIG. 18 or 22A, the medical image display apparatus 100 may display a guide image for guiding a user's swipe touch or touch of a finger moving along a certain path.

The medical image display apparatus 100 may receive a touch gesture from the user (S1720).

The medical image display apparatus 100 may receive a touch gesture from a finger of a user's hand used to grip the medical image display apparatus 100.

Examples of a user's touch gesture may include tap, touch and hold, double tap, drag, panning, flick, drag and drop, pinch, swipe, or any other desired gesture.

The medical image display apparatus 100 may determine whether the touch gesture received from the user is the touch gesture corresponding to the guide image displayed in operation S1710.

For example, the medical image display apparatus 100 may determine whether a swipe touch for moving a finger along a certain direction indicated in the guide image has been received from the user. In some exemplary embodiments, the medical image display apparatus 100 may determine whether a touch gesture involving moving a finger along a certain path indicated in the guide image has been received from the user.

The medical image display apparatus 100 may calculate a degree of similarity between the touch gesture received from the user and a prestored reference touch gesture corresponding to the guide image and determine whether the touch gesture received from the user is the touch gesture corresponding to the guide image based on the calculated degree of similarity therebetween.

The medical image display apparatus 100 may acquire information about a first region by analyzing the touch gesture received from the user (S1730). If it is determined that the touch gesture received from the user is the touch gesture corresponding to the guide image, the medical image display apparatus 100 may acquire the information about the first region based on the received touch gesture.

The medical image display apparatus 100 may acquire, as the information about the first region, information about at least one of a maximum finger-touchable distance, a maximum finger-touchable angle, a maximum area of a finger-touchable region, and a shape of the region.

FIG. 18 illustrates an example of a guide image displayed by a medical image display apparatus 100 to guide a user's touch gesture, according to an exemplary embodiment.

As shown in FIG. 18, the medical image display apparatus 100 may display a guide image for guiding a swipe touch from a user 5.

The medical image display apparatus 100 may display an entity 1801 for guiding a swipe touch in which the user 5 touches the entity 1801 via a finger and moves the finger to another location while still maintaining the touch). The medical image display apparatus 100 may receive the swipe touch for moving the entity 1801 along a direction indicated by an arrow.

The medical image display apparatus 100 may analyze the swipe touch received from the user 5 and acquire, based on an analysis result, a maximum finger-touchable distance as information about a first region.

For example, based on the swipe touch, the medical image display apparatus 100 may determine a distance by which the entity 1801 moves as a maximum finger-touchable distance. In some exemplary embodiments, the medical image display apparatus 100 may determine a distance between a reference point and a point where a speed of the swipe touch corresponds to a threshold speed as a maximum finger-touchable distance. In this case, the reference point may correspond to an initial position at which the entity 1801 is displayed.

Figure 19:
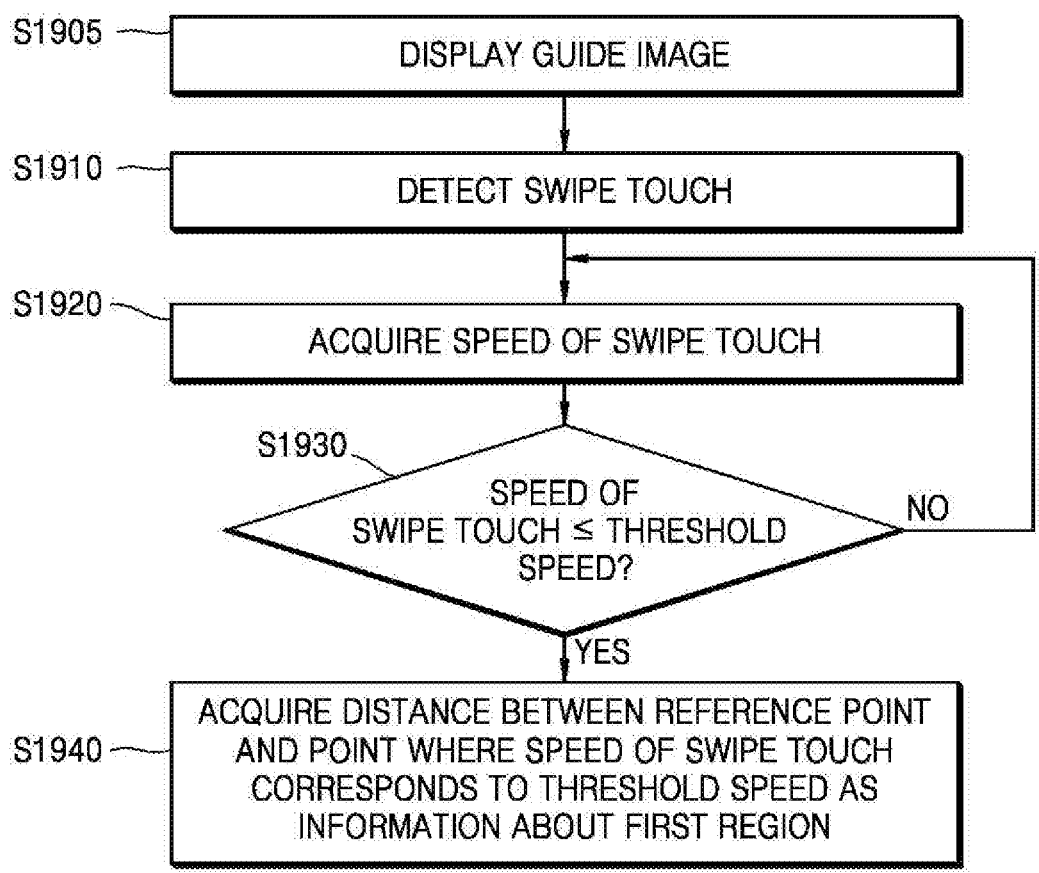
FIG. 19 is a flowchart of a method of acquiring, by a medical image display apparatus, a maximum finger-touchable distance based on a speed of a swipe touch, according to an exemplary embodiment.

FIG. 19 is a flowchart of a method of acquiring, by the medical image display apparatus 100, a maximum finger-touchable distance based on a speed at which a swipe touch moves (which may be referred to as a "swipe touch speed" or a "speed of swipe touch"), according to an exemplary embodiment.

The medical image display apparatus 100 may compare a speed of swipe touch received from the user with a threshold speed and determine, based on a comparison result, a distance between a "reference point" and a "point where the speed of the swipe touch corresponds to the threshold speed" as a maximum finger-touchable distance.

The medical image display apparatus 100 may display a guide image for guiding a swipe touch (S1905). The medical image display apparatus 100 may then detect the swipe touch corresponding to the guide image (S1910) and acquire a speed of the swipe touch (S1920).

The medical image display apparatus 100 may determine whether the speed of the swipe touch is less than a threshold speed (S1930). The threshold speed may be predetermined as a default value or may be set by the user. When the speed of the swipe touch is greater than the threshold speed, the medical image display apparatus 100 returns to operation S1920 and repeats operations of acquiring a speed of the swipe touch and comparing the speed of the swipe touch to the threshold speed.

When the speed of the swipe touch is less than or equal to the threshold speed, the medical image display apparatus 100 may acquire a distance between a reference point and a point where the speed of the swipe touch corresponds to the threshold speed as information about a first region (S1940).

The reference point may be predetermined as a default value or may be set by the user. In some exemplary embodiments, the medical image display apparatus 100 may detect a position of a hand of the user used to grip the medical image display apparatus 100 and determine the reference point based on the position of the hand of the user. In addition, the medical image display apparatus 100 may determine an initial position of the entity 1801 for guiding a swipe touch from the user as the reference point.

The point where the speed of the swipe touch corresponds to the threshold speed may be a point on the touch screen 110 that the user's finger touches when the speed of the swipe touch is determined to be less than or equal to the threshold speed.

Figure 20:
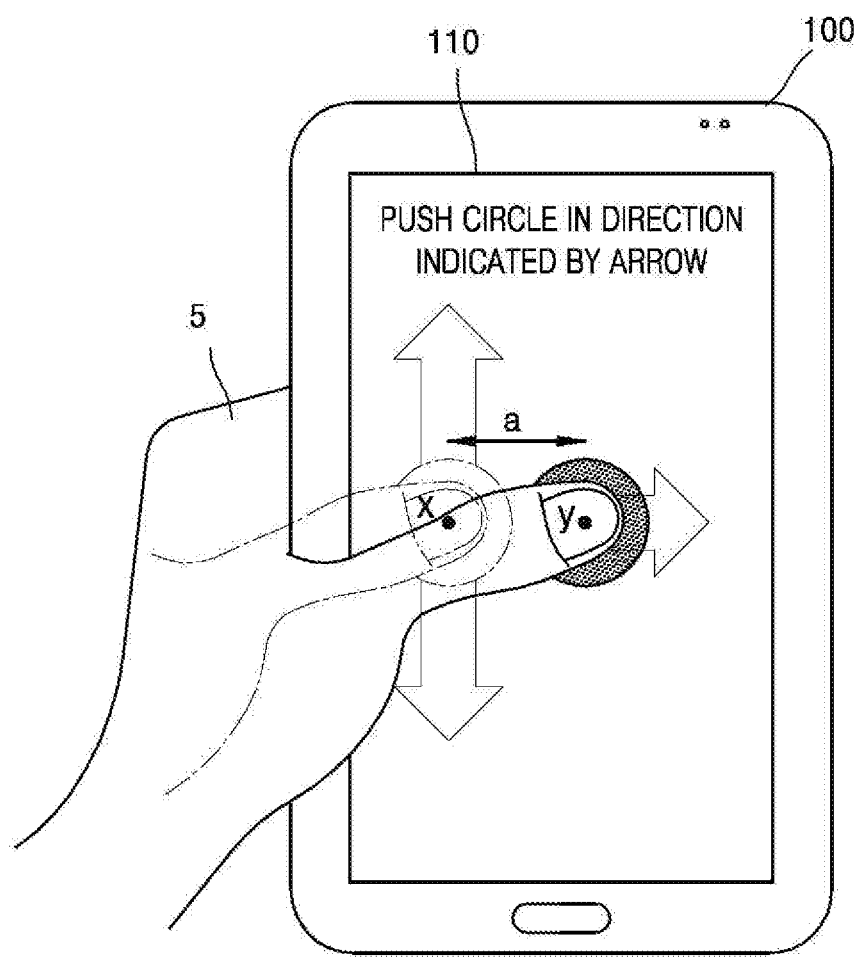
FIG. 20 and FIG. 21 are diagrams for explaining a method of acquiring, by a medical image display apparatus, a maximum finger-touchable distance as information about a first region, according to an exemplary embodiment.
Figure 21:
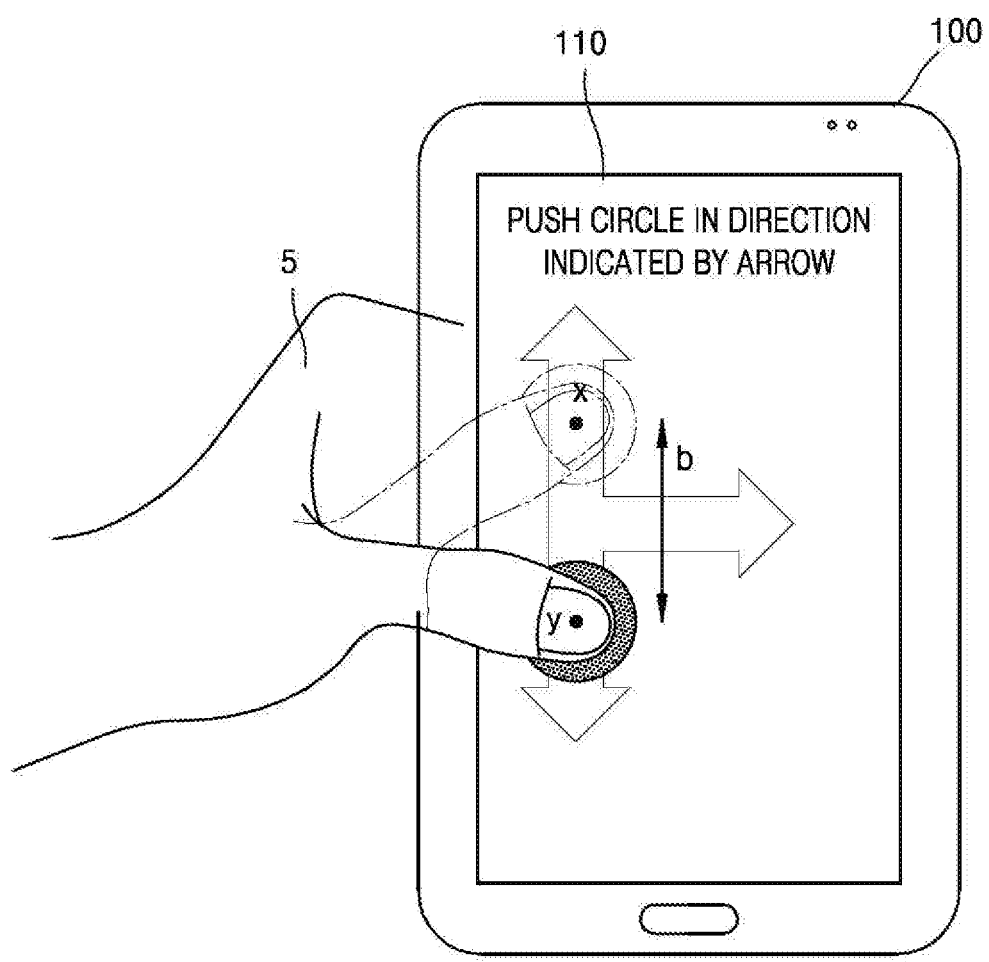

FIGS. 20 and 21 are diagrams for explaining a method of acquiring, by a medical image display apparatus 100, a maximum finger-touchable distance as information about a first region, according to an exemplary embodiment.

As shown in FIG. 20, the medical image display apparatus 100 may analyze a swipe touch in which the user 5 touches the entity 1801 of FIG. 18 and then moves the entity 1801 to another location while still maintaining touch contact with the entity 1801 and acquire information about the first region based on an analysis result. The medical image display apparatus 100 may determine a distance between a reference point x corresponding to an initial position where the entity 1801 is displayed and a point y where a speed of the swipe touch corresponds to a threshold speed as a maximum finger-touchable distance. The medical image display apparatus 100 may acquire the maximum finger-touchable distance as the information about the first region.

As shown in FIG. 21, the medical image display apparatus 100 may determine a distance between a first point x where a speed of a swipe touch for moving the entity 1801 in a first direction corresponds to a threshold speed and a second point y where a speed of a swipe touch for moving the entity 1801 in a second direction corresponds to a threshold speed as a maximum finger-touchable distance. The first direction may be opposite to the second direction. The medical image display apparatus 100 may acquire the maximum finger-touchable distance as the information about the first region.

FIG. 22A illustrates an example of a guide image displayed by a medical image display apparatus 100 to guide a touch gesture from a user 5, according to an exemplary embodiment.

The medical image display apparatus 100 may display a guide image for guiding an input of a predetermined touch gesture by the user 5. For example, the medical image display apparatus 100 may display a guide image for guiding an input of a touch gesture in which the user 5 touches a touch screen 110 with a finger and moves the finger to another location without lifting the finger off the touch screen 110.

Referring to FIG. 22A, the medical image display apparatus 100 may display an entity 2201 for guiding a touch gesture in which the user 5 touches the entity 2201 with a finger and moves the finger to another location along a certain path 2203 without lifting the finger. The medical image display apparatus 100 may receive a touch gesture involving moving the entity 2201 along the path 2203 indicated by an arrow.

The medical image display apparatus 100 may analyze the touch gesture received from the user 5 and acquire at least one of a maximum finger-touchable angle, a maximum area of a finger-touchable region, and a shape of the region as information about a first region.

For example, the medical image display apparatus 100 may extract an arc from a path along which the entity 2201 has moved based on the touch gesture and determine a central angle of a circular sector corresponding to the extracted arc as a maximum finger-touchable angle. In this case, the medical image display apparatus 100 may extract an arc of a circular sector with a reference point at a center from the path.

In some exemplary embodiments, the medical image display apparatus 100 may determine an area of a region, which includes a path along which the entity 2201 has moved based on the touch gesture as a contour, as a maximum area of a finger-touchable region.

In some exemplary embodiments, the medical image display apparatus 100 may acquire a shape of a region including a path along which the entity 2201 has moved based on the touch gesture as a contour as information about the first region.

The medical image display apparatus 100 may determine whether a touch gesture received from the user is a touch gesture corresponding to a guide image. The medical image display apparatus 100 may compare a path of movement of a finger determined based on the touch gesture received from the user with a predetermined path indicated in the guide image and determine whether the received touch gesture is the touch gesture corresponding to the guide image based on a comparison result. If the received touch gesture is determined to be the touch gesture corresponding to the guide image, the medical image display apparatus 100 may determine a finger-touchable range by analyzing the received touch gesture. Otherwise, if the received touch gesture is not determined to be the touch gesture corresponding to the guide image, the medical image display apparatus 100 may display a guide image for guiding re-input of a touch gesture by the user.

Figure 22B:
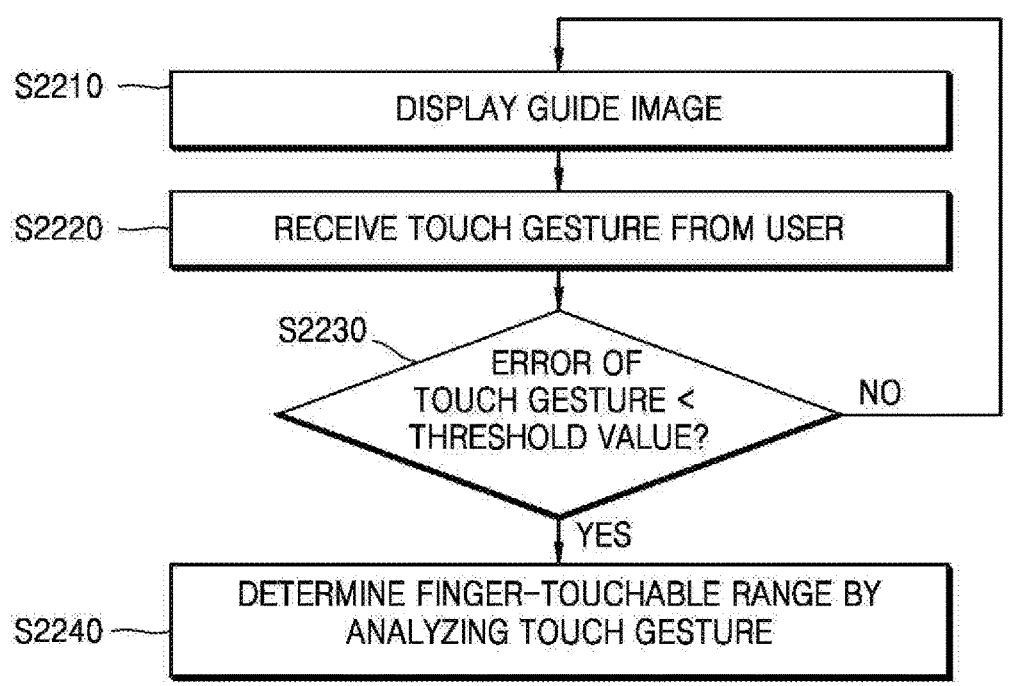
FIG. 22B is a flowchart of a method of determining, by a medical image display apparatus, a finger-touchable range by comparing a guide image with a user's touch gesture, according to an exemplary embodiment.

FIG. 22B is a flowchart of a method of determining, by the medical image display apparatus 100, a finger-touchable range by comparing a guide image with a touch gesture received from a user, according to an exemplary embodiment.

The medical image display apparatus 100 may display a guide image for guiding a touch gesture from a user (S2210). For example, as shown in FIG. 22A, the guide image may include the entity 2201 and the path 2203 to elicit a touch gesture involving moving the entity 2201 along the path 2203

The medical image display apparatus 100 may receive a touch gesture from the user (S2220). For example, the medical image display apparatus 100 may receive a touch gesture in which the user touches the touch screen 110 with a finger and moves the finger to another location along a certain path included in the guide image while still touching the touch screen 110

The medical image display apparatus 100 may compare an error of the touch gesture received from the user to a threshold value (S2230). The medical image display apparatus 100 may determine whether the received touch gesture is a touch gesture corresponding to the guide image based on a comparison result.

The error of the touch gesture received from the user may mean a difference between a path of movement of a finger determined based on the received touch gesture and a predetermined path included in the guide image. For example, the error of the touch gesture received from the user may be determined based on a degree of similarity between the path of movement of the finger and the predetermined path included in the guide image.

If the error of the received touch gesture is greater than or equal to the threshold value, the medical image display apparatus 100 may determine that the received touch gesture is not a touch gesture corresponding to the guide image. In this case, the medical image display apparatus 100 may return to operation S2210 and receive again a touch gesture from the user. The medical image display apparatus 100 may repeat operations S2210 through S2230 until receiving a touch gesture corresponding to the guide image.

If the error of the received touch gesture is less than the threshold value, the medical image display apparatus 100 may determine a finger-touchable range by analyzing the received touch gesture (S2240). The medical image display apparatus 100 may analyze the received touch gesture and acquire, based on an analysis result, at least one of a maximum finger-touchable angle, a maximum area of a finger-touchable region, and a shape of the region as information about a first region.

Figure 23:
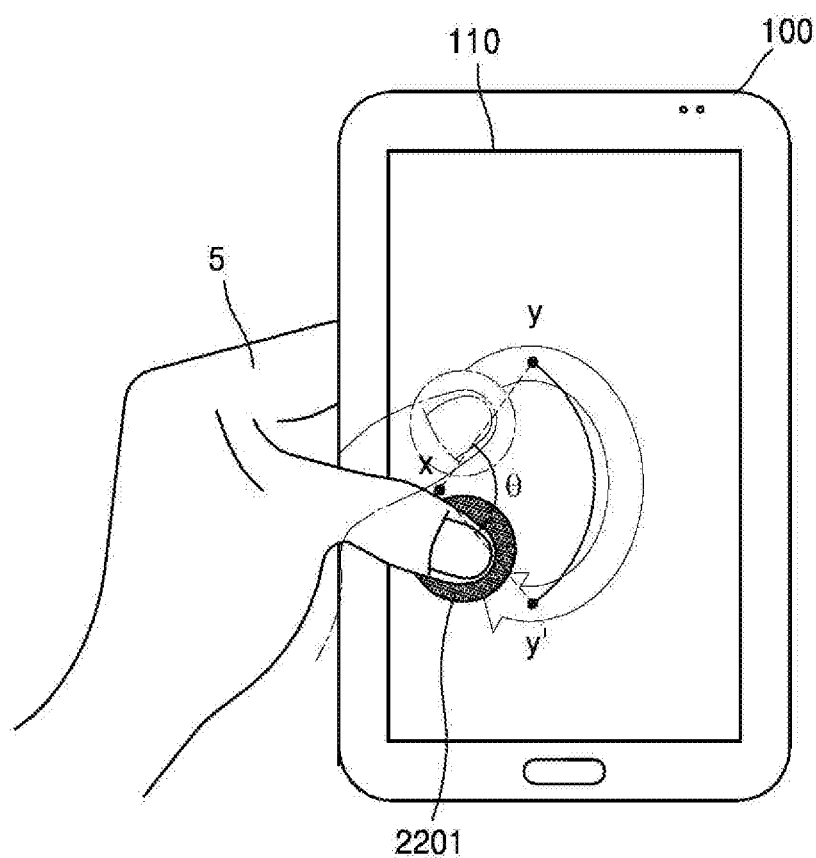
FIG. 23 is a diagram for explaining a method of acquiring, by a medical image display apparatus, a maximum finger-touchable angle as information about a first region, according to an exemplary embodiment.

FIG. 23 is a diagram for explaining a method of acquiring, by a medical image display apparatus 100, a maximum finger-touchable angle as information about a first region, according to an exemplary embodiment.

Referring to FIG. 23, the medical image display apparatus 100 may analyze a touch gesture in which the user 5 touches an entity 2201 and moves the entity 2201 to another location while maintaining a touch on the entity 2201, and may acquire information about a first region. The medical image display apparatus 100 may extract an arc yy' from a path along which the entity 2201 has moved and determine a central angle θ of a circular sector corresponding to the arc yy' as a maximum finger-touchable angle.

Figure 24:
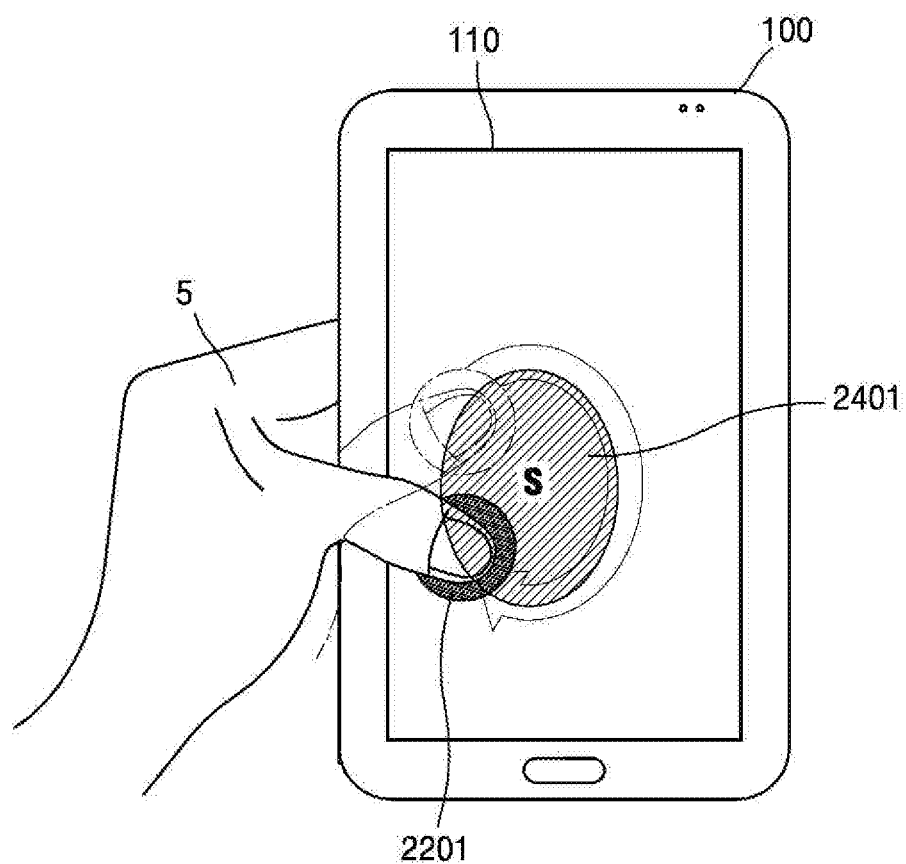
FIG. 24 is a diagram for explaining a method of acquiring, by a medical image display apparatus, a maximum area of a finger-touchable region as information about a first region, according to an exemplary embodiment.

FIG. 24 is a diagram for explaining a method of acquiring, by a medical image display apparatus 100, a maximum area of a region that may be touched by a finger of a user 5 as information about a first region, according to an exemplary embodiment.

As shown in FIG. 24, the medical image display apparatus 100 may analyze a touch gesture in which the user 5 touches an entity 2201 and moves the entity 2201 to another location while still touching the entity 2201 and acquire information about a first region based on an analysis result. The medical image display apparatus 100 may determine a region 2401 including a path along which the entity 2201 has moved as a contour and then an area S of the determined region 2401 as a maximum area of a region that may be touched by a finger of the user 5.

In addition, according to an exemplary embodiment, the medical image display apparatus 100 may receive information about the first region directly from a user. In detail, the medical image display apparatus 100 may display a UI for receiving information about the first region and acquire a user input received from the user as the information about the first region.

Figure 25:
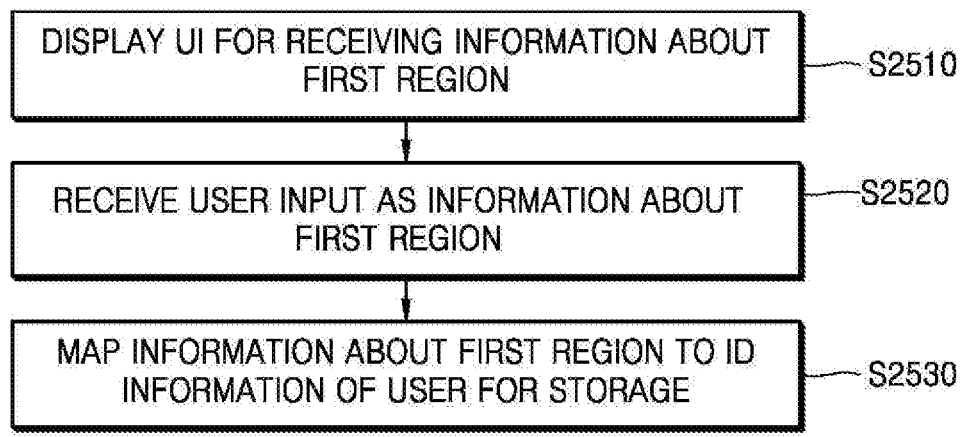
FIG. 25 is a flowchart of a method of acquiring, by a medical image display apparatus, a user input as information about a first region, according to an exemplary embodiment.

FIG. 25 is a flowchart of a method of acquiring, by the medical image display apparatus 100, a user input as information about a first region, according to an exemplary embodiment.

The medical image display apparatus 100 may display a UI for receiving information about a first region (S2510).

In detail, when it is determined that a user is holding and using the medical image display apparatus 100 and if a posture of a hand of the user used to grip the medical image display apparatus 100 or the user himself/herself is changed, the medical image display apparatus 100 may receive a UI for receiving information about the first region.

In some exemplary embodiments, the medical image display apparatus 100 may display a UI for receiving information about the first region based on a user input.

The medical image display apparatus 100 may receive a user input as the information about the first region (S2520). For example, the medical image display apparatus 10 may receive from the user at least one of a length of a user's finger, a maximum finger-touchable distance in a transverse direction, a maximum finger-touchable distance in a longitudinal direction, and a maximum finger-touchable angle.

The medical image display apparatus 100 may map the information about the first region to ID information of the user storage (S2530).

The medical image display apparatus 100 may receive ID information of a first user from the first user. In some exemplary embodiments, the medical image display apparatus 100 may receive ID information of the first user via a predetermined operation performed by the first user. For example, the predetermined operation may include bringing an ID card containing the ID information of the first user close to or into contact with the medical image display apparatus 100, or otherwise providing the ID card, or entering a first user's name or ID via the medical image display apparatus 100, etc.

Figure 26:
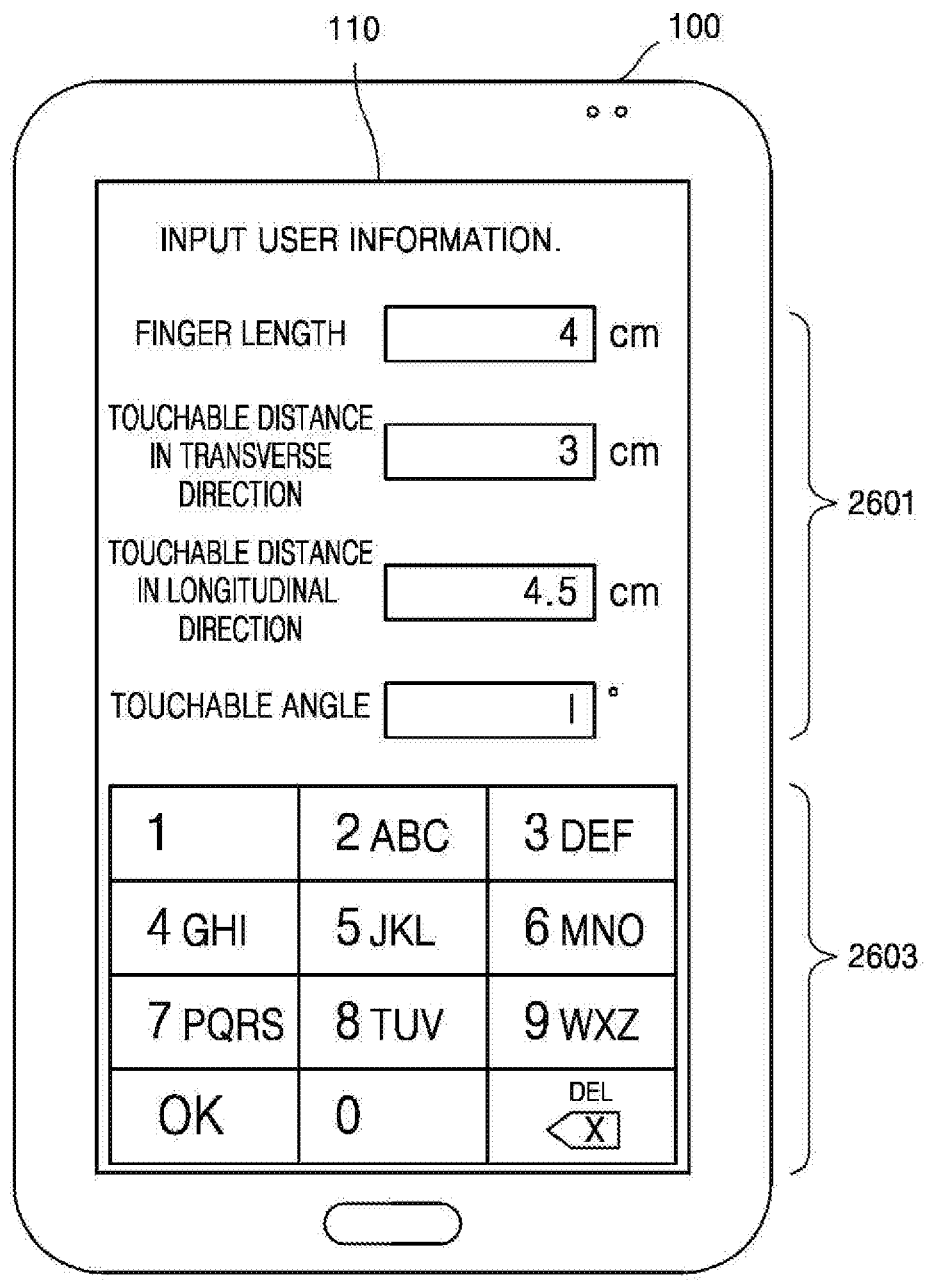
FIG. 26 illustrates an example of a UI for receiving information about a first region and which is displayed by a medical image display apparatus, according to an exemplary embodiment.

FIG. 26 illustrates an example of a UI for receiving information about a first region and which is displayed by a medical image display apparatus 100, according to an exemplary embodiment.

Referring to FIG. 26, the medical image display apparatus 100 may receive information about a first region for defining a finger-touchable range from the user. The medical image display apparatus 100 may receive the information about the first region based on a user input for selecting at least one key included in a keypad 2603 displayed on a touch screen 110. The information about the first region input by the user via the keypad 2603 may be displayed in an information input region 2601.

As shown in FIG. 26, the medical image display apparatus 100 may receive from the user at least one of a length of a finger, a maximum finger-touchable distance r in a transverse direction, a maximum finger-touchable distance in a longitudinal direction, and a maximum finger-touchable angle.

Exemplary methods of acquiring, by the medical image display apparatus 100, information about the first region according to various exemplary embodiments have been described above with reference to FIGS. 9A through 26. According to various exemplary embodiments, after acquiring information about the first region, the medical image display apparatus 100 may select a UI corresponding to a size of the first region based on the acquired information about the first region. For example, the medical image display apparatus 100 may select a UI corresponding to a size of the first region from among a plurality of UIs, based on a result of comparing the size of the first region to at least one threshold value.

By selecting a UI corresponding to a size of the first region, the medical image display apparatus 100 may provide a user with a UI suitable for a finger-touchable range. As the touch range of the user's finger increases (i.e., as the first region increases in size), the medical image display apparatus 100 may select a UI that occupies a greater area on the touch screen 110

Furthermore, the medical image display apparatus 100 may select a UI configured to receive a touch gesture suitable according to a size of the first region, from among a plurality of UIs.

A size of a region on a touch screen that the user may use to input a touch gesture may vary depending on the type of a touch gesture. Thus, an area on the touch screen 110 occupied by each of a plurality of UIs may vary according to which type of touch gesture a UI is configured to receive.

Thus, the medical image display apparatus 100 may select a type of touch gesture corresponding to a size of the first region from among different types of touch gestures and then a UI configured to receive the selected touch gesture.

For example, when the user inputs touch gestures involving moving a finger or touch instrument, such as drag, panning, flick, and swipe touch gestures, the user may use a greater region on a touch screen than when he or she inputs a tap, touch and hold, or double tap touch gesture. Thus, if the first region has a large size, the medical image display apparatus 100 may select a UI configured to receive at least one of drag, panning, flick, and swipe touch gestures. Otherwise, if the first region has a small size, the medical image display apparatus 100 may select a UI configured to receive at least one of tap, touch and hold, and double tap touch gestures.

Furthermore, the medical image display apparatus 100 may select a UI having an operation depth suitable according to a size of the first region from among a plurality of UIs. An operation depth of a UI may mean a range of functions of the medical image display apparatus 100 that may be used by the user via the UI. As an operation depth of a UI decreases, the user may use fewer functions of the medical image display apparatus 100. As an operation depth of a UI increases, the user may use more functions of the medical image display apparatus 100.

An area on the touch screen 110 occupied by each of a plurality of UIs may vary according to the number of functions corresponding to icons included in a UI. Thus, as a size of the first region increases, the medical image display apparatus 100 may select a UI providing more functions. As the size of the first region decreases, the medical image display apparatus 100 may select a UI providing fewer functions.

The number of functions selected by the medical image display apparatus 100 from among all functions provided by the medical image display apparatus 100 in relation to a medical image, may correspond to a size of the first region. The medical image display apparatus 100 may then select a UI including at least one icon corresponding to the selected functions.

Figure 27:
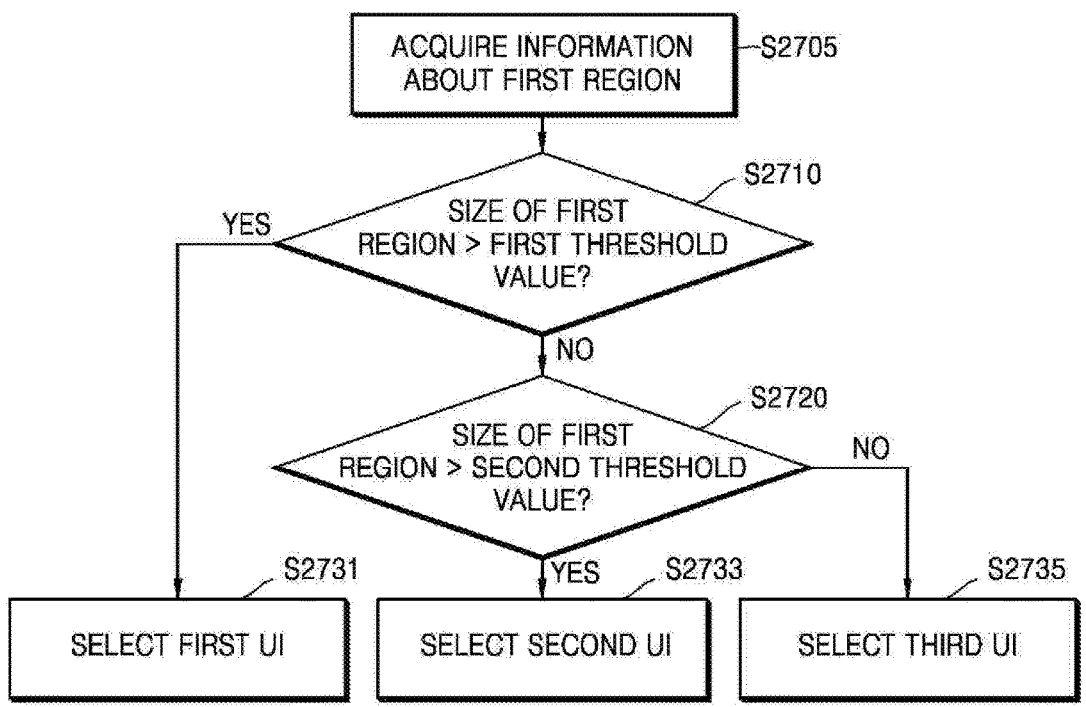
FIG. 27 is a flowchart of a method of selecting, by a medical image display apparatus, a UI based on a result of comparing a size of a first region with a threshold value, according to an exemplary embodiment.

FIG. 27 is a flowchart of a method of selecting, by the medical image display apparatus 100, a UI based on a result of comparing a size of a first region with a threshold value, according to an exemplary embodiment.

Operation S2705 illustrated in FIG. 27 may correspond to operation S510 illustrated in FIG. 5 and operations S2710, S2720, S2731, S2733, and S2735 may, in some exemplary embodiments, be included in operation S520 illustrated in FIG. 5. Thus, the same descriptions as provided above with respect to FIG. 5 will be omitted here.

The medical image display apparatus 100 may acquire information about a first region (S2705).

The medical image display apparatus 100 may acquire the information about the first region from a memory included in the medical image display apparatus 100, a memory of an external device, or an external server. In some exemplary embodiments, the medical image display apparatus 100 may acquire the information about the first region by analyzing a touch gesture received from the user in response to a guide image. In addition, the medical image display apparatus 100 may receive the information about the first region directly from the user.

The medical image display apparatus 100 may compare a size of the first region to a first threshold value (S2710). The first threshold value may be predetermined as a default value or may be set by the user. For example, the first threshold value may be a value corresponding to a size of a first UI.

If the size of the first region is greater than the first threshold value, the medical image display apparatus 100 may select a first UI from among a plurality of UIs (S2731).

If the size of the first region is less than or equal to the first threshold value, the medical image display apparatus 100 may compare the size of the first region to a second threshold value (S2720). In some exemplary embodiments, the second threshold value may be less than the first threshold value. The second threshold value may be predetermined as a default value or may be set by the user. For example, the second threshold value may be a value corresponding to a size of a second UI.

If the size of the first region is greater than the second threshold value, the medical image display apparatus 100 may select a second UI from among the plurality of UIs (S2733). Otherwise, if the size of the first region is less than or equal to the second threshold value, the medical image display apparatus 100 may select a third UI from among the plurality of UIs (S2735).

The medical image display apparatus 100 may display a selected UI within a touch range of the user's finger.

Figure 28:
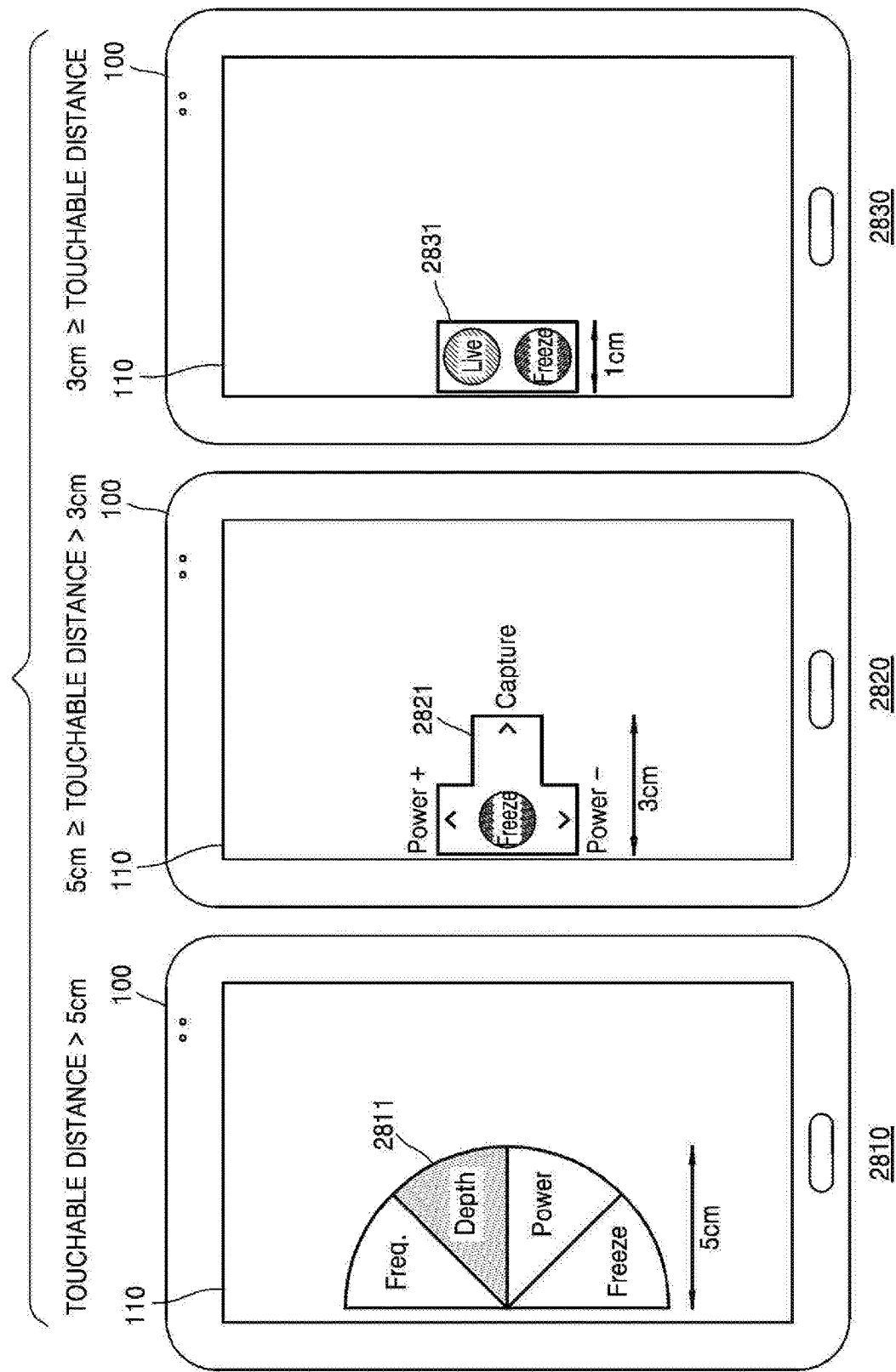
FIG. 28 illustrates examples of UIs selected by a medical image display apparatus based on a result of comparing a size of a first region with a threshold value, according to an exemplary embodiment.

FIG. 28 illustrates examples of a plurality of first through third UIs 2811, 2821, and 2831 selected by a medical image display apparatus 100 based on a result of comparing a size of a first region with a threshold value, according to an exemplary embodiment.

Referring to FIG. 28, the medical image display apparatus 100 acquires a maximum finger-touchable distance as information about the first region. In other words, the medical image display apparatus 100 may acquire the maximum finger-touchable distance as a value indicative of a size of the first region.

The medical image display apparatus 100 may compare the maximum finger-touchable distance to a first threshold value of 5 cm. If the maximum finger-touchable distance is greater than 5 cm, the medical image display apparatus 100 may select the first UI 2811 from among the first through third UIs 2811, 2821, and 2831. As shown in a portion 2810, when the first UI 2811 is selected, the medical image display apparatus 100 may display the selected first UI 2811 on a touch screen 110.

If the maximum finger-touchable distance is less than or equal to 5 cm, the medical image display apparatus 100 may compare the maximum finger-touchable distance to a second threshold value of 3 cm. If the maximum finger-touchable distance is less than or equal to 5 cm but is greater than 3 cm, the medical image display apparatus 100 may select the second UI 2821 from among the first through third UIs 2811, 2821, and 2831. As shown in a portion 2820, when the second UI 2821 is selected, the medical image display apparatus 100 may display the selected second UI 2821 on the touch screen 110.

If the maximum finger-touchable distance is less than or equal to 3 cm, the medical image display apparatus 100 may select the third UI 2832 from among the first through third UIs 2811, 2821, and 2831. As shown in a portion 2830, when the third UI 2831 is selected, the medical image display apparatus 100 may display the selected third UI 2831 on the touch screen 110.

As shown in FIG. 28, the medical image display apparatus 100 may select a type of touch gesture corresponding to the size of the first region from among different types of touch gestures and then a UI configured to receive the selected touch gesture.

For example, the first UI 2811 may be configured to receive a swipe touch and a flick touch, the second UI 2821 may be configured to receive a tap touch, touch and hold, and a flick touch, and the third UI 2831 may be configured to receive a tap touch and touch and hold.

To detect a swipe touch, the medical image display apparatus 100 may require a greater area on the touch screen 110 than to detect a flick touch, a tap touch, and touch and hold. Thus, if the first region has a large size, the medical image display apparatus 100 may select the first UI 2811 configured to receive a swipe touch and a flick touch. On the other hand, if the first region has a very small size, the medical image display apparatus 100 may select the third UI 2831 configured to receive only a tap touch and a touch and hold gesture.

Furthermore, as shown in FIG. 28, as the size of the first region increases, the medical image display apparatus 100 may select a UI providing more functions.

For example, the first UI 2811 may include icons corresponding to four (4) functions performed by the medical image display apparatus 100. In detail, the first UI 2811 may include icons corresponding to a function of adjusting frequency of an ultrasound signal transmitted by an ultrasound probe of the ultrasound diagnosis device 11 of FIG. 1, a function of adjusting a depth of penetration of an ultrasound signal, a function of adjusting intensity of an ultrasound signal, and a function of changing an operating mode of the ultrasound diagnosis device 11 from a live mode to a freeze mode.

The second UI 2821 may include icons corresponding to three (3) functions, i.e., a function of adjusting intensity of an ultrasound signal, a function of changing an operating mode of the ultrasound diagnosis device 11 from a live mode to a freeze mode, and a function of capturing an ultrasound image.

The third UI 2831 may include icons corresponding to two (2) functions, i.e., a function of changing an operating mode of the ultrasound diagnosis device 11 from a live mode to a freeze mode and a function of changing the operating mode from a freeze mode to a live mode.

When the first region has a large size, the medical image display apparatus 100 may select the first UI 2811 including icons corresponding to a large number of functions. Thus, if the first region is large in size, the user may control the medical image display apparatus 100 to perform a large number of functions by selecting the icons included in the first UI 2811. On the other hand, when the first region has a small size, the medical image display apparatus 100 may select the third UI 2831 including icons corresponding to a small number of functions. Thus, if the first region is small in size, the user may control the medical image display apparatus 100 to perform only a limited number of functions by selecting the icons included in the third UI 2831.

UIs that may be provided by the medical image display apparatus 100 according to various exemplary embodiments will now be described in detail with reference to FIGS. 29 through 43.

The medical image display apparatus 100 may provide a UI for adjusting a parameter related to a medical image. The parameter related to the medical image may include at least one piece of information from among pieces of information about numerical values that are set with respect to an operation of acquiring the medical image to be displayed via the medical image display apparatus 100, numerical values that are set with respect to an operation of displaying the acquired medical image, and numerical values related to an object depicted in the medical image.

Figure 29:
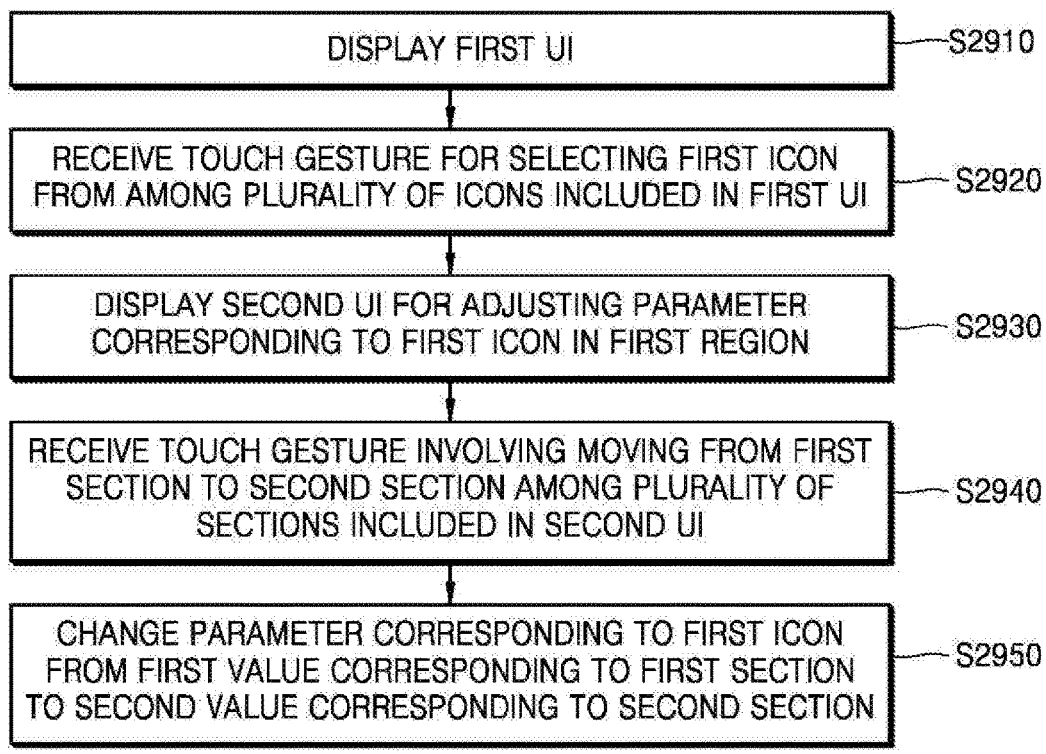
FIG. 29 is a flowchart of a method of providing, by a medical image display apparatus, a UI for adjusting a parameter according to an exemplary embodiment.

FIG. 29 is a flowchart of a method of providing, by the medical image display apparatus 100, a UI for adjusting a parameter according to an exemplary embodiment.

The medical image display apparatus 100 may display a first UI (S2910).

As illustrated in FIG. 5, the medical image display apparatus 100 may select a first UI corresponding to a size of a first region from among a plurality of UIs and display the selected first UI. The medical image display apparatus 100 may display the first UI within the first region determined as a finger-touchable region.

The first UI may include a plurality of icons that are selectable by a user. An icon may be a character or picture to represent a command for performing a function provided by the medical image display apparatus 100. For example, the first UI may include a plurality of icons representing commands for performing at least one of a function of setting a parameter related to a medical image, a function of controlling an external device or server connected to the medical image display apparatus 100, and a function of inputting information about the medical image.

The medical image display apparatus 100 may receive a touch gesture for selecting a first icon from among a plurality of icons included in the first UI (S2920).

At least one of the plurality of icons included in the first UI may represent a command for performing a function of adjusting at least one parameter related to a medical image. The plurality of icons may include the first icon related to a function of adjusting a parameter related to the medical image. To adjust the parameter, the user may input the touch gesture for selecting the first icon from among the plurality of icons.

When a predetermined touch gesture with respect to the first icon is received, the medical image display apparatus 100 may determine that a touch gesture for selecting the first icon has been received. For example, when a certain type of touch gesture is input to a region of the touch screen 110 corresponding to the first icon, the medical image display apparatus 100 may determine that a touch gesture for selecting the first icon has been received.

A type of touch gesture that the medical image display apparatus 100 is to receive from the user in order to select at least one icon from among a plurality of icons may be predetermined as a default value or may be set by the user. In some exemplary embodiments, the medical image display apparatus 100 may select a UI that is configured to receive a specific touch gesture, based on the size of the first region.

The medical image display apparatus 100 may display a second UI for adjusting a parameter corresponding to the first icon in a first region (S2930).

When the touch gesture for selecting the first icon from among the plurality of icons included in the first UI is received, the medical image display apparatus 100 may load the second UI on a touch screen. In the first region, the medical image display apparatus 100 may display the second UI instead of the first UI. The second UI may be a submenu under the first UI.

The user may adjust the parameter corresponding to the first icon via the second UI. The second UI may include a plurality of sections respectively corresponding to values that increase by a certain value along a certain direction.

The medical image display apparatus 100 may receive a touch gesture involving movement of a user's finger from a first section to a second section among a plurality of sections included in the second UI (S2940).

The second UI may include a plurality of sections respectively corresponding to a plurality of values of the parameter corresponding to the first icon. The number of sections to be included in the second UI may be predetermined as a default value or may be set by the user. As the second UI includes more sections, the user may adjust a parameter more precisely.

To set the parameter corresponding to the first icon to a certain value, the user may input a touch gesture involving moving, for example, a user's finger, to a section corresponding to the certain value. For example, the medical image display apparatus 100 may receive at least one of drag, panning, and swipe touches involving touching the first section with the user's finger and moving the user's finger to the second section.

When the touch gesture involving movement of the user's finger from the first section to the second section is received, the medical image display apparatus 100 may change the parameter corresponding to the first icon from a first value corresponding to the first section to a second value corresponding to the second section (S2950).

Figure 30:
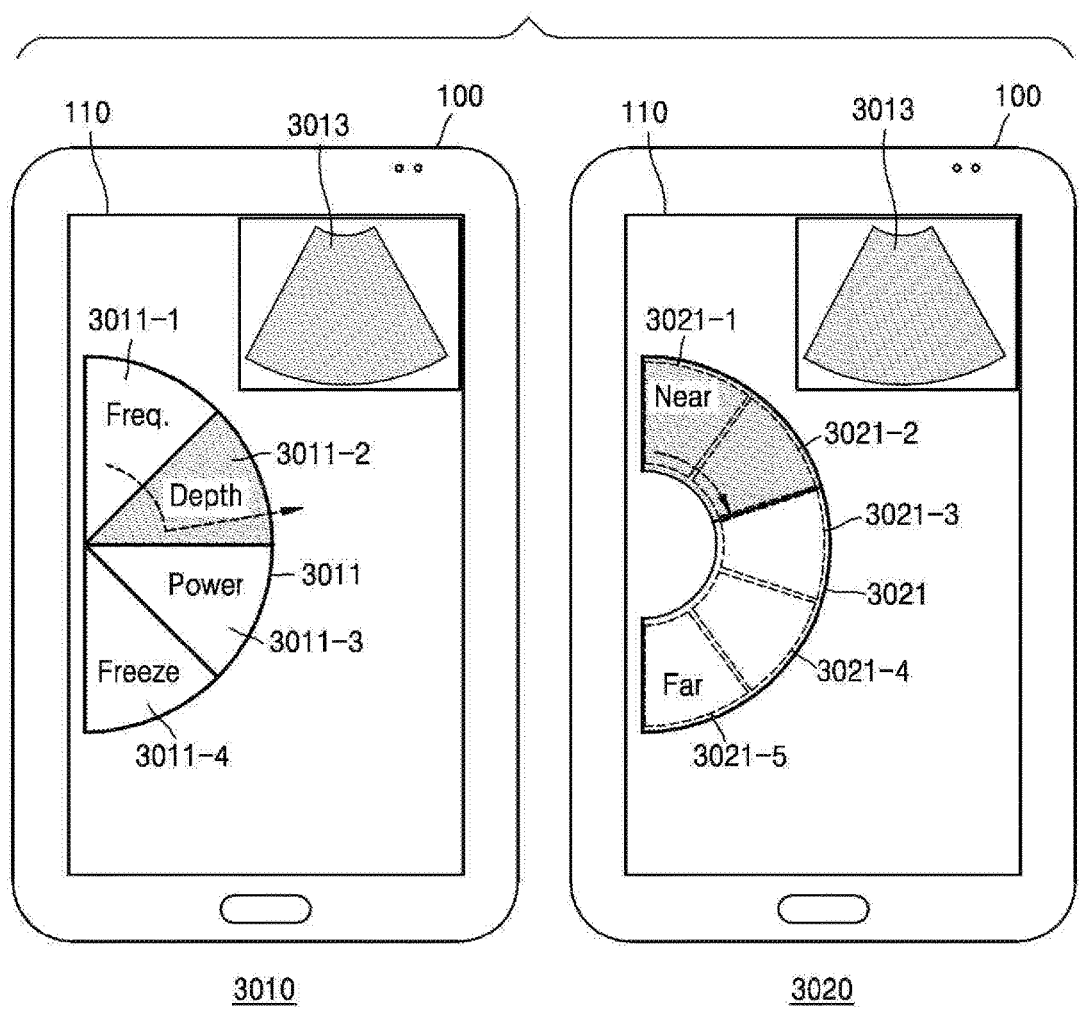
FIG. 30 illustrates an example of a UI provided by a medical image display apparatus according to an exemplary embodiment.

FIG. 30 illustrates an example of UIs 3011 and 3021 provided by a medical image display apparatus 100 according to an exemplary embodiment.

Referring to FIG. 30, the medical image display apparatus 100 displays the UI 3011 configured to receive a swipe touch and a flick touch. In this case, the medical image display apparatus 100 is connected to the ultrasound diagnosis device (11 of FIG. 1) or the ultrasound probe (12 of FIG. 1).

As shown in a portion 3010, the medical image display apparatus 100 may display a medical image 3013 and the UI 3011 related to the medical image 3013. The UI 3011 may include a plurality of icons 3011-1 through 3011-4, i.e., an icon 3011-1 related to a function of adjusting a frequency of an ultrasound signal, an icon 3011-2 related to a function of adjusting a depth of penetration of an ultrasound signal, an icon 3011-3 related to a function of adjusting intensity of an ultrasound signal, and an icon 3011-4 related to a function of changing an operating mode of the ultrasound diagnosis device 11 from a live mode to a freeze mode. To adjust a parameter related to the medical image 3013, the user may input a touch gesture for selecting at least one of the plurality of icons 3011-1 through 3011-4.

To adjust a depth parameter related to a depth of penetration of an ultrasound signal, the user may select the icon 3011-2. When the medical image display apparatus 100 receives a swipe touch involving movement of a user's finger from a certain region in the UI 3011 into a region where the icon 3011-2 is displayed and a flick touch involving movement of the user's finger from the region where the icon 3011-2 is displayed outside a region where the UI 3011 is displayed, the medical image display apparatus 100 may determine that the touch gesture for selecting the icon 3011-2 has been received. An arrow in the portion 3010 represents the user's touch gesture for selecting the icon 3011-2.

As shown in a portion 3020, when the icon 3011-2 is selected, the medical image display apparatus 100 may display the UI 3021 for adjusting a depth parameter corresponding to the icon 3011-2.

Referring to FIG. 30, when a finger-touchable region is determined, the medical image display apparatus 100 may display UIs, for example, within the determined finger-touchable region. In a first region, the medical image display apparatus 100 may display the UI 3021 instead of the UI 3011.

As shown in the portion 3020, the UI 3021 may include five (5) sections 3021-1 through 3021-5 respectively corresponding to a plurality of values of the depth parameter corresponding to the selected icon 3011-2. The five sections 3021-1 through 3021-5 included in the UI 3021 may respectively correspond to the values of the depth parameter representing deeper penetration of an ultrasound signal, from the section 3021-1 towards the section 3021-5.

To set the depth parameter to a value corresponding to the section 3021-2, the user may select the section 3021-2. When the medical image display apparatus 100 receives a swipe touch involving movement of the user's finger from the section 3021-1 to the section 3021-2 in the UI 3021, the medical image display apparatus 100 may determine that a touch gesture for selecting the section 3021-2 has been received. An arrow in the portion 3020 represents a user's touch gesture for selecting the section 3021-2.

The medical image display apparatus 100 may change the depth parameter from a value corresponding to the section 3021-1 to a value corresponding to the section 3021-2.

The medical image display apparatus 100 may provide, for example, a moving image as a medical image. For example, the medical image display apparatus 100 may display a plurality of frames still images consecutively acquired from a moving object over time or a plurality of frames (still images) consecutively acquired from an object at a position that has changed over time.

When the user observes an object based on a moving image, it may be difficult to precisely observe cells, tissues, or organs that constitute the object, compared to observing the object based on a still image. Thus, a user provided with a moving image by the medical image display apparatus 100 may desire to store a still image of the object acquired at a certain time point for later use in diagnosis or treatment of a disease. To store the still image of the object acquired at the certain time point, the medical image display apparatus 100 may provide a UI related to a function of capturing a medical image.

Figure 31:
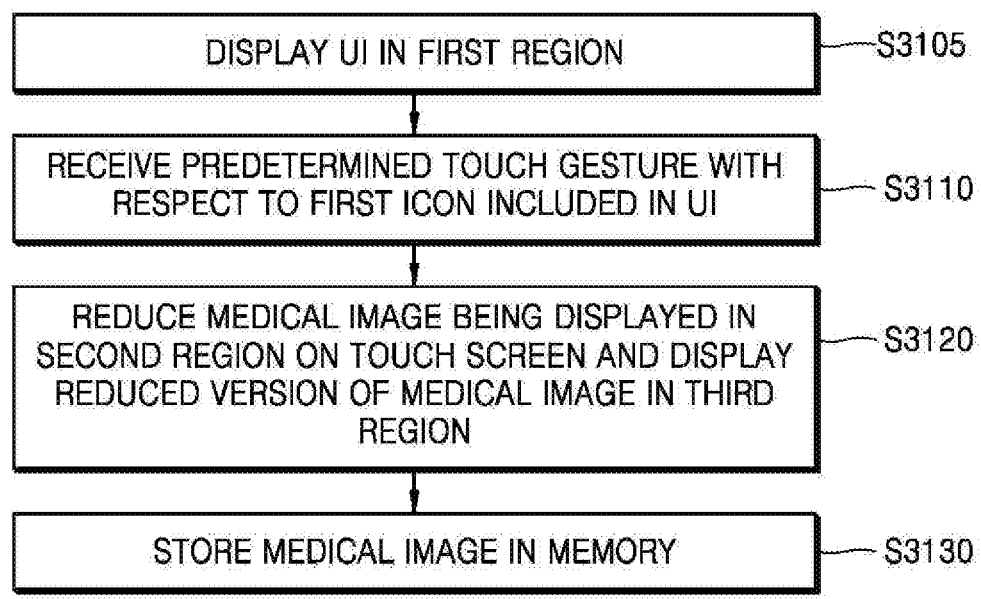
FIG. 31 is a flowchart of a method of providing, by a medical image display apparatus, a UI for capturing a medical image according to an exemplary embodiment.

FIG. 31 is a flowchart of a method of providing, by the medical image display apparatus 100, a UI for capturing a medical image according to an exemplary embodiment.

The medical image display apparatus 100 may display a UI (S3105). Because operation S3105 illustrated in FIG. 31 corresponds to operation S530 illustrated in FIG. 5, the same descriptions as provided above with respect to operation S530 will be omitted below.

As illustrated in FIG. 5, the medical image display apparatus 100 may select a UI corresponding to a size of a first region from among a plurality of UIs and display the selected UI. The medical image display apparatus 100 may display the UI within the first region determined as a finger-touchable region.

The UI may include a plurality of icons that are selectable by a user. An icon may be a character or picture to represent a command for performing a function provided by the medical image display apparatus 100.

The medical image display apparatus 100 may receive a predetermined touch gesture with respect to a first icon from among a plurality of icons included in the UI (S3110).

The plurality of icons in the UI may include the first icon related to a function of capturing a medical image being displayed on the touch screen 110 of the medical image display apparatus 100. To capture a medical image, the user may input a touch gesture for selecting the first ion from among the plurality of icons.

When the predetermined touch gesture with respect to the first icon is received, the medical image display apparatus 100 may determine that the first icon has been selected.

A type of touch gesture that the medical image display apparatus 100 is to receive from the user in order to select at least one icon from among a plurality of icons may be predetermined as a default value or may be set by the user.

In some exemplary embodiments, the medical image display apparatus 100 may select a UI that is configured to receive a specific touch gesture, based on the size of the first region.

When the predetermined touch gesture with respect to the first icon related to a function of capturing a medical image is received, the medical image display apparatus 100 may capture a medical image being displayed in a second region on the touch screen 110.

The medical image display apparatus 100 may reduce a medical image being displayed in a second region on the touch screen 110 and display a reduced version of the medical image in a third region (S3120). Furthermore, the medical image display apparatus 100 may store the medical image in a memory (S3130). The medical image display apparatus 100 may store the medical image in at least one of a memory included in the medical image display apparatus 100, a memory of an external device, and an external server.

Figure 32:
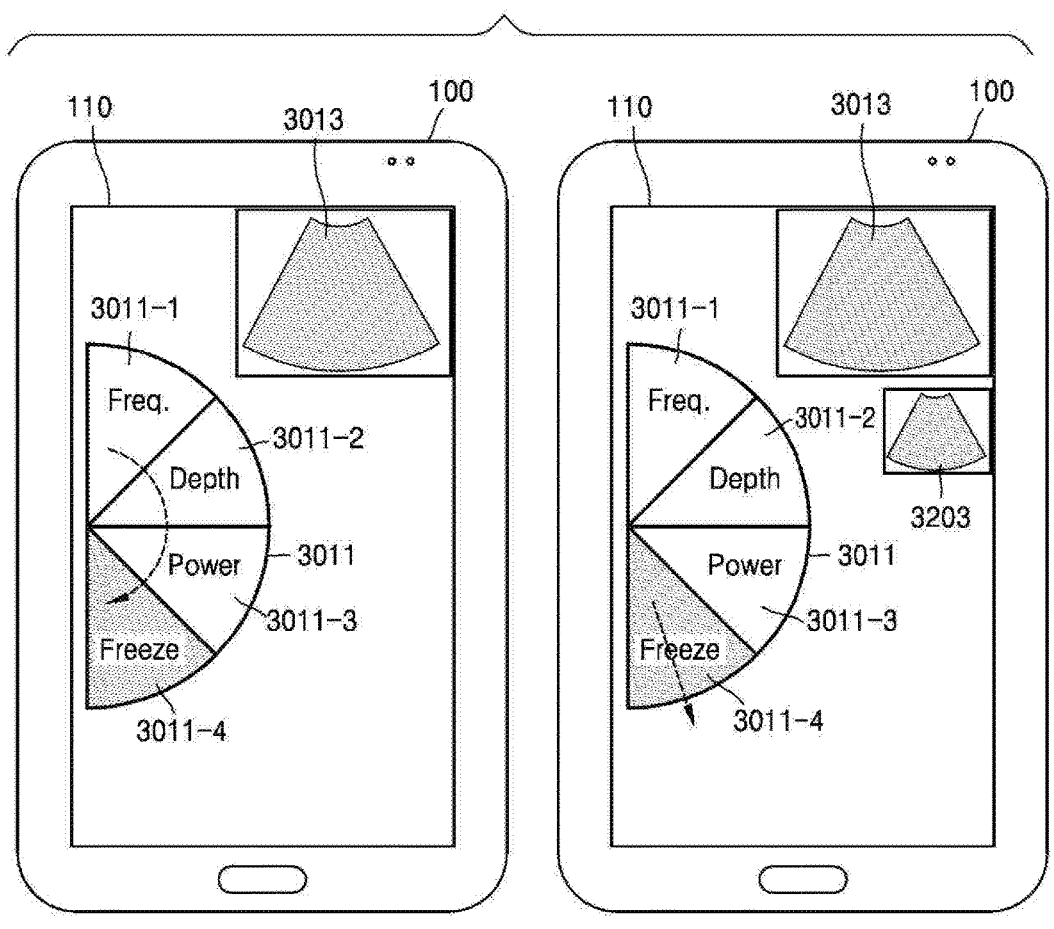
FIG. 32 illustrates an example of a UI provided by a medical image display apparatus, according to an exemplary embodiment.

FIG. 32 illustrates an example of a UI 3011 provided by a medical image display apparatus 100, according to an exemplary embodiment.

Referring to FIG. 32, the medical image display apparatus 100 displays the UI 3011 configured to receive a swipe touch and a flick touch. In this case, the medical image display apparatus 100 is connected to the ultrasound diagnosis device 11 or the ultrasound probe 12.

As shown in a portion 3210, the medical image display apparatus 100 may display the UI 3011 related to a medical image 3013 in a first region and the medical image 3013 in a second region.

The UI 3011 may include an icon 3011-1 related to a function of adjusting a frequency of an ultrasound signal, an icon 3011-2 related to a function of adjusting a depth of penetration of an ultrasound signal, an icon 3011-3 related to a function of adjusting intensity of an ultrasound signal, and an icon 3011-4 related to a function of changing an operating mode from a live mode to a freeze mode.

Before capturing the medical image 3013, the user may change an operating mode of the medical image display apparatus 100 from a live mode to a freeze mode. A live mode may refer to a mode in which a real-time image of an object is provided, and a freeze mode may refer to a mode in which a still image of an object acquired at a certain time point is provided. The user may select the icon 3011-4 to change an operating mode of the medical image display apparatus 100 to a freeze mode. An arrow in the portion 3210 represents the user's touch gesture for selecting the icon 3011-4.

When the medical image display apparatus 100 receives a swipe touch involving movement of a user's finger from a certain region in the UI 3011 into a region where the icon 3011-4 is displayed, the medical image display apparatus 100 may change an operating mode from a live mode to a freeze mode. When the swipe touch is received, the medical image display apparatus 100 may provide a still image of an object acquired at a certain time point as the medical image 3013.

To capture the medical image 3013 being displayed in the second region, the user may select the icon 3011-4. Upon receipt of a flick touch involving movement of the user's finger from the region where the icon 3011-4 is displayed outside a region where the UI 3011 is displayed, the medical image display apparatus 100 may determine that a predetermined touch gesture with respect to the icon 3011-4 has been received. An arrow in the portion 3220 may represent a user's touch gesture for selecting the icon 3011-4.

As shown in the portion 3220, when the predetermined touch gesture with respect to the icon 3011-4 is received, the medical image display apparatus 100 may display in a third region a reduced version 3203 of the medical image 3013 being displayed in the second region. Furthermore, the medical image display apparatus 100 may store the medical image 3013 in a memory.

According to an exemplary embodiment, the medical image display apparatus 100 may provide a UI for changing an operating mode related to a medical image. An operation mode related to a medical image may include at least one of a mode in which an operation of acquiring the medical image is performed and a mode in which an operation of displaying the medical image is performed.

When the medical image display apparatus 100 is connected to the ultrasound diagnosis device 11 or the ultrasound probe 12, the medical image display apparatus 100 may provide a UI for changing an operating mode related to an operation of acquiring a medical image by the ultrasound probe 12. For example, the medical image display apparatus 100 may control the ultrasound probe 12 to operate in at least one of a live mode in which ultrasound image data is acquired in real-time and a freeze mode in which acquisition of the ultrasound image data is stopped and a still image is provided.

Figure 33:
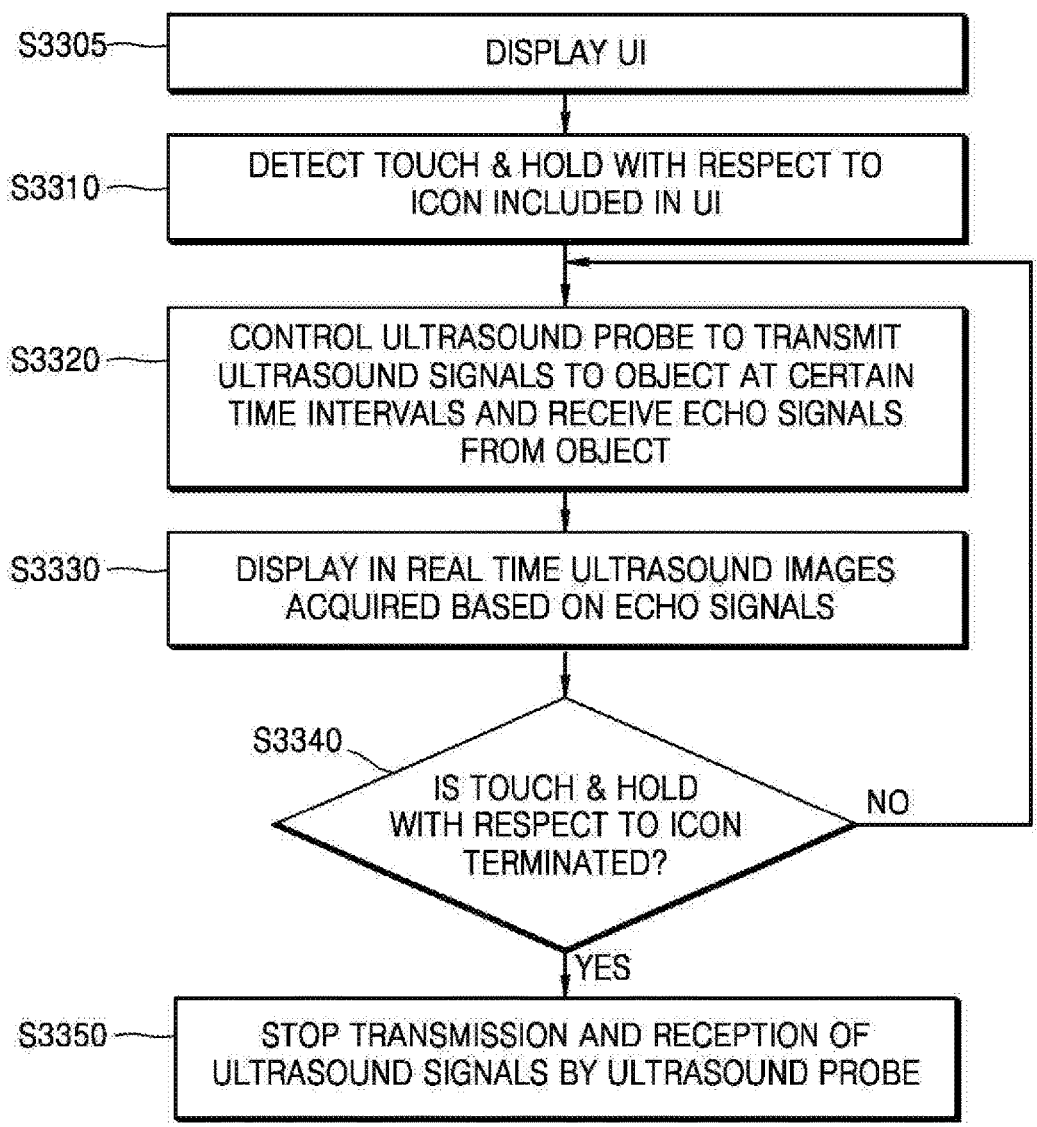
FIG. 33 is a flowchart of a method of providing, by a medical image display apparatus, a UI for controlling an ultrasound probe, according to an exemplary embodiment.

FIG. 33 is a flowchart of a method of providing, by the medical image display apparatus 100, a UI for controlling an ultrasound probe, according to an exemplary embodiment.

The medical image display apparatus 100 may display a UI (S3305). Because operation S3305 illustrated in FIG. 33 may correspond to operation S530 illustrated in FIG. 5, the same descriptions as provided above with respect to operation S530 will be omitted below.

As illustrated in FIG. 5, the medical image display apparatus 100 may select a UI corresponding to a size of a first region from among a plurality of UIs and display the selected UI. The medical image display apparatus 100 may display the UI within the first region determined as a finger-touchable region.

The UI may include at least one icon that is selectable by a user. An icon may be a character or picture to represent a command for performing a function provided by the medical image display apparatus 100.

The medical image display apparatus 100 may detect touch and hold with respect to an icon included in the UI (S3310).

The icon included in the UI may represent a command that enables the medical image display apparatus 100 to change an operating mode related to a medical image. For example, the icon may represent a command that enables the medical image display apparatus 100 to change an operating mode of an ultrasound probe connected to the medical image display apparatus 100 from a live mode to a freeze mode or vice versa.

The medical image display apparatus 100 may indicate its operating mode by using at least one of a color, a shape, a size, and a contrast of the icon. In some exemplary embodiments, the medical image display apparatus 100 may indicate its operating mode by using at least one of a character, a symbol, and a figure on the icon.

When the touch and hold with respect to the icon is detected, the medical image display apparatus 100 may operate in a live mode (S3320). The medical image display apparatus 100 may control an ultrasound probe to transmit ultrasound signals to an object at predetermined time intervals and receive echo signals from the object.

The medical image display apparatus 100 may display in real-time ultrasound images acquired based on the echo signals (S3330).

The ultrasound probe connected to the medical image display apparatus 100 may generate ultrasound image data based on the echo signals received from the object. The medical image display apparatus 100 may receive the ultrasound image data from the ultrasound probe. The medical image display apparatus 100 may provide a moving image of the object by displaying a plurality of frames consecutively acquired over time based on the ultrasound image data.

The medical image display apparatus 100 may determine whether the touch and hold with respect to the icon is terminated (S3340).

If the touch and hold with respect to the icon continues to be detected, the medical image display apparatus 100 may operate in a live mode by repeating operation S3320 and S3330.

If it is determined that the touch and hold with respect to the icon is terminated, the medical image display apparatus 100 may change an operating mode from a live mode to a freeze mode (S3350). The medical image display apparatus 100 may control the ultrasound probe to stop transmitting or receiving ultrasound signals. If it is determined that the touch and hold with respect to the icon is terminated, the medical image display apparatus 100 may also provide a still image of the object. For example, the medical image display apparatus 100 may display a still image that is generated from ultrasound image data received from the ultrasound probe immediately before a time point when the touch and hold with respect to the icon is terminated.

While FIG. 33 illustrates an example where the medical image display apparatus 100 changes an operating mode based on whether the touch and hold is received with respect to an icon, exemplary embodiments are not limited thereto. According to various exemplary embodiments, the medical image display apparatus 100 may change an operating mode based on whether a predetermined touch gesture with respect to an icon is received. A type of touch gesture that the medical image display apparatus 100 is to receive from the user to select at least one icon from among a plurality of icons may be predetermined as a default value or may be set by the user. In some exemplary embodiments, the medical image display apparatus 100 may select a UI that is configured to receive a specific touch gesture, based on the size of the first region.

In addition, as described below with reference to FIGS. 34 through 40C, the medical image display apparatus 100 may provide a UI including one icon related to a function of changing an operating mode, a function of adjusting a parameter related to a medical image, and a function of capturing the medical image. The medical image display apparatus 100 may perform various functions according to which type of touch gesture is received with respect to the icon included in the UI, and thus, a space on the touch screen 110 occupied by the UI may be reduced.

Figure 34:
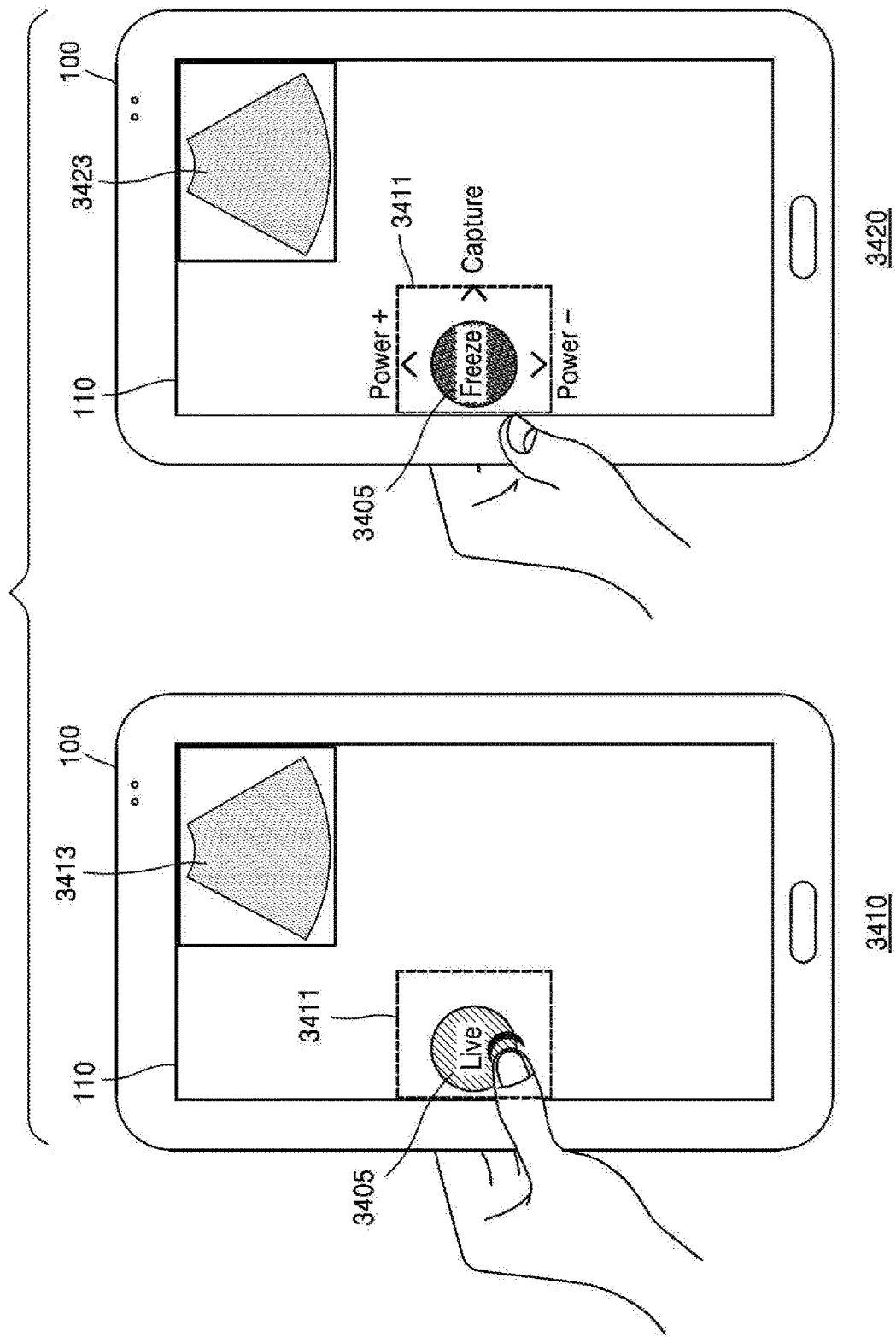
FIG. 34 illustrates an example of a UI provided by a medical image display apparatus, according to other exemplary embodiments.

FIG. 34 illustrates an example of a UI 3411 provided by a medical image display apparatus 100, according to an exemplary embodiment.

Referring to FIG. 34, the medical image display apparatus 100 displays the UI 3411 configured to receive a touch and hold gesture. In this case, the medical image display apparatus 100 is connected to the ultrasound diagnosis device 11 or the ultrasound probe 12.

As shown in a portion 3410, the medical image display apparatus 100 may display a medical image 3413 (e.g., an ultrasound image) and the UI 3411 for changing an operating mode related to an operation of acquiring the medical image 3413 by the ultrasound probe 12. The UI 3411 may include an icon 3405 corresponding to a function of changing an operating mode of the medical image display apparatus 100.

The user may input a touch and hold gesture with respect to the icon 3405 so that the medical image display apparatus 100 may operate in a live mode.

As shown in the portion 3410, when the medical image display apparatus 100 operates in a live mode (i.e., the ultrasound probe 12 transmits or receives ultrasound signals at predetermined time intervals, and the medical image display apparatus 100 provides an ultrasound image in real-time), the medical image display apparatus 100 may indicate a current operating mode by displaying "Live" on the icon 3405.

When the touch and hold gesture with respect to the icon 3405 is detected, the medical image display apparatus 100 may control the ultrasound probe 12 to transmit ultrasound signals to an object at predetermined time intervals and receive echo signals from the object. The medical image display apparatus 100 may display the ultrasound image 3413 in real-time while detecting the touch and hold gesture with respect to the icon 3405.

As shown in a portion 3420, the user may lift a finger off the icon 3405 in order to change an operating mode of the medical image display apparatus 100 from a live mode to a freeze mode.

If it is determined that the touch and hold gesture with respect to the icon 3405 is terminated, the medical image display apparatus 100 may change an operating mode from a live mode to a freeze mode. The medical image display apparatus 100 may display a current operating mode by indicating "Freeze" on the icon 3405.

When the touch and hold gesture with respect to the icon 3405 is terminated, the medical image display apparatus 100 may control the ultrasound probe 12 to stop transmitting or receiving ultrasound signals. Furthermore, the medical image display apparatus 100 may display an ultrasound still image 3423.

As shown in the portion 3420, when the touch and hold gesture with respect to the icon 3405 is terminated, the icon 3405 may provide a function of adjusting intensity of an ultrasound signal, a function of changing an operating mode from a freeze mode to a live mode and a function of capturing an ultrasound image.

When the touch and hold gesture with respect to the icon 3405 indicated as "Freeze" is detected again, the medical image display apparatus 100 may change an operating mode from a freeze mode to a live mode.

Furthermore, the medical image display apparatus 100 may adjust intensity of an ultrasound signal or capture an ultrasound image being displayed, based on a flick touch with respect to the icon 3405.

UIs including an icon that provides a function of capturing a medical image and a function of adjusting a parameter related to the medical image will now be described in detail with reference to FIGS. 35 through 40.

Figure 35:
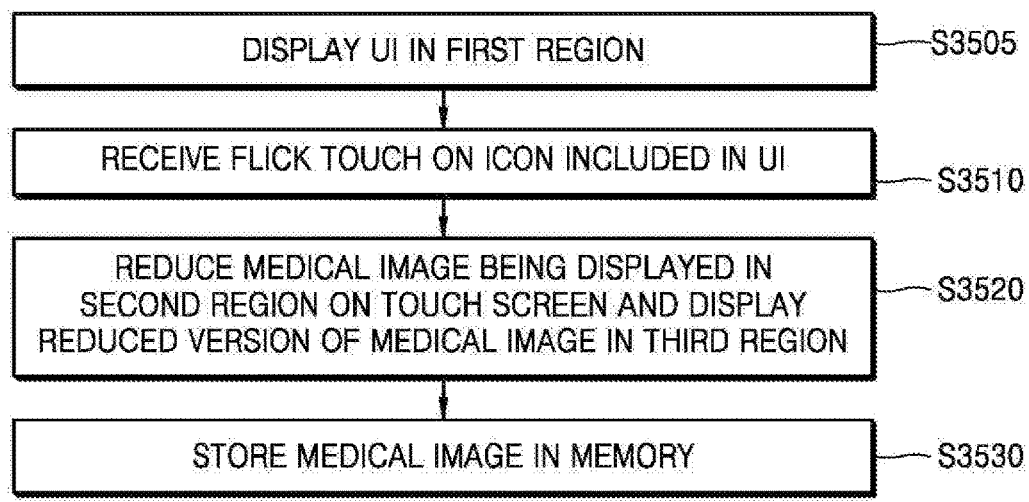
FIG. 35 is a flowchart of a method of providing, by a medical image display apparatus, a UI for capturing a medical image, according to an exemplary embodiment.

FIG. 35 is a flowchart of a method of providing, by the medical image display apparatus 100, a UI for capturing a medical image, according to an exemplary embodiment.

The medical image display apparatus 100 may display a UI (S3505). Because operation S3505 illustrated in FIG. 35 corresponds to operation S530 illustrated in FIG. 5, the same descriptions as provided above with respect to operation S530 will be omitted below.

As illustrated in FIG. 5, the medical image display apparatus 100 may select a UI corresponding to a size of a first region from among a plurality of UIs and display the selected UI. The medical image display apparatus 100 may display the UI within the first region determined as a finger-touchable region.

The UI may include at least one icon that is selectable by a user. An icon may be a character or picture to represent a command for performing a function provided by the medical image display apparatus 100.

The medical image display apparatus 100 may receive a flick touch with respect to an icon included in the UI (S3510).

The UI may include an icon related to a function of capturing a medical image being displayed on the touch screen 110 of the medical image display apparatus 100. To capture a medical image, the user may input a flick touch on the icon related to a function of capturing the medical image.

When the flick touch performed with respect to the icon in a predetermined direction is received, the medical image display apparatus 100 may determine that a command for capturing a medical image has been received from the user. When the flick touch performed with respect to the icon is received, the medical image display apparatus 100 may capture a medical image being displayed in a second region on the touch screen 110.

The medical image display apparatus 100 may reduce a medical image being displayed in a second region on the touch screen 110 and display a reduced version of the medical image in a third region (S3520). Furthermore, the medical image display apparatus 100 may store the medical image in a memory (S3530). The medical image display apparatus 100 may store the medical image in at least one of a memory included in the medical image display apparatus 100, a memory of an external device, and an external server.

Figure 36A:
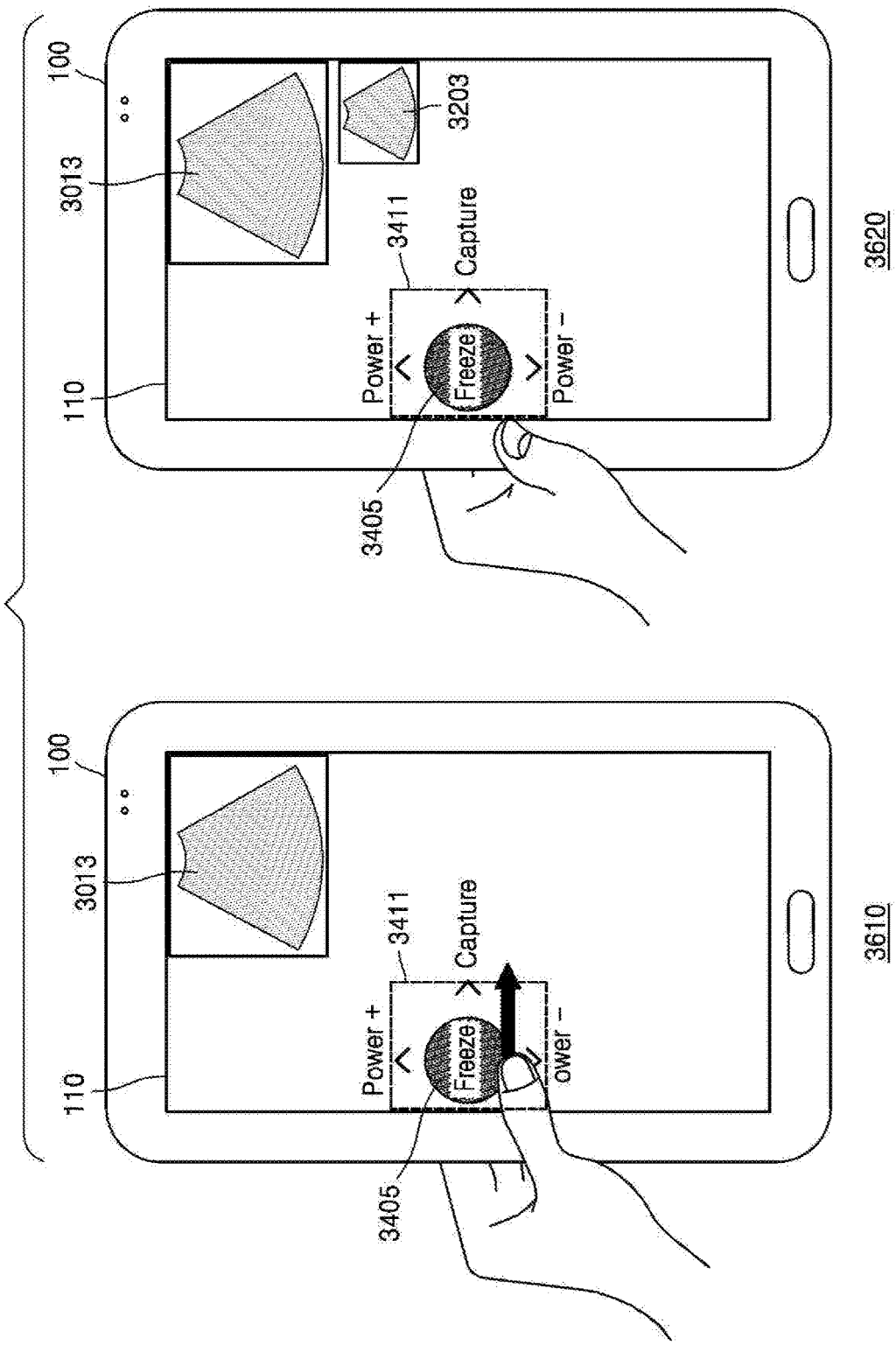
FIG. 36A and FIG. 36B illustrate examples of UIs provided by a medical image display apparatus, according to other exemplary embodiments.
Figure 36B:
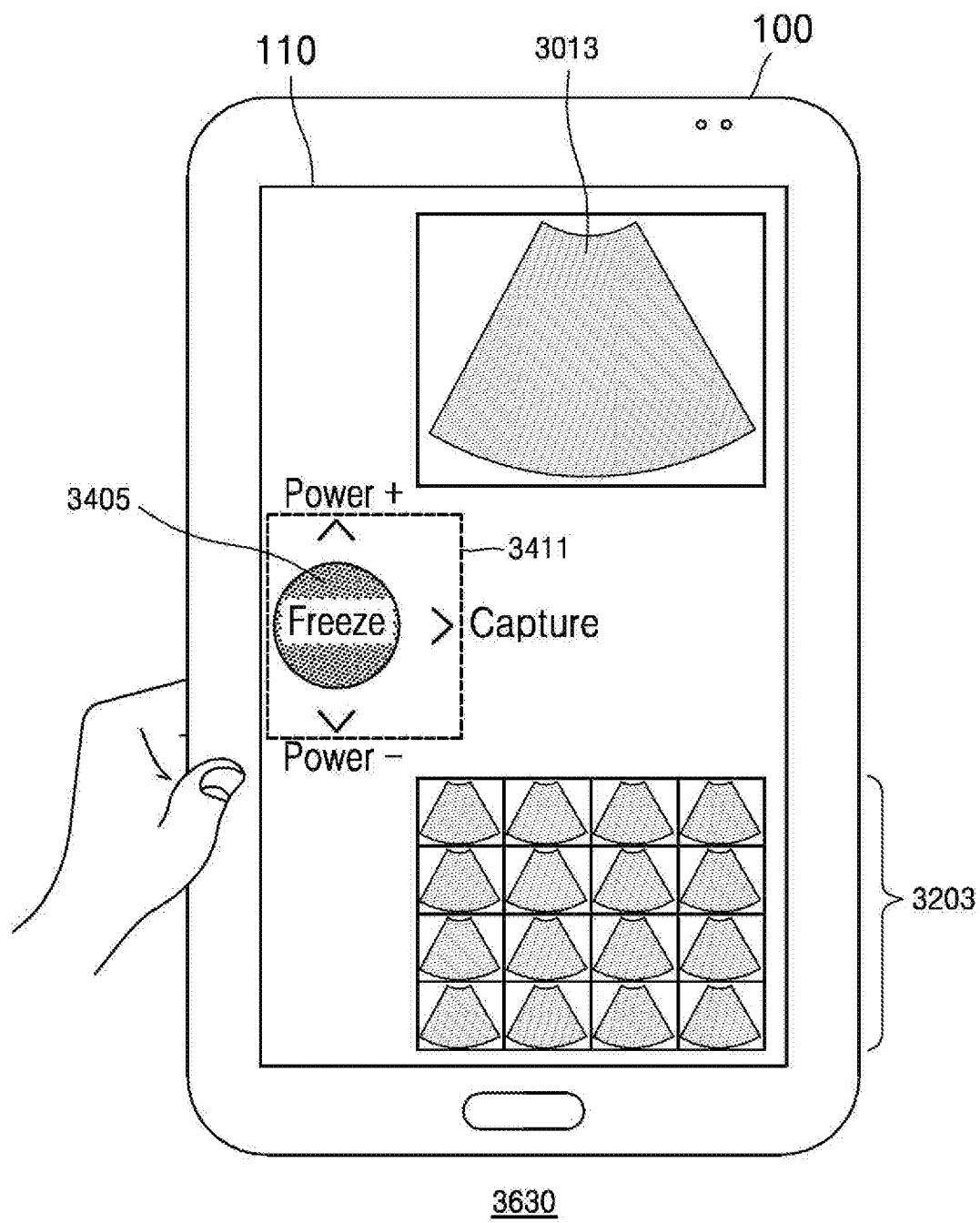

FIGS. 36A and 36B illustrate examples of a UI 3411 provided by a medical image display apparatus 100, according to an exemplary embodiment.

Referring to FIGS. 36A and 36B, the medical image display apparatus 100 displays the UI 3411 configured to receive a flick touch. In this case, the medical image display apparatus 100 may be connected to the ultrasound diagnosis device 11 or the ultrasound probe 12.

As shown in a portion 3610, the medical image display apparatus 100 may display the UI 3411 related to a medical image 3013 in a first region as well as the medical image 3013 in a second region.

The UI 3411 may include an icon 3405 related to a function of adjusting intensity of an ultrasound signal, a function of changing an operating mode from a freeze mode to a live mode, and a function of capturing an ultrasound image.

To capture the medical image 3013 being displayed in the second region, the user may input a flick touch on the icon 3405. Upon receipt of a flick touch involving moving a finger outwards from the region where the icon 3405 is displayed along a direction indicated by an arrow, the medical image display apparatus 100 may determine that a command for capturing the medical image 3013 has been received from the user. An arrow in the portion 3610 represents a user's touch gesture for selecting the icon 3405.

As shown in a portion 3620, upon receipt of the flick touch performed with respect to the icon 3405 in the predetermined direction, the medical image display apparatus 100 may display a reduced version 3203 of the medical image 3013 being displayed in the second region in a third region. Furthermore, the medical image display apparatus 100 may store the medical image 3013 in a memory.

According to an exemplary embodiment, as the flick touch with respect to the icon 3405 is received in the predetermined direction, the medical image display apparatus 100 may capture the medical image 3013 and then receive again a flick touch with respect to the icon 3405.

As shown in a portion 3630 of FIG. 36B, as a flick touch with respect to the icon 3405, or in some exemplary embodiments, a plurality of flick touches, is received in the predetermined direction, the medical image display apparatus 100 may capture a plurality of medical images. The medical image display apparatus 100 may display reduced versions 3203 of the captured plurality of medical images in a third region. Furthermore, the medical image display apparatus 100 may store the captured plurality of medical images in a memory.

Figure 37:
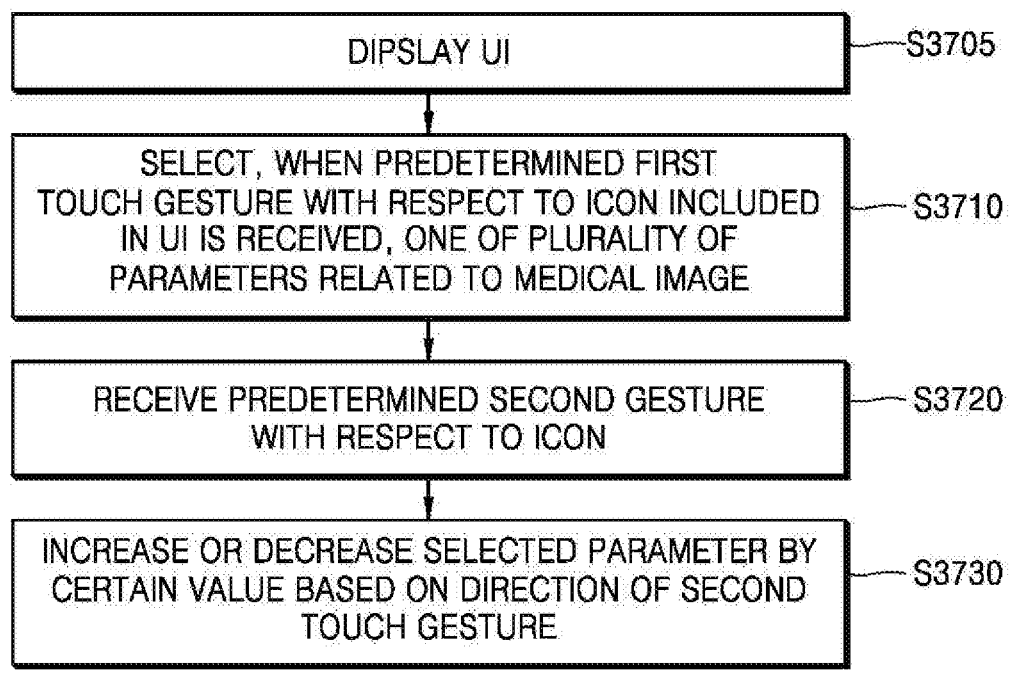
FIG. 37 is a flowchart of a method of providing, by a medical image display apparatus, a UI for adjusting a parameter, according to an exemplary embodiment.

FIG. 37 is a flowchart of a method of providing, by the medical image display apparatus 100, a UI for adjusting a parameter, according to an exemplary embodiment.

The medical image display apparatus 100 may display a UI (S3705). Because operation S3705 illustrated in FIG. 37 corresponds to operation S530 illustrated in FIG. 5, the same descriptions as provided above with respect to operation S530 will be omitted below.

As illustrated in FIG. 5, the medical image display apparatus 100 may select a UI corresponding to a size of a first region from among a plurality of UIs and display the selected UI. The medical image display apparatus 100 may display the UI within the first region determined as a finger-touchable region.

The UI may include at least one icon that is selectable by a user. An icon may be a character or picture to represent a command for performing a function provided by the medical image display apparatus 100.

The medical image display apparatus 100 may provide the UI including an icon corresponding to a function of adjusting a parameter related to a medical image being displayed on the touch screen 110 of the medical image display apparatus 100.

When a predetermined first touch gesture with respect to an icon included in the UI is received, the medical image display apparatus 100 may select one of a plurality of parameters related to a medical image (S3710).

A type of touch gesture that the medical image display apparatus 100 is to receive from the user in order to select one of a plurality of parameters related to a medical image may be predetermined as a default value or may be set by the user. In some exemplary embodiments, the medical image display apparatus 100 may select a UI that is configured to receive a specific touch gesture, based on the size of the first region. For example, the predetermined first touch gesture may include a tap touch, a double tap touch, a touch and hold gesture, a flick touch, or the like.

The medical image display apparatus 100 may select one of the plurality of parameters based, for example, on a direction in which the predetermined first touch gesture is received, or the number of times the predetermined first touch gesture is received. For example, when a double tap touch with respect to the icon is received, the medical image display apparatus 100 may select an intensity parameter related to intensity of an ultrasound signal from among the plurality of parameters.

The medical image display apparatus 100 may indicate the selected parameter by using at least one of a color, a shape, a size, and a contrast of the icon. In some exemplary embodiments, the medical image display apparatus 100 may indicate the selected parameter by using at least one of a character, a symbol, and a figure on the icon.

The medical image display apparatus 100 may receive a predetermined second touch gesture with respect to the icon (S3720).

By inputting the predetermined second touch gesture with respect to the icon, the user may adjust the parameter selected in operation S3710. When the second touch gesture with respect to the icon is received in at least one predetermined direction, the medical image display apparatus 100 may determine that a command for adjusting a value of a parameter related to the medical image has been received from the user.

A type of touch gesture that the medical image display apparatus 100 is to receive from the user in order to adjust a parameter related to the medical image may be predetermined as a default value or may be set by the user. In some exemplary embodiments, the medical image display apparatus 100 may select a UI that is configured to receive a specific touch gesture, based on the size of the first region. For example, the predetermined second touch gesture may include a flick touch or the like.

The medical image display apparatus 100 may increase or decrease the selected parameter by a certain value based on a direction of the second touch gesture received in operation S3720 (S3730).

A certain value by which the medical image display apparatus 100 increases or decreases the selected parameter may be predetermined as a default value, or may be set by the user.

For example, if the second touch gesture with respect to the icon is received along a first direction, the medical image display apparatus 100 may increase the selected parameter by a certain value. If the second touch gesture with respect to the icon is received along a second direction, the medical image display apparatus 100 may decrease the selected parameter by the certain value.

Figure 38:
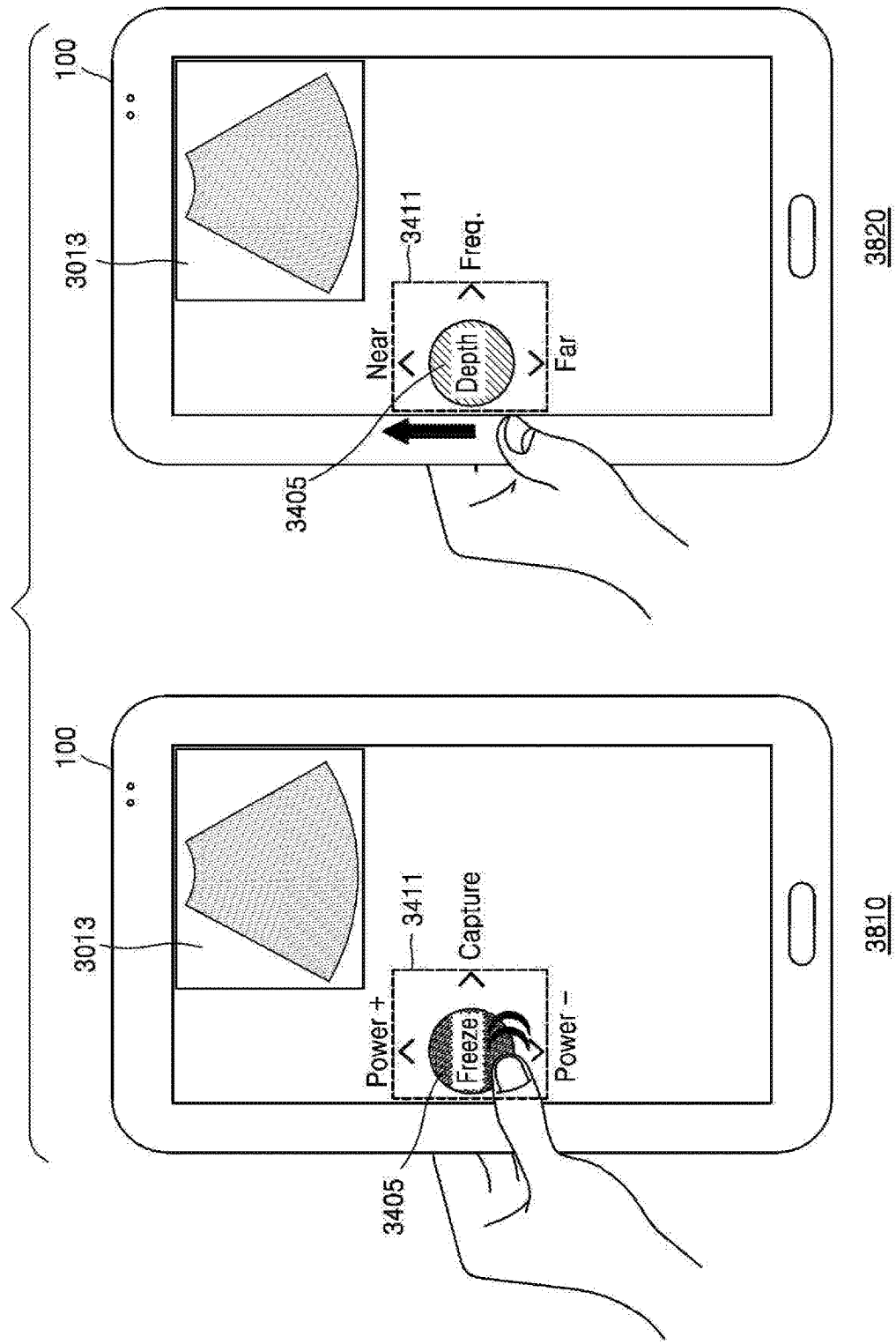
FIG. 38 illustrates an example of a UI provided by a medical image display apparatus, according to an exemplary embodiment.

FIG. 38 illustrates an example of a UI 3411 provided by a medical image display apparatus 100, according to an exemplary embodiment.

Referring to FIG. 38, the medical image display apparatus 100 displays the UI 3411 configured to receive a touch and hold gesture, a double tap touch, and a flick touch. In this case, the medical image display apparatus 100 is connected to the ultrasound diagnosis device 11 or the ultrasound probe 12.

As shown in a portion 3810, the medical image display apparatus 100 may display the UI 3411 related to a medical image 3013 in a first region as well as the medical image 3013 in a second region.

The UI 3411 may include an icon 3405 related to a function of adjusting intensity of an ultrasound signal, a function of changing an operating mode from a freeze mode to a live mode, and a function of capturing an ultrasound image.

As shown in the portion 3810, when a touch and hold gesture with respect to the icon 3405 is terminated, the medical image display apparatus 100 may select an intensity parameter related to intensity of an ultrasound signal from among a plurality of parameters related to the medical image 3013. The medical image display apparatus 100 may indicate the selected parameter by, for example, displaying "Power" near the icon 3405.

To adjust the intensity of an ultrasound signal, the user may input a flick touch with respect to the icon 3405. If a flick touch involving moving a user's finger outwards and upwards from a region where the icon 3405 is displayed is received, the medical image display apparatus 100 may increase the intensity of the ultrasound signal by a certain value. On the other hand, if a flick touch involving moving the user's finger downwards from the region where the icon 3405 is displayed, the medical image display apparatus 100 may decrease the intensity of the ultrasound signal by a certain value.

As shown in portions 3810 and 3820, when a double tap touch with respect to the icon 3405 is received, the medical image display apparatus 100 may select a depth parameter from among the plurality of parameters related to the medical image 3013. The medical image display apparatus 100 may display the selected depth parameter by indicating "Depth" on the icon 3405.

To adjust the selected depth parameter, the user may input a flick touch with respect to the icon 3405. If a flick touch involving moving the user's finger outwards and upwards from the region where the icon 3405 is displayed is received, the medical image display apparatus 100 may decrease the depth parameter by a certain value. On the other hand, if a flick touch involving moving the user's finger downwards from the region where the icon 3405 is displayed, the medical image display apparatus 100 may increase the depth parameter by a certain value. An arrow in the portion 3820 represents a user's flick touch that decreases a depth of penetration of an ultrasound signal.

Figure 39:
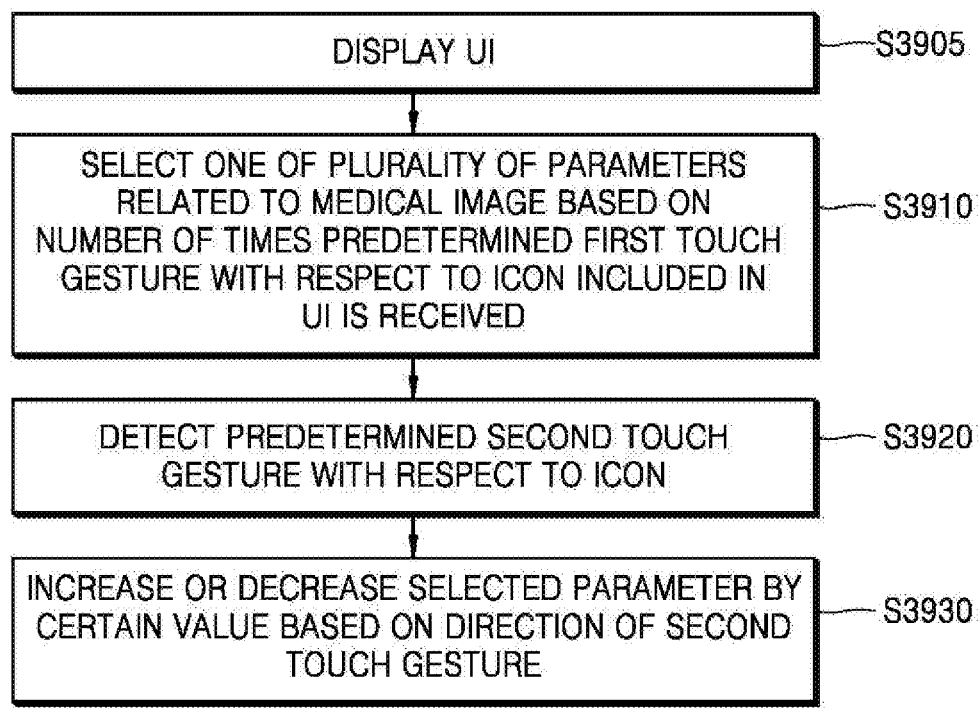
FIG. 39 is a flowchart of a method of providing, by a medical image display apparatus, a UI for adjusting a parameter, according to an exemplary embodiment.

FIG. 39 is a flowchart of a method of providing, by the medical image display apparatus 100, a UI for adjusting a parameter, according to an exemplary embodiment.

The medical image display apparatus 100 may display a UI (S3905). Because operation S3905 illustrated in FIG. 39 corresponds to operation S530 illustrated in FIG. 5, the same descriptions as provided above with respect to operation S530 will be omitted below.

As illustrated in FIG. 5, the medical image display apparatus 100 may select a UI corresponding to a size of a first region from among a plurality of UIs and display the selected UI. The medical image display apparatus 100 may display the UI within the first region determined as a finger-touchable region.

The UI may include at least one icon that is selectable by a user. An icon may be a character or picture to represent a command for performing a function provided by the medical image display apparatus 100.

The medical image display apparatus 100 may provide the UI including an icon corresponding to a function of adjusting a parameter related to a medical image being displayed on the touch screen 110 of the medical image display apparatus 100.

When a predetermined first touch gesture with respect to an icon included in the UI is received, the medical image display apparatus 100 may select one of a plurality of parameters related to a medical image (S3910). The medical image display apparatus 100 may select one of the plurality of parameters related to the medical image based on the number of times the predetermined first touch gesture is received.

A type of touch gesture that the medical image display apparatus 100 is to receive from the user in order to select one of a plurality of parameters related to a medical image may be predetermined as a default value or may be set by the user. In some exemplary embodiments, the medical image display apparatus 100 may select a UI that is configured to receive a specific touch gesture, based on the size of the first region. For example, the predetermined first touch gesture may include a tap touch, a double tap touch, a touch and hold gesture, a flick touch, or the like.

The medical image display apparatus 100 may indicate the selected parameter by using at least one of a color, a shape, a size, and a contrast of the icon. In some exemplary embodiments, the medical image display apparatus 100 may indicate the selected parameter by using at least one of a character, a symbol, and a figure on the icon.

The medical image display apparatus 100 may receive a predetermined second touch gesture with respect to the icon (S3920).

By inputting the predetermined second touch gesture, the user may adjust the parameter selected in operation S3910. When the second touch gesture with respect to the icon is received in at least one predetermined direction, the medical image display apparatus 100 may determine that a command for adjusting a value of a parameter related to the medical image has been received from the user.

A type of touch gesture that the medical image display apparatus 100 is to receive from the user in order to adjust a parameter related to a medical image may be predetermined as a default value or may be set by the user. In some exemplary embodiments, the medical image display apparatus 100 may select a UI that is configured to receive a specific touch gesture, based on the size of the first region. For example, the predetermined second touch gesture may include a flick touch or the like.

The medical image display apparatus 100 may increase or decrease the selected parameter by a certain value based on a direction of the second touch gesture received in operation S3920 previously (S3930).

A certain value by which the medical image display apparatus 100 increases or decreases the selected parameter may be predetermined as a default value or may be set by the user.

For example, if the second touch gesture with respect to the icon is received along a first direction, the medical image display apparatus 100 may increase the selected parameter by a certain value. If the second touch gesture with respect to the icon is received along a second direction, the medical image display apparatus 100 may decrease the selected parameter by the certain value.

Figure 40A:
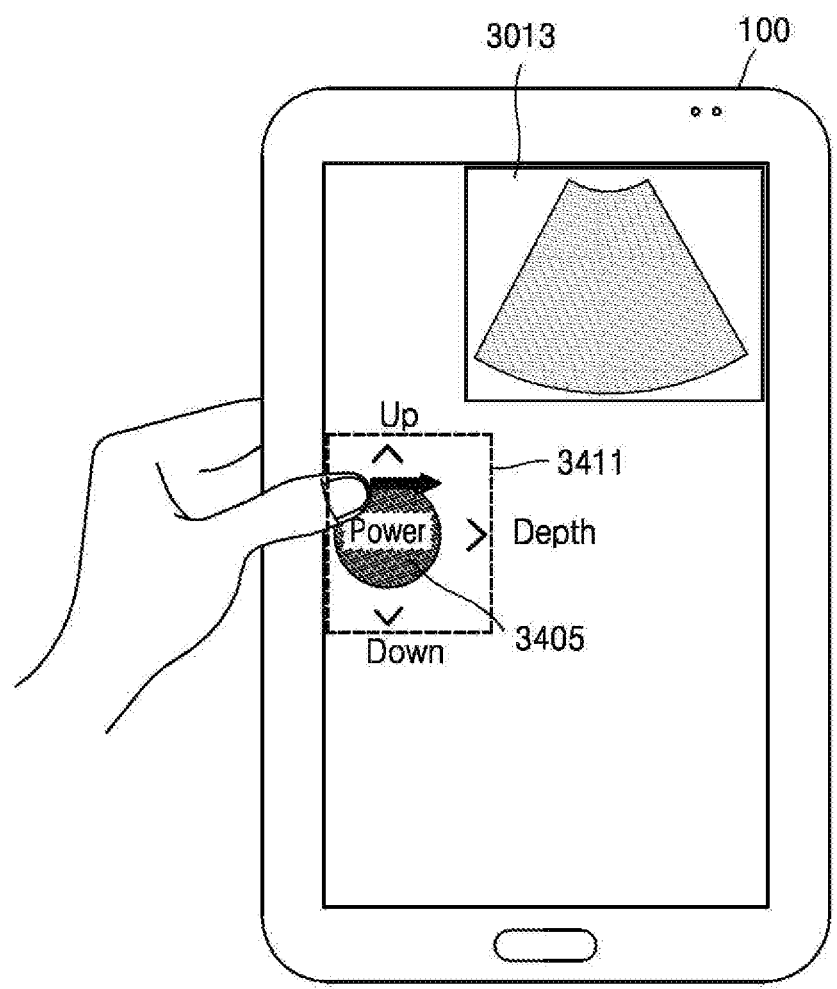
FIG. 40A, FIG. 40B and FIG. 40C illustrate examples of a UI provided by a medical image display apparatus, according to exemplary embodiments.
Figure 40B:
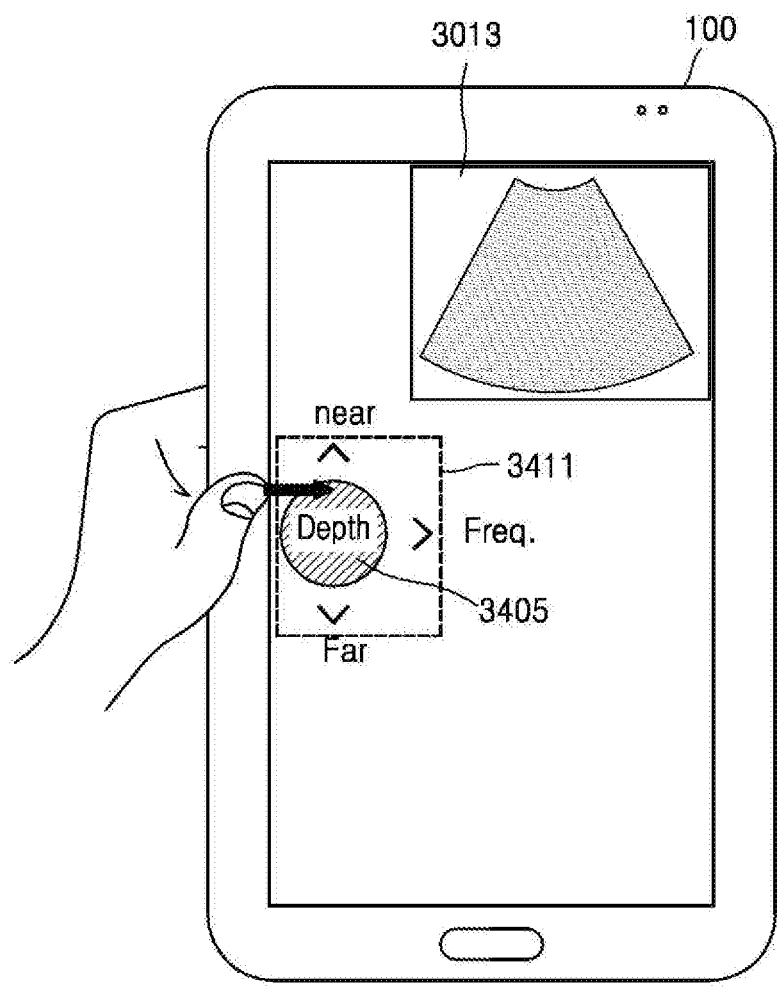
Figure 40C:
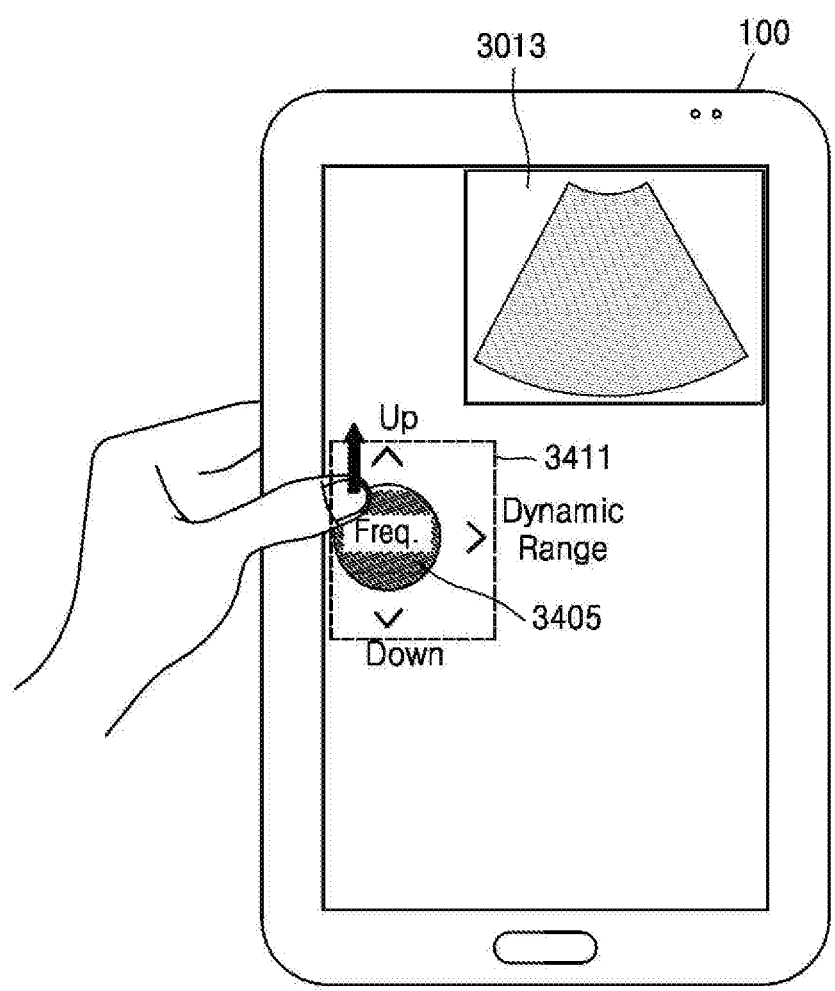

FIGS. 40A through 40C illustrate examples of a UI 3411 provided by a medical image display apparatus 100, according to an exemplary embodiment.

Referring to FIGS. 40A through 40C, the medical image display apparatus 100 displays the UI 3411 configured to receive a flick touch. In this case, the medical image display apparatus 100 is connected to the ultrasound diagnosis device 11 or the ultrasound probe 12.

As shown in portion 4010 of FIG. 40A, the medical image display apparatus 100 may display the UI 3411 related to a medical image 3013 in a first region as well as the medical image 3013 in a second region.

As shown in the portion 4010, the medical image display apparatus 100 may select an intensity parameter related to intensity of an ultrasound signal from among a plurality of parameters related to the medical image 3013. The medical image display apparatus 100 may display the selected parameter by indicating "Power" on an icon 3405.

In a state shown in the portion 4010, to adjust the intensity of an ultrasound signal, the user may input a flick touch on the icon 3405. If a flick touch involving moving a finger outwards and upwards from a region where the icon 3405 is displayed is received, the medical image display apparatus 100 may increase the intensity of the ultrasound signal by a certain value. Otherwise, if a flick touch involving moving the finger downwards from the region where the icon 3405 is displayed, the medical image display apparatus 100 may decrease the intensity of the ultrasound signal by the certain value.

Upon receipt of a flick touch involving moving a finger to the right with respect to the icon 3405 as indicated by an arrow in the portion 4010, the medical image display apparatus 100 may select one of a plurality of parameters related to a medical image. The arrow in the portion 4010 may represent a user's flick touch for selecting a parameter.

As shown in portions 4010 of FIG. 40A and 4020 of FIG. 40B, when a single rightward flick touch on the icon 3405 is received, the medical image display apparatus 100 may select a depth parameter from among the plurality of parameters related to the medical image 3013. The medical image display apparatus 100 may display the selected depth parameter by indicating "Depth" on the icon 3405.

In a state shown in the portion 4020, to adjust the selected depth parameter, the user may input a flick touch on the icon 3405. If a flick touch involving moving the finger outwards and upwards from the region where the icon 3405 is displayed is received, the medical image display apparatus 100 may decrease the depth parameter by a certain value. Otherwise, if a flick touch involving moving the finger downwards from the region where the icon 3405 is displayed, the medical image display apparatus 100 may increase the depth parameter by the certain value.

As shown in portions 4010 of FIG. 40A, 4020 of FIG. 40B, and 4030 of FIG. 40C, when a second rightward flick touch on the icon 3405 is received, the medical image display apparatus 100 may select a parameter related to a frequency of an ultrasound signal from among the plurality of parameters related to the medical image 3013. The medical image display apparatus 100 may display the selected parameter by indicating "Freq" on the icon 3405.

In a state shown in the portion 4030, to adjust the parameter related to a frequency of an ultrasound signal, the user may input a flick touch on the icon 3405. If a flick touch involving moving the finger outwards and upwards from a region where the icon 3405 is displayed is received, the medical image display apparatus 100 may increase the parameter related to the frequency of the ultrasound signal by a certain value. Otherwise, if a flick touch involving moving the finger downwards from the region where the icon 3405 is displayed, the medical image display apparatus 100 may decrease the parameter by the certain value. An arrow in the portion 4030 represents a user's flick touch for increasing a value of the parameter related to the frequency of the ultrasound signal.

In addition, according to an exemplary embodiment, the medical image display apparatus 100 may select a UI having an operation depth suitable according to a size of the first region, from among a plurality of UIs.

Figure 41:
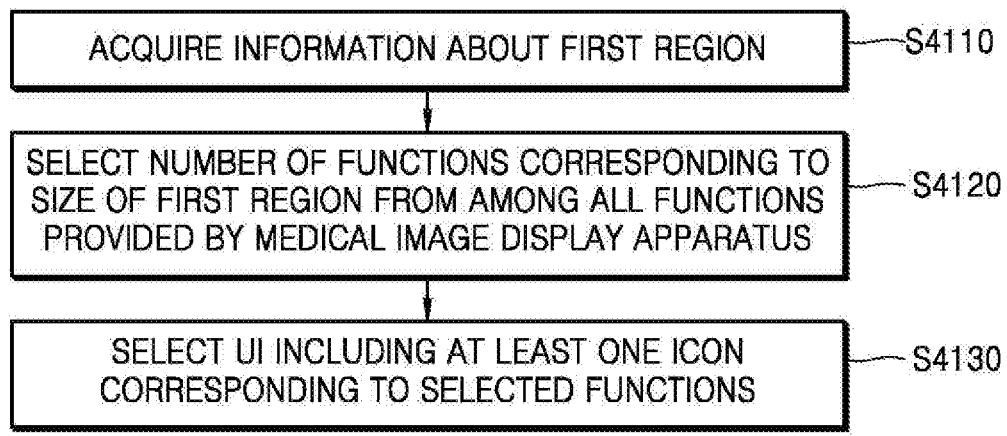
FIG. 41 is a flowchart of a method of selecting, by a medical image display apparatus, a UI for providing a number of functions according to a size of a first region, according to an exemplary embodiment.

FIG. 41 is a flowchart of a method of selecting, by the medical image display apparatus 100, a UI for providing a corresponding number of functions to a size of a first region, according to an exemplary embodiment;

The medical image display apparatus 100 may acquire information about a first region for defining a touch range on a touch screen that may be touched by the user's finger (S4110). Because operation S4110 illustrated in FIG. 41 corresponds to operation S510 illustrated in FIG. 5, the same descriptions as provided above with respect to operation S510 will be omitted below.

The medical image display apparatus 100 may acquire the information about the first region from a memory included therein, a memory of an external device, or an external server. In some exemplary embodiments, the medical image display apparatus 100 may acquire the information about the first region by analyzing a touch gesture received from the user in response to a guide image. In addition, the medical image display apparatus 100 may receive the information about the first region directly from the user.

The medical image display apparatus 100 may select a corresponding number of functions to a size of the first region from among all functions provided by the medical image display apparatus 100 (S4120).

Thus, as the size of the first region increases, the medical image display apparatus 100 may select more functions. As the size of the first region decreases, the medical image display apparatus 100 may select fewer functions.

The medical image display apparatus 100 may select a UI including at least one icon corresponding to the functions selected in operation S4121 (S4130).

As the size of the first region increases, the medical image display apparatus 100 may select a UI providing more functions.

Referring to FIGS. 30 and 32, the medical image display apparatus 100 displays a UI providing functions of adjusting a frequency of an ultrasound signal, adjusting a depth of penetration of an ultrasound signal, changing an operating mode, and capturing a medical image.

Referring to FIGS. 34, 36A, and 36B, the medical image display apparatus 100 displays a UI providing functions of adjusting intensity of an ultrasound signal, changing an operating mode, and capturing a medical image.

When a user's touch range is determined to be very narrow compared to the touch range shown in FIGS. 30, 32, 34, 36A, and 36B, the medical image display apparatus 100 may select a UI providing only a very small number of functions.

Figure 43:
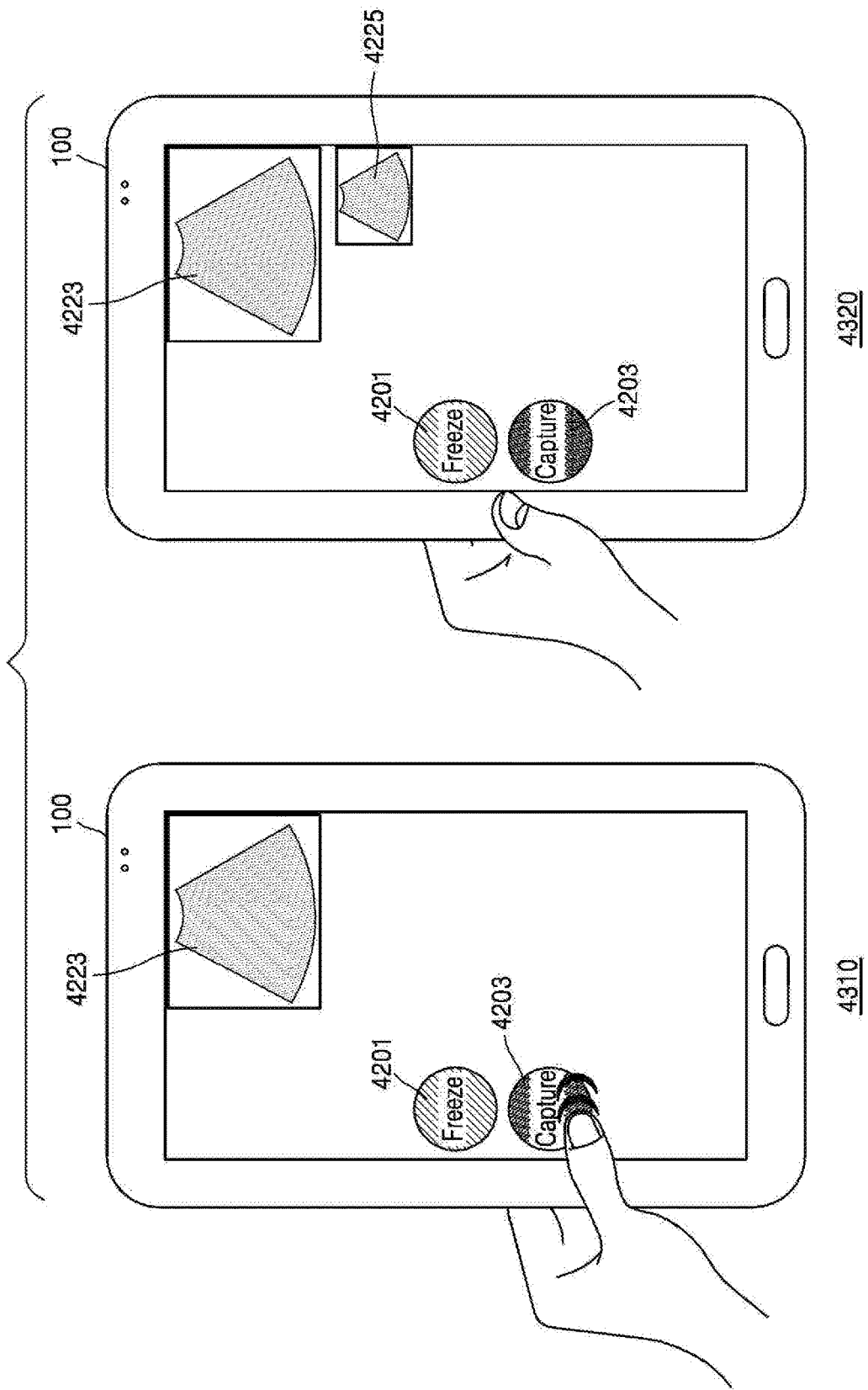

FIGS. 42 and 43 illustrate an example of a UI 4211 provided by a medical image display apparatus 100, according to an exemplary embodiment.

Referring to FIGS. 42 and 43, the medical image display apparatus 100 displays the UI 4211 configured to receive a touch and hold gesture or tap touch. In this case, the medical image display apparatus 100 is connected to the ultrasound diagnosis device 11 or the ultrasound probe 12.

As shown in FIGS. 42 and 43, when a user's touch range is very narrow, the medical image display apparatus 100 may the UI 4211 providing only a function of changing an operating mode of the medical image display apparatus 100 and a function of capturing a medical image 4213 (e.g., an ultrasound image).

As shown in a portion 4210, the medical image display apparatus 100 may display the medical image 4213 and the UI 4211 related to the medical image 4213. The UI 4211 may include icons 4201 and 4203 respectively corresponding to a function of changing an operating mode of the medical image display apparatus 100 and a function of capturing a medical image.

The user may input a touch and hold gesture with respect to the icon 4201 so that the medical image display apparatus 100 operates in a live mode.

As shown in the portion 4210, when the medical image display apparatus 100 operates in a live mode (i.e., the ultrasound probe 12 transmits or receives ultrasound signals at predetermined time intervals, and the medical image display apparatus 100 provides an ultrasound image in real-time), the medical image display apparatus 100 may indicate a current operating mode by displaying "Live" on the icon 4201.

When the touch and hold gesture with respect to the icon 4201 is detected, the medical image display apparatus 100 may control the ultrasound probe 12 to transmit ultrasound signals to an object at predetermined time intervals and receive echo signals from the object. The medical image display apparatus 100 may display the medical mage 4213 (e.g., the ultrasound image) in real-time while detecting the touch and hold gesture with respect to the icon 4201.

As shown in a portion 4220, the user may lift a finger off the icon 4201 in order to change an operating mode of the medical image display apparatus 100 from a live mode to a freeze mode.

If it is determined that the touch and hold gesture with respect to the icon 4201 is terminated, the medical image display apparatus 100 may change an operating mode from a live mode to a freeze mode. The medical image display apparatus 100 may display a current operating mode by indicating "Freeze" on the icon 4201.

When the touch and hold gesture with respect to the icon 3405 is terminated, the medical image display apparatus 100 may control the ultrasound probe 12 to stop transmitting or receiving ultrasound signals. Furthermore, the medical image display apparatus 100 may display an ultrasound still image 4223.

When the touch and hold gesture with respect to the icon 4201 indicated as "Freeze" is detected again, the medical image display apparatus 100 may change an operating mode from a freeze mode to a live mode.

As shown in a portion 4310 of FIG. 43, to capture the ultrasound still image 4223 being displayed, the user may input a tap touch on the icon 4203. When the tap touch with respect to the icon 4203 is received, the medical image display apparatus 100 may determine that a command for capturing a medical image has been received from the user.

As shown in a portion 4320, when the tap touch with respect to the icon 4203 is received, the medical image display apparatus 100 may further display reduced versions 4225 of the ultrasound still image 4223. Furthermore, the medical image display apparatus 100 may store the ultrasound still image 4223 in a memory.

According to an exemplary embodiment, as shown in FIGS. 42 and 43, when a user's touch range is very narrow, the medical image display apparatus 100 may be configured to support a UI providing only a minimum number of functions, thereby allowing the user to conveniently use the medical image display apparatus 100.

Figure 44:
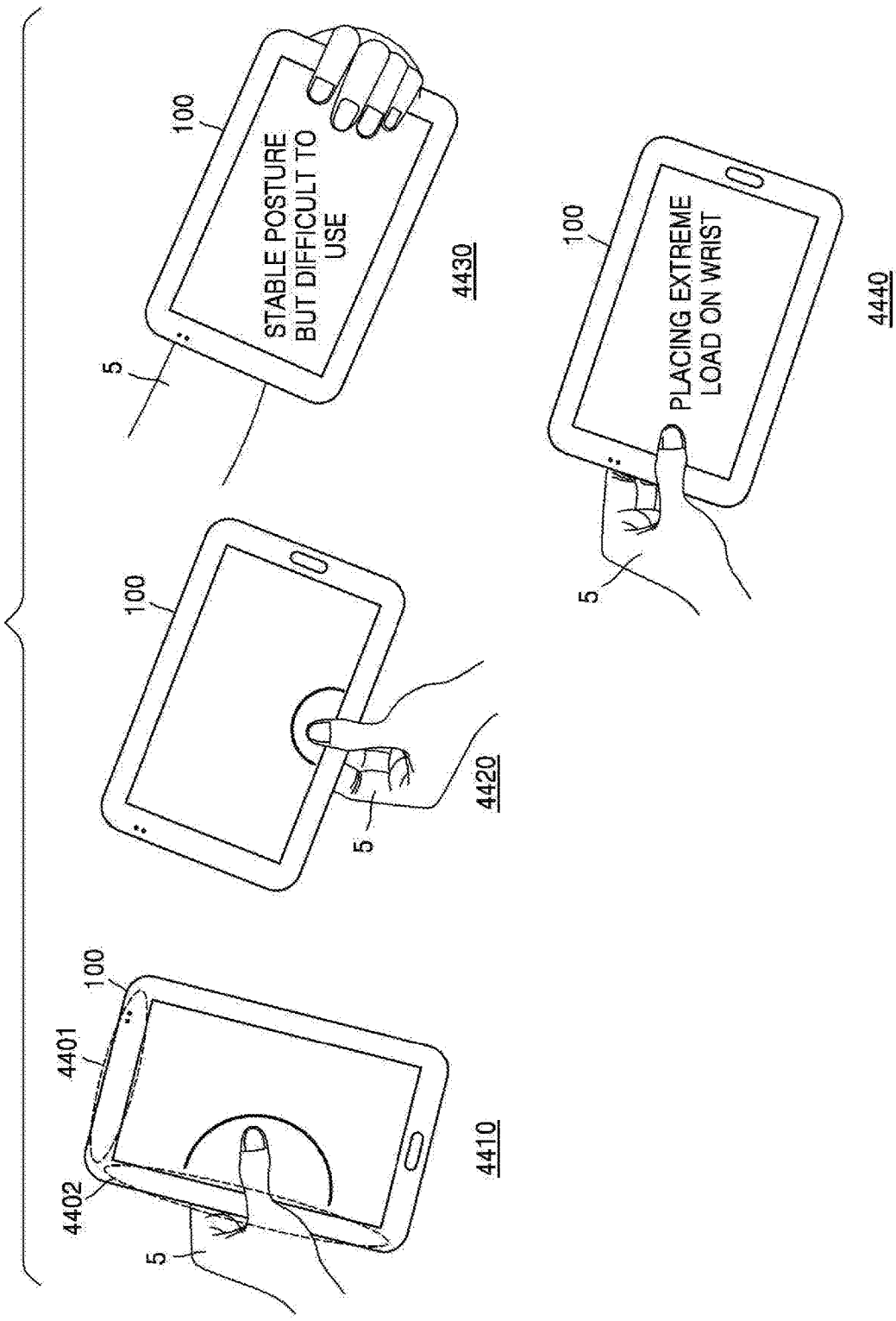
FIG. 44 is a diagram for explaining a reason for providing a UI based on a direction in which a medical image display apparatus displays content and a side of the medical image display apparatus where a user's hand is located.

In addition, as shown in FIG. 44, a finger-touchable range and the degree of ease of use of the medical image display apparatus 100 by the user may vary depending on a direction in which the medical image display apparatus 100 displays content and a position of a user's hand used to grip the medical image display apparatus 100.

FIG. 44 shows an example where the medical image display apparatus 100 is a device having a rectangular or semi-rectangular shape including a short first side 4401 and a long second side 4402.

As shown in a portion 4410, when the medical image display apparatus 100 displays content in a longitudinal direction and a user 5 grips the second side 4402 of the medical image display apparatus 100, a touch range of a finger of the user 5 may be relatively wide.

On the other hand, as shown in a portion 4420, when the medical image display apparatus 100 displays content in a transverse direction and the user 5 grips the second side 4402 of the medical image display apparatus 100, a touch range of a finger of the user 5 may become relatively narrow.

As shown in a portion 4430, the user 5 grips the medical image display apparatus 100 in a stable posture. However, if the user 5 grips the medical image display apparatus 100 in such a posture as shown in the portion 4430, the user may have difficulty in using the medical image display apparatus 100 by touching the touch screen (110 of FIG. 3) since it may be hard to move his or her fingers.

Maintaining a posture as shown in a portion 440 while gripping the medical image display apparatus 100 may be impractical because the posture places extreme loads on a wrist of the user 5.

Thus, according to an exemplary embodiment, the medical image display apparatus 100 may select a UI from among a plurality of UIs by further taking into account at least one of a direction in which the medical image display apparatus 100 displays content and a side of the medical image display apparatus 100 where a user's hand used to grip the medical image display apparatus 100 is located, thereby providing improved user convenience.

Figure 45:
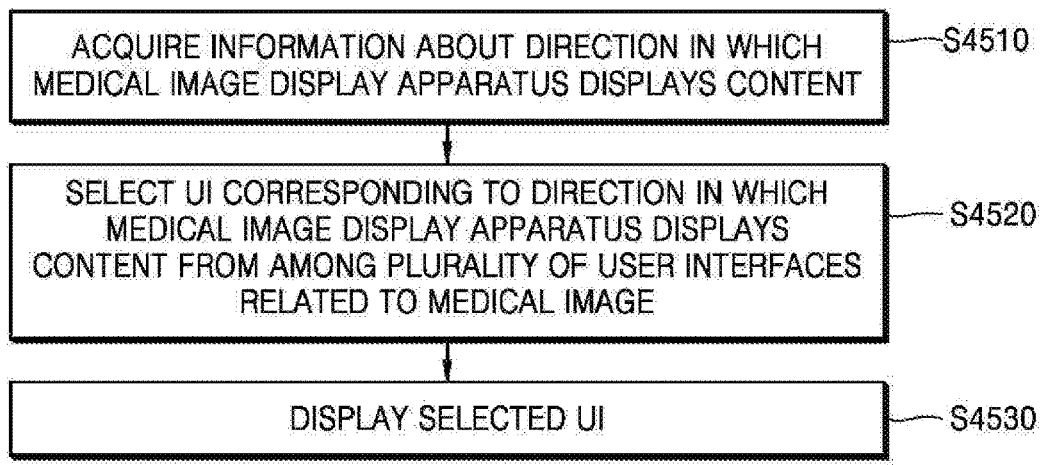
FIG. 45 is a flowchart of a method of providing a UI corresponding to a direction in which a medical image display apparatus displays content according to an exemplary embodiment.

FIG. 45 is a flowchart of a method of providing a UI corresponding to a direction in which the medical image display apparatus 100 displays content according to an exemplary embodiment.

Referring to FIG. 45, the medical image display apparatus 100 may acquire information about a direction in which the medical image display apparatus 100 displays content (S4510).

The medical image display apparatus 100 may acquire information about whether the medical image display apparatus 100 displays content in a longitudinal or transverse direction.

For example, the medical image display apparatus 100 may be a device having a rectangular or semi-rectangular shape including a short first side and a long second side. Displaying content in the longitudinal direction may mean arranging and displaying the content along the second side. Displaying content in the transverse direction may mean arranging and displaying the content along the first side.

The medical image display apparatus 100 may detect a slope thereof by using a sensing unit disposed therein. For example, the medical image display apparatus 100 may acquire motion information of the medical image display apparatus by using a magnetic sensor, an acceleration sensor, or a gyroscope sensor provided therein.

The medical image display apparatus 100 may determine whether to display content in a longitudinal or transverse direction according to a slope of the medical image display apparatus 100. Thus, the medical image display apparatus 100 may acquire information about the direction in which the medical image display apparatus 100 displays content, based on information about the slope of the medical image display apparatus 100.

The medical image display apparatus 100 may select a UI corresponding to the direction in which the medical image display apparatus 100 displays content, from among a plurality of UIs related to a medical image (S4520).

The plurality of UIs related to a medical image may include at least one of a GUI for setting a parameter related to a medical image, a GUI for controlling an external device or server connected to the medical image display apparatus 100, and a UI for displaying information about the medical image.

The medical image display apparatus 100 may display the UI selected in operation S4520 (S4530).

The medical image display apparatus 100 may display the selected UI at a position determined based on a position of a user's hand or finger.

Figure 46:
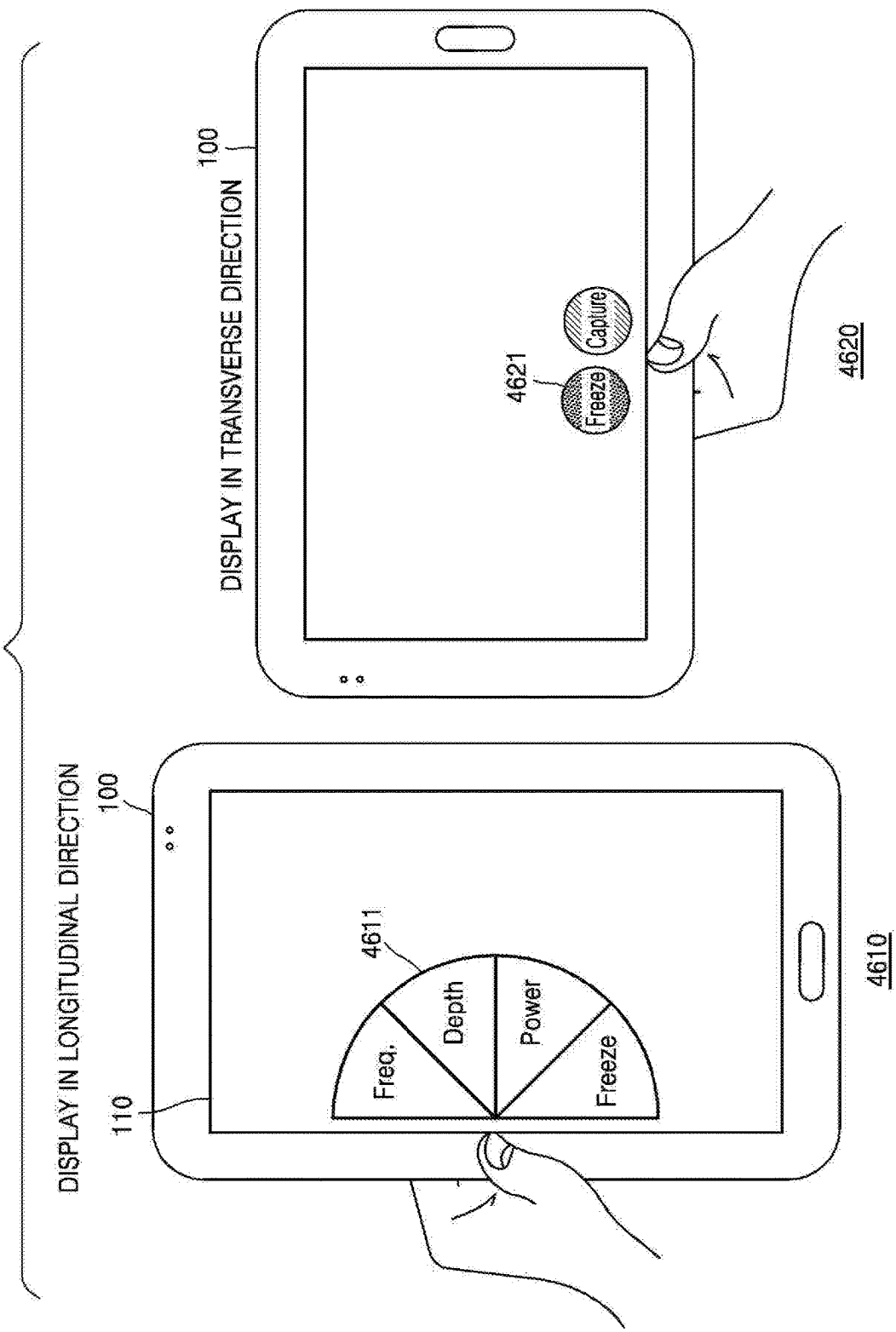
FIG. 46 illustrates examples of UIs provided based on a direction in which a medical image display apparatus displays content, according to an exemplary embodiment.

FIG. 46 illustrates examples of a plurality of first and second UIs 4611 and 4621 provided based on a direction in which a medical image display apparatus 100 displays content, according to an exemplary embodiment.

Referring to FIG. 46, the user grips a second side of the medical image display apparatus 100.

When the medical image display apparatus 100 displays content in a longitudinal direction, the medical image display apparatus 100 may select the first UI 4611 from among the first and second UIs 4611 and 4621. As shown in a portion 4610, when the first UI 4611 is selected, the medical image display apparatus 100 may display the selected first UI 4611 on a touch screen 110.

When the medical image display apparatus 100 displays content in a transverse direction, the medical image display apparatus 100 may select the second UI 4621 from among the first and second UIs 4611 and 4621. As shown in a portion 4620, when the second UI 4621 is selected, the medical image display apparatus 100 may display the selected second UI 4621 on the touch screen 110.

As shown in FIG. 46, the medical image display apparatus 100 may select UIs having different sizes based on a direction in which the medical image display apparatus 100 displays content.

When the user grips the second side of the medical image display apparatus 100 that displays content in the longitudinal direction, a finger-touchable range may be greater than when the user grips the second side of the medical image display apparatus 100 that displays content in the transverse direction.

When the medical image display apparatus 100 displays content in the longitudinal direction, the medical image display apparatus 100 may select the first UI 4611, which may have a larger size from among the first and second UIs 4611 and 4621. When the medical image display apparatus 100 displays the content in the transverse direction, the medical image display apparatus 100 may select the second UI 4621 having a smaller size from among the first and second UIs 4611 and 4621.

Furthermore, as shown in FIG. 46, the medical image display apparatus 100 may select a UI configured to receive a different type of touch gesture based on a direction in which the medical image display apparatus 100 displays content.

The medical image display apparatus 100 may select from among different types of touch gestures a type of touch gesture corresponding to a direction in which the medical image display apparatus 100 displays content and select a UI configured to receive the selected touch gesture.

For example, a greater region on the touch screen 110 may be required for the medical image display apparatus 100 to detect a swipe touch and a flick touch than to detect a tap touch and a touch and hold gesture.

Thus, when a finger-touchable range increases according to a direction in which the medical image display apparatus 100 displays content, the medical image display apparatus 100 may select the first UI 4611 configured to receive a swipe touch and a flick touch. When a finger-touchable range decreases according to a direction in which the medical image display apparatus 100 displays the content, the medical image display apparatus 100 may select the second UI 4621, which may be configured to receive only a tap touch and a touch and hold gesture.

Furthermore, as shown in FIG. 46, the medical image display apparatus 100 may select UIs that provide a different number of functions based on a direction in which the medical image display apparatus 100 displays content.

The first UI 4611 may be a UI including icons corresponding to a function of adjusting a frequency of an ultrasound signal, a function of adjusting a depth of penetration of an ultrasound signal, and a function of changing an operating mode.

The second UI 4621 may be a UI including icons corresponding to a function of changing an operating mode and a function of capturing a medical image.

Thus, when a finger-touchable range increases according to a direction in which the medical image display apparatus 100 displays content, the medical image display apparatus 100 may select the first UI 4611 providing a large number of functions. When a finger-touchable range decreases according to a direction in which the medical image display apparatus 100 displays the content, the medical image display apparatus 100 may select the second UI 4621 providing a small number of functions.

In addition, the medical image display apparatus 100 may provide a UI by further taking into account a size of a finger-touchable range as well as a direction in which the medical image display apparatus 100 displays content.

Figure 47:
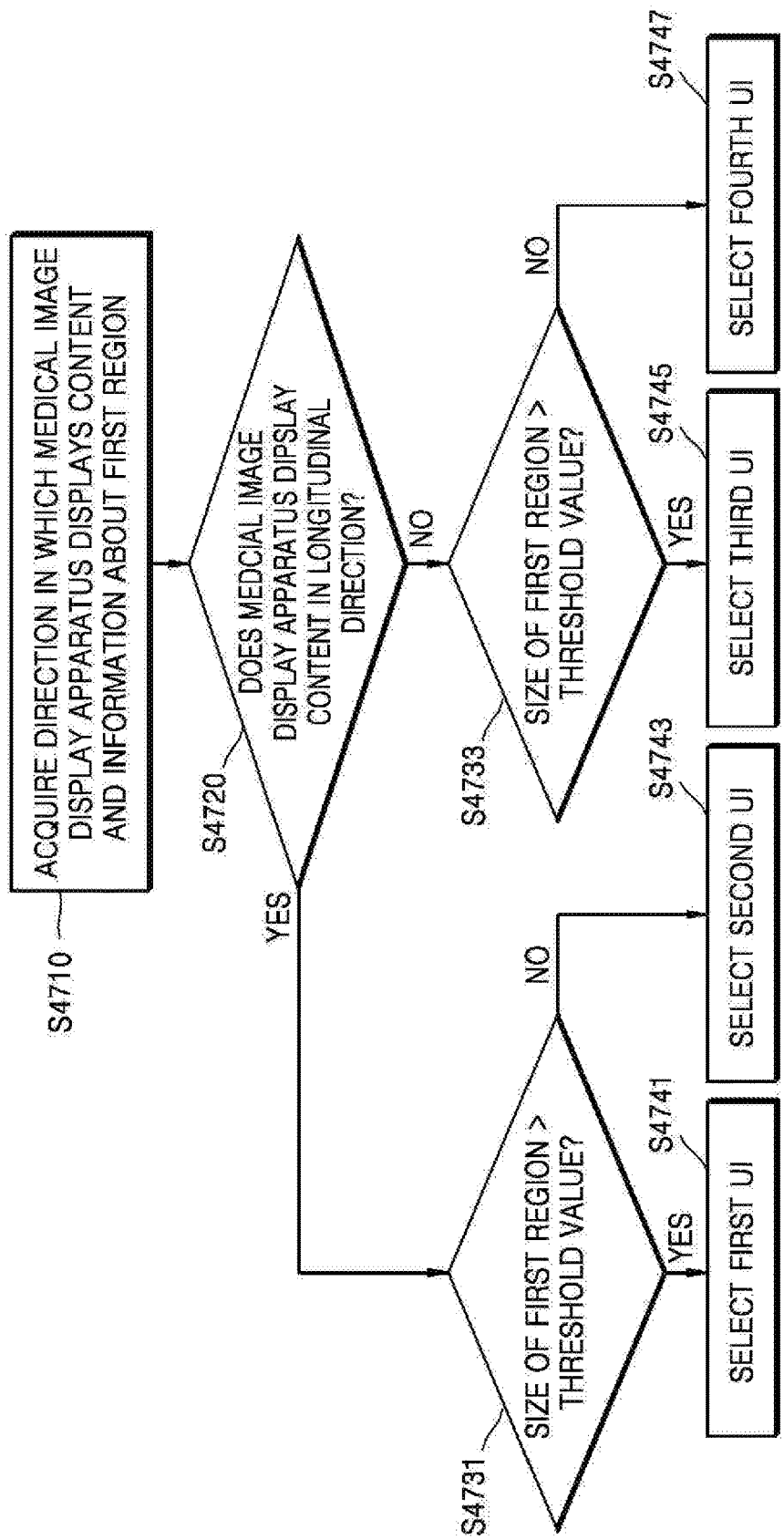
FIG. 47 is a flowchart of a method of providing a UI corresponding to a direction in which a medical image display apparatus displays content and a size of a first region, according to an exemplary embodiment.

FIG. 47 is a flowchart of a method of providing a UI corresponding to a direction in which the medical image display apparatus 100 displays content and a size of a first region, according to an exemplary embodiment.

In some exemplary embodiments, operation S4710 illustrated in FIG. 47 may be included in operation S510 illustrated in FIG. 5, and operations S4720, S4731, S4733, S4741, S4743, S4745, and S4747 may be included in operation S520 illustrated in FIG. 5. Thus, the same descriptions as provided above with respect to FIG. 5 will be omitted here. Further, in some exemplary embodiments, operation S4710 may be included in S4510 illustrated in FIG. 45, and operations S4720, S4731, S4733, S4741, S4743, S4745, and S4747 may be included in operation S4520 illustrated in FIG. 45. In this case, the same descriptions as provided above with respect to FIG. 45 will be omitted here.

The medical image display apparatus 100 may acquire information about a direction in which the medical image display apparatus 100 displays content and information about a first region for defining a finger-touchable range (S4710).

The medical image display apparatus 100 may acquire information about whether the medical image display apparatus 100 displays content in a longitudinal or transverse direction. For example, the medical image display apparatus may acquire information about the direction in which the medical image display apparatus 100 displays content based on information about a slope of the medical image display apparatus 100.

The medical image display apparatus 100 may acquire the information about the first region from a memory included in the medical image display apparatus 100, a memory of an external device, or an external server. In some exemplary embodiments, the medical image display apparatus 100 may acquire the information about the first region by analyzing a touch gesture received from the user in response to a guide image. In addition, the medical image display apparatus 100 may receive the information about the first region directly from the user.

The medical image display apparatus 100 may determine whether the direction in which the medical image display apparatus 100 displays the content is a longitudinal direction (S4720).

When the direction in which the medical image display apparatus 100 displays the content is the longitudinal direction, the medical image display apparatus 100 may compare a size of the first region to a threshold value (S4731). The threshold value may be predetermined as a default value or may be set by the user. For example, the threshold value is a value corresponding to a size of a first UI.

If the direction in which the medical image display apparatus 100 displays the content is the longitudinal direction and the size of the first region is greater than the threshold value, the medical image display apparatus 100 may select the first UI from among a plurality of UIs (S4741).

If the direction in which the medical image display apparatus 100 displays the content is the longitudinal direction and the size of the first region is less than or equal to the threshold value, the medical image display apparatus 100 may select a second UI from among the plurality of UIs (S4743).

When the direction in which the medical image display apparatus 100 displays the content is a transverse direction, the medical image display apparatus 100 may compare the size of the first region to the threshold value (S4733).

If the medical image display apparatus 100 displays the content in the transverse direction and the size of the first region is greater than the threshold value, the medical image display apparatus 100 may select a third UI from among the plurality of UIs (S4745).

If the medical image display apparatus 100 displays the content in the transverse direction and the size of the first region is less than or equal to the threshold value, the medical image display apparatus 100 may select a fourth UI from among the plurality of UIs (S4747).

FIGS. 48A and 48B illustrate examples of a plurality of first through fourth UIs 4811, 4821, 4831, and 4841, which may be provided based on a direction in which the medical image display apparatus 100 displays content and a size of a first region, according to an exemplary embodiment.

Referring to FIGS. 48A and 48B, a user may grip a second side of the medical image display apparatus 100. Furthermore, the medical image display apparatus 100 acquires a maximum finger-touchable distance as information about the first region. In other words, the medical image display apparatus 100 may acquire the maximum finger-touchable distance as a value indicative of the size of the first region.

As shown in FIGS. 48A and 48B, the medical image display apparatus 100 may select UIs having different sizes based on a direction in which the medical image display apparatus 100 displays content and the size of the first region Furthermore, as shown in FIGS. 48A and 48B, the medical image display apparatus 100 may select UIs configured to receive different types of touch gestures based on the direction in which the medical image display apparatus 100 displays the content and the size of the first region.

Referring to FIG. 48A, when the medical image display apparatus 100 displays content in a longitudinal direction and a maximum finger-touchable distance is greater than 5 cm, the medical image display apparatus 100 may select the first UI 4811 from among of the first through fourth UIs 4811, 4821, 4831, and 4841. As shown in a portion 4810, when the first UI 4811 is selected, the medical image display apparatus 100 may display the selected first UI 4811 on the touch screen (110 of FIG. 3).

On the other hand, when the medical image display apparatus 100 displays content in the longitudinal direction and the maximum finger-touchable distance is less than or equal to 5 cm, the medical image display apparatus 100 may select the second UI 4821 from among of the first through fourth UIs 4811, 4821, 4831, and 4841. As shown in a portion 4820, when the second UI 4821 is selected, the medical image display apparatus 100 may display the selected second UI 4821 on the touch screen 110.

Referring to FIG. 48B, when the medical image display apparatus 100 displays content in a transverse direction and a maximum finger-touchable distance is greater than 5 cm, the medical image display apparatus 100 may select the third UI 4831 from among first through fourth UIs 4811, 4821, 4831, and 4841. As shown in a portion 4830, when the third UI 4831 is selected, the medical image display apparatus 100 may display the selected third UI 4831 on the touch screen 110.

On the other hand, when the medical image display apparatus 100 displays content in the transverse direction and the maximum finger-touchable distance is less than or equal to 5 cm, the medical image display apparatus 100 may select the fourth UI 4841 from among the first through fourth UIs 4811, 4821, 4831, and 4841. As shown in a portion 4840, when the fourth UI 4841 is selected, the medical image display apparatus 100 may display the selected fourth UI 4841 on the touch screen 110.

Figure 49:
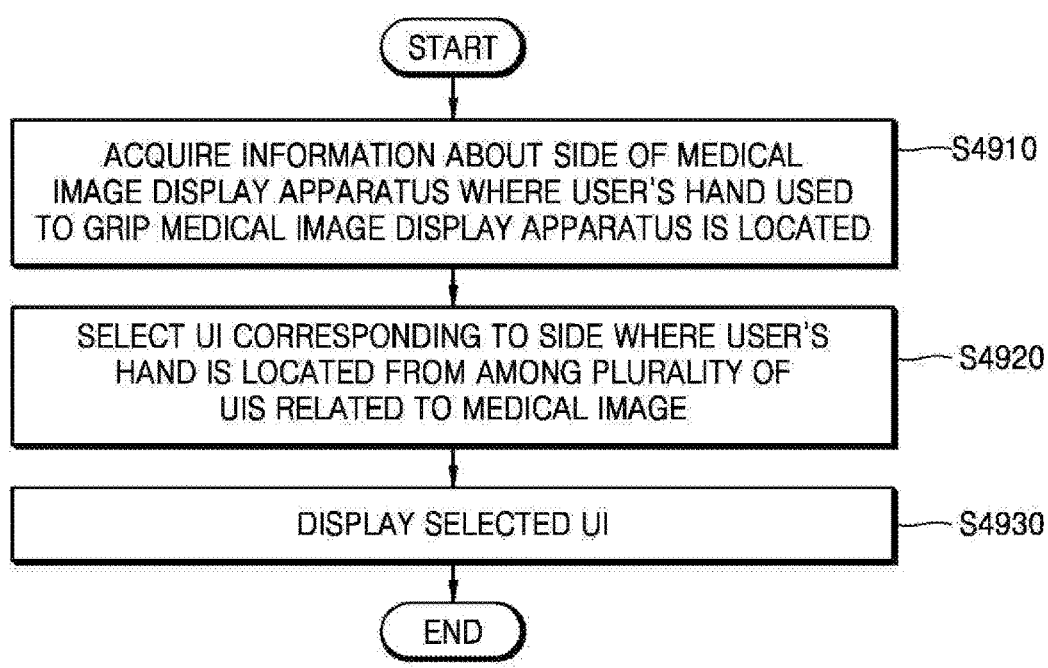
FIG. 49 is a flowchart of a method of providing, by a medical image display apparatus, a UI corresponding to a side of the medical image display apparatus where a user's hand is located, according to an exemplary embodiment.

FIG. 49 is a flowchart of a method of providing, by the medical image display apparatus 100, a UI corresponding to a side of the medical image display apparatus 100 where a user's hand is located, according to an exemplary embodiment.

Referring to FIG. 49, the medical image display apparatus 100 may acquire information about a side of the medical image display apparatus 100 where a user's hand used to grip the medical image display apparatus 100 is located (S4910).

For example, the medical image display apparatus 100 may be a device having a rectangular or semi-rectangular shape including a short first side and a long second side 4402. The medical image display apparatus 100 may acquire information about whether the user's hand is located on the first or second side thereof.

The medical image display apparatus 100 may acquire information about a side of the medical image display apparatus 100 where the user's hand used to grip the medical image display apparatus 100 is located by using a sensing unit disposed therein. For example, the medical image display apparatus 100 may detect a position of the user's hand used to grip the medical image display apparatus 100 via a sensor disposed on the bezel surrounding the touch screen 110. In some exemplary embodiments, the medical image display apparatus 100 may acquire information about a side thereof where the user's hand is located based on a position of a user's finger touching the touch screen 110.

The medical image display apparatus 100 may select from among a plurality of UIs related to a medical image a UI corresponding to a side of the medical image display apparatus 100 where the user's hand is located (S4920)

The plurality of UIs related to a medical image may include at least one of a GUI for setting parameters related to the medical image, a GUI for controlling an external device or server connected to the medical image display apparatus 100, and a UI for displaying information about the medical image.

The medical image display apparatus 100 may display a UI selected in operation S4920 previously (S4930).

The medical image display apparatus 100 may display the selected UI at a position determined based on a position of the user's hand or finger.

Figure 50:
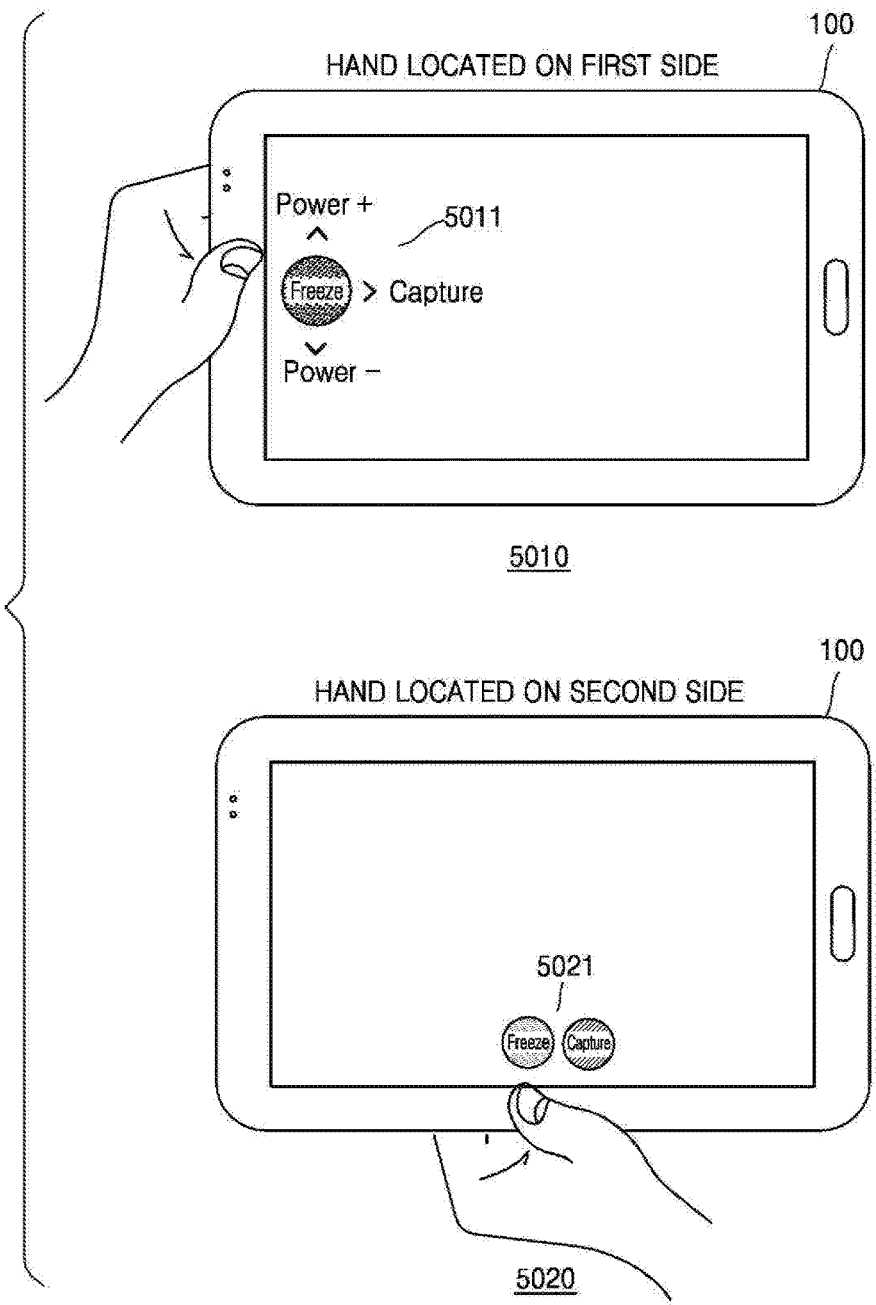
FIG. 50 illustrates examples of UIs provided based on a side of a medical image display apparatus where a user's hand is located, according to an exemplary embodiment.

FIG. 50 illustrates examples of a plurality of first and second UIs 5011 and 5021 provided based on a side of a medical image display apparatus 100 where a user's hand is located, according to an exemplary embodiment.

Referring to FIG. 50, the medical image display apparatus 100 displays content in a transverse direction.

When a user's hand is located on a first side of the medical image display apparatus 100, the medical image display apparatus 100 may select the first UI 5011 from among of the first and second UIs 5011 and 5021. As shown in a portion 5010, when the first UI 5011 is selected, the medical image display apparatus 100 may display the selected first UI 5011 on the touch screen 110.

On the other hand, when the user's hand is located on a second side of the medical image display apparatus 100, the medical image display apparatus 100 may select the second UI 5021 from among the first and second UIs 5011 and 5021. As shown in a portion 5020, when the second UI 5021 is selected, the medical image display apparatus 100 may display the selected second UI 5021 on the touch screen 110.

As shown in FIG. 50, the medical display apparatus 100 may select UIs having different sizes based on a side of the medical image display apparatus where the user's hand is located.

When the user grips the first side of the medical display apparatus 100 that displays content in the transverse direction, a finger-touchable range is greater than when the user grips the second side of the medical image display apparatus 100 that displays content in the transverse direction.

When the user grips the first side of the medical image display apparatus 100, the medical image display apparatus 100 may select the first UI 5011 having a larger size from among the first and second UIs 5011 and 5021. When the user grips the second side of the medical image display apparatus 100, the medical image display apparatus 100 may select the second UI 5021 having a smaller size from among the first and second UIs 5011 and 5021.

Furthermore, as shown in FIG. 50, the medical image display apparatus 100 may select UIs configured to receive different types of touch gestures based on a side of the medical image display apparatus where the user's hand is located.

The medical image display apparatus 100 may select from among different types of touch gestures a type of touch gesture corresponding to a side of the medical image display apparatus 100 where the user's hand is located and select a UI configured to receive the selected touch gesture.

For example, a greater region on the touch screen 110 may be required for the medical image display apparatus 100 to detect a flick touch than to detect a tap touch and a touch and hold gesture. Thus, when a finger-touchable range increases according to a side of the medical image display apparatus 100 where the user's hand is located, the medical image display apparatus 100 may select the first UI 5011 configured to receive a tap touch, a touch and hold gesture, and a flick touch. When a touch range of the user's finger decreases according to a side of the medical image display apparatus 100 where the user's hand is located, the medical image display apparatus 100 may select the second UI 5021 configured to receive only a tap touch and a touch and hold gesture.

Furthermore, as shown in FIG. 50, the medical image display apparatus 100 may select UIs that provide a different number of functions based on a side of the medical image display apparatus 100 where the user's hand is located.

The first UI 5011 may include icons corresponding to a function of adjusting intensity of an ultrasound signal, a function of changing an operating mode, and a function of capturing a medical image.

The second UI 5021 may include icons corresponding to a function of changing an operating mode and a function of capturing a medical image.

When a finger-touchable range increases according to a side of the medical image display apparatus 100 where the user's hand is located, the medical image display apparatus 100 may select the first UI 5011 providing a large number of functions. When a touch range of the user's finger decreases according to a side of the medical image display apparatus 100 where the user's hand is located, the medical image display apparatus 100 may select the second UI 5021 providing a small number of functions.

In addition, the medical image display apparatus 100 may provide a UI by further taking into account a size of a finger-touchable range as well as a side of the medical image display apparatus 100 where the user's hand is located.

Figure 51:
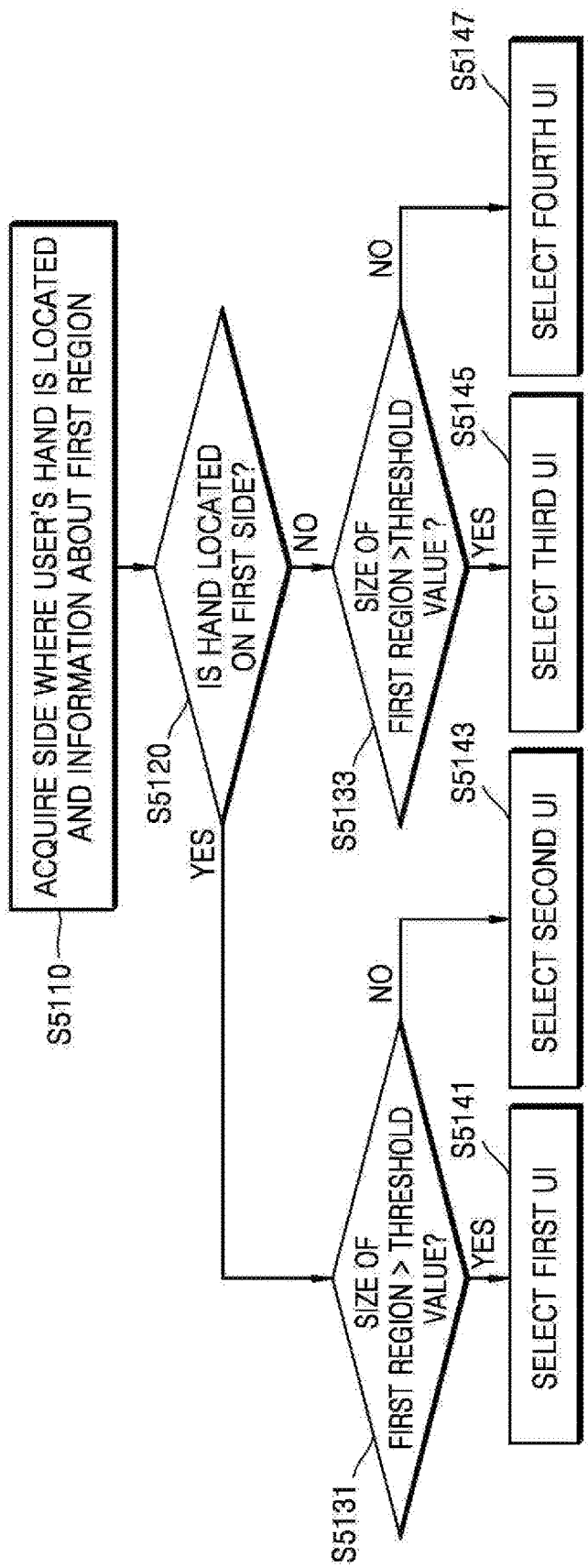
FIG. 51 is a flowchart of a method of providing, by a medical image display apparatus, a UI corresponding to a side of the medical image display apparatus where a user's hand is located and a size of a first region, according to an exemplary embodiment.

FIG. 51 is a flowchart of a method of providing, by the medical image display apparatus 100, a UI corresponding to a side of the medical image display apparatus 100 where a user's hand is located and a size of a first region, according to an exemplary embodiment.

In some exemplary embodiments, operation S5110 illustrated in FIG. 51 may be included in operation S510 illustrated in FIG. 5, and operations S5120, S5131, S5133, S5141, S5143, S5145, and S5147 may be included in operation S520 illustrated in FIG. 5. Thus, the same descriptions as provided above with respect to FIG. 5 will be omitted here. Further, in some exemplary embodiments, operation S5110 may be included in S4910 illustrated in FIG. 49, and operations S5120, S5131, S5131, S5141, S5143, S5145, and S5147 may be included in operation S4920 illustrated in FIG. 49. In this case, the same descriptions as provided above with respect to FIG. 49 will be omitted here.

The medical image display apparatus 100 may acquire information about a side of the medical image display apparatus 100 where a user's hand is located and information about a first region for defining a finger-touchable range (S5110).

The medical image display apparatus 100 may acquire information about whether the user's hand is located on a first or second side of the medical image display apparatus 100.

The medical image display apparatus 100 may acquire the information about the side of the medical image display apparatus 100 where the user's hand is located by using a sensing unit disposed therein.

The medical image display apparatus 100 may acquire the information about the first region from a memory included in the medical image display apparatus 100, a memory of an external device, or an external server. In some exemplary embodiments, the medical image display apparatus 100 may acquire the information about the first region by analyzing a touch gesture received from the user in response to a guide image. In addition, the medical image display apparatus 100 may receive the information about the first region directly from the user.

The medical image display apparatus 100 may determine whether the user's hand used to grip the medical image display apparatus 100 is located on a first side of the medical image display apparatus 100 (S5120).

When the user's hand is located on the first side of the medical image display apparatus 100, the medical image display apparatus 100 may compare a size of the first region to a threshold value (S5131). The threshold value may be predetermined as a default value or may be set by the user. For example, the threshold value is a value corresponding to a size of a first UI.

If the user's hand is located on the first side of the medical image display apparatus 100 and the size of the first region is greater than the threshold value, the medical image display apparatus 100 may select the first UI from among a plurality of UIs (S5141).

If the user's hand is located on the first side of the medical image display apparatus 100 and the size of the first region is less than or equal to the threshold value, the medical image display apparatus 100 may select a second UI from among the plurality of UIs (S5143).

When the user's hand is not located on the first side of the medical image display apparatus 100, that is, the user's hand is located on a second side thereof, the medical image display apparatus 100 may compare the size of the first region to the threshold value (S5133).

If the user's hand is located on the second side of the medical image display apparatus 100 and the size of the first region is greater than the threshold value, the medical image display apparatus 100 may select a third UI from among the plurality of UIs (S5145).

If the user's hand is located on the second side of the medical image display apparatus 100 and the size of the first region is less than or equal to the threshold value, the medical image display apparatus 100 may select a fourth UI from among the plurality of UIs (S5147).

Figure 52A:
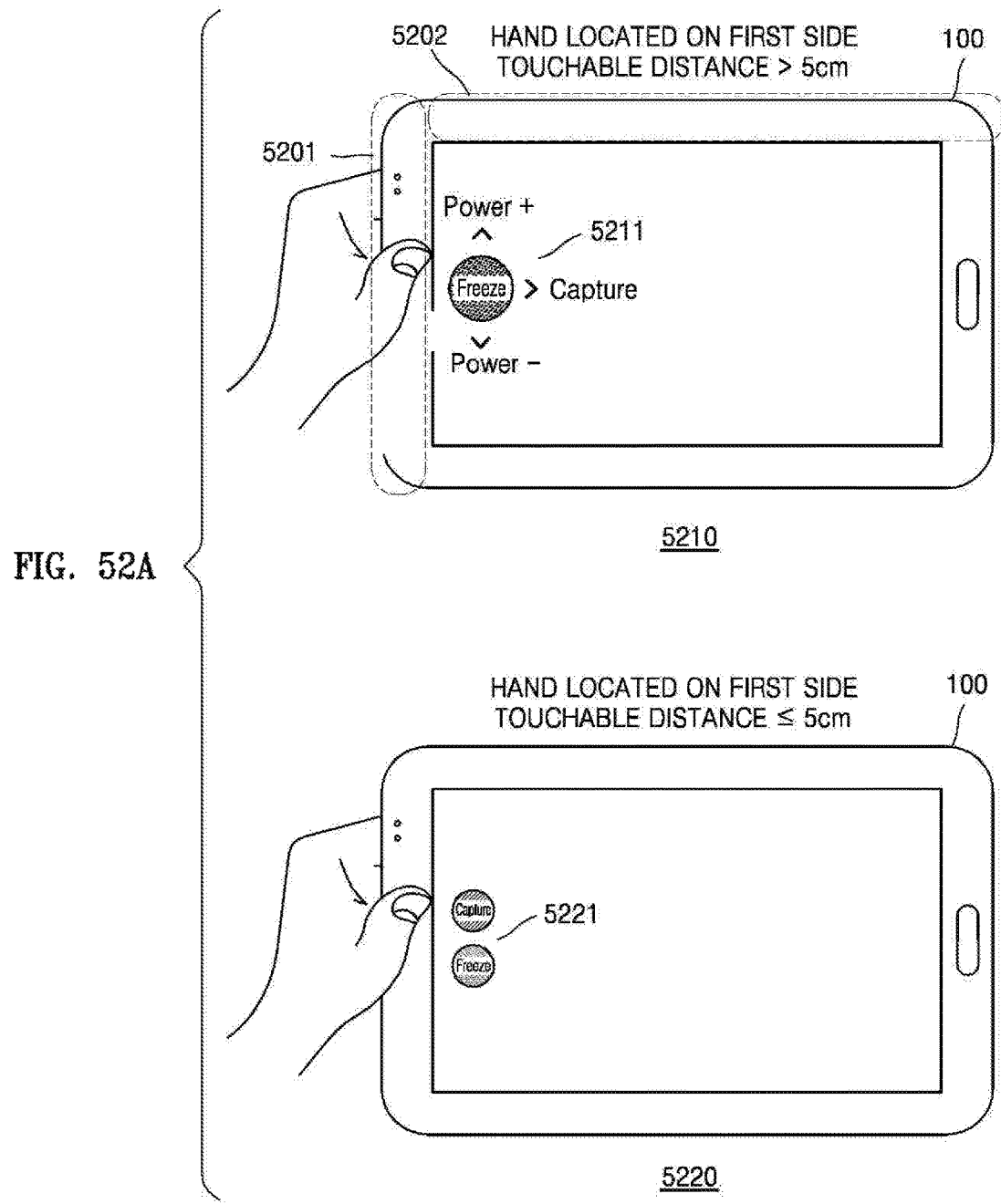
FIG. 52A and FIG. 52B illustrate examples of UIs provided based on a side of a medical image display apparatus where a user's hand is located and a size of a first region, according to an exemplary embodiment.
Figure 52B:
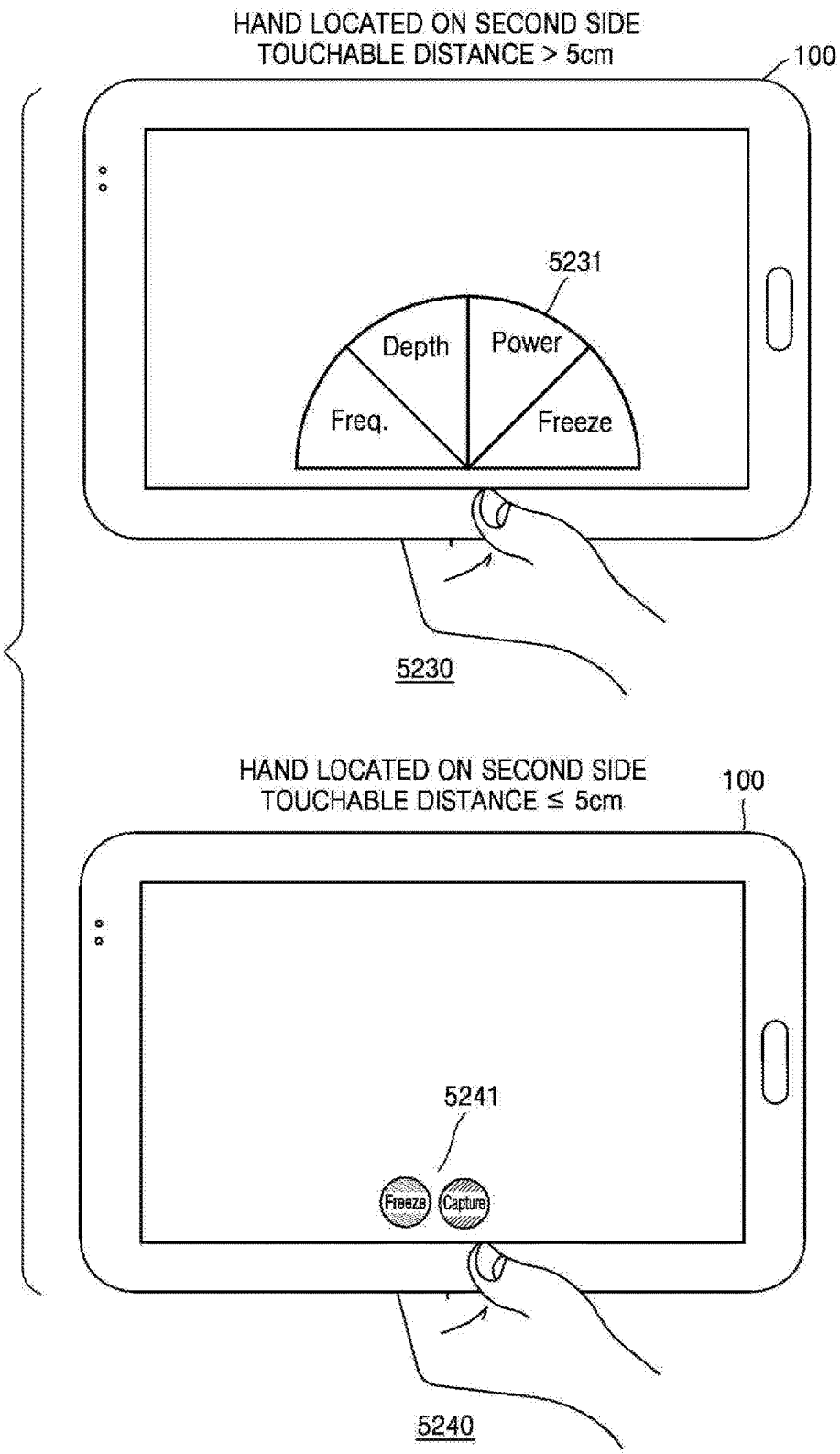

FIGS. 52A and 52B illustrate examples of a plurality of first through fourth UIs 5211, 5221, 5231, and 5241 provided based on a side of a medical image display apparatus 100 where a user's hand is located and a size of a first region, according to an exemplary embodiment.

Referring to FIGS. 52A and 52B, the medical image display apparatus may display content in a transverse direction. Furthermore, the medical image display apparatus 100 may acquire a maximum finger-touchable distance as information about the first region. In other words, the medical image display apparatus 100 may acquire the maximum finger-touchable distance as a value indicative of the size of the first region.

As shown in FIGS. 52A and 52B, the medical image display apparatus 100 may select UIs having different sizes based on a side of the medical image display apparatus 100 on which a user's hand is located and the size of the first region Furthermore, as shown in FIGS. 52A and 52B, the medical image display apparatus 100 may select UIs configured to receive different types of touch gestures based on a side of the medical image display apparatus 100 where the user's hand is located and the size of the first region.

Referring to FIG. 52A, when the user's hand is located on a first side 5201 of the medical image display apparatus 100 and a maximum finger-touchable distance is greater than 5 cm, the medical image display apparatus 100 may select the first UI 5211 from among the first through fourth UIs 5211, 5221, 5231, and 5241. As shown in a portion 5210, when the first UI 5211 is selected, the medical image display apparatus 100 may display the selected first UI 5211 on the touch screen (110 of FIG. 3).

On the other hand, when the user's hand is located on the first side 5201 of the medical image display apparatus 100 and the maximum finger-touchable distance is less than or equal to 5 cm, the medical image display apparatus 100 may select the second UI 5221 from among of the first through fourth UIs 5211, 5221, 5231, and 5241. As shown in a portion 5220, when the second UI 5221 is selected, the medical image display apparatus 100 may display the selected second UI 5221 on the touch screen 110.

Referring to FIG. 52B, when the user's hand is located on a second side 5202 of the medical image display apparatus 100 and a maximum finger-touchable distance is greater than 5 cm, the medical image display apparatus 100 may select the third UI 5231 from among the first through fourth UIs 5211, 5221, 5231, and 5241. As shown in a portion 5230, when the third UI 5231 is selected, the medical image display apparatus 100 may display the selected third UI 5231 on the touch screen 110.

On the other hand, when the user's hand is located on the second side 5202 of the medical image display apparatus 100 and the maximum finger-touchable distance is less than or equal to 5 cm, the medical image display apparatus 100 may select the fourth UI 5241 from among the first through fourth UIs 5211, 5221, 5231, and 5241. As shown in a portion 5240, when the fourth UI 5241 is selected, the medical image display apparatus 100 may display the selected fourth UI 5241 on the touch screen 110.

When the user uses the medical image display apparatus 100 with one hand, a touch range of a finger of the user's hand used to grip the medical image display apparatus 100 may be limited. Thus, according to an exemplary embodiment, the medical image display apparatus 100 may display a UI based on a position of a user's touch. The medical image display apparatus 100 may display a UI at a position determined based on a position of a user's hand or finger.

To ensure a medical image provided via the medical image display apparatus 100 may be used for diagnosis or treatment of a disease, the medical image has to be provided to the user without distortion. For example, if a UI is displayed to overlap a medical image, accuracy of diagnosis and treatment of a disease may be degraded. Thus, the medical image display apparatus 100 may change a position where the medical image is to be displayed so that a selected UI and the medical image does not overlap each other, based on a position where the selected UI is displayed.

Figure 53:
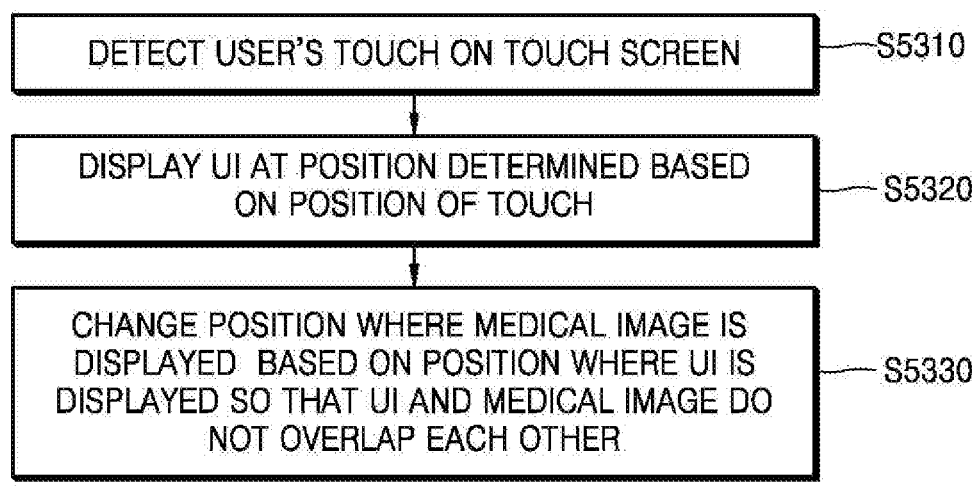
FIG. 53 is a flowchart of a method of displaying, by a medical image display apparatus, a UI based on a position of a user's touch according to an exemplary embodiment.

FIG. 53 is a flowchart of a method of displaying, by the medical image display apparatus 100, a UI based on a position of user's touch according to an exemplary embodiment.

Because operations S5310, S5320, and S5330 may be included in operation S530 illustrated in FIG. 5, the same descriptions as provided above with respect to FIG. 5 will be omitted here.

The medical image display apparatus 100 may detect a user's touch on a touch screen (S5310).

The medical image display apparatus 100 may display a UI at a position determined based on a position of user's touch (S5320).

As illustrated in FIG. 5, the medical image display apparatus 100 may select a UI corresponding to a size of a first region from among a plurality of UIs and display the selected UI at the determined position.

Figure 54:
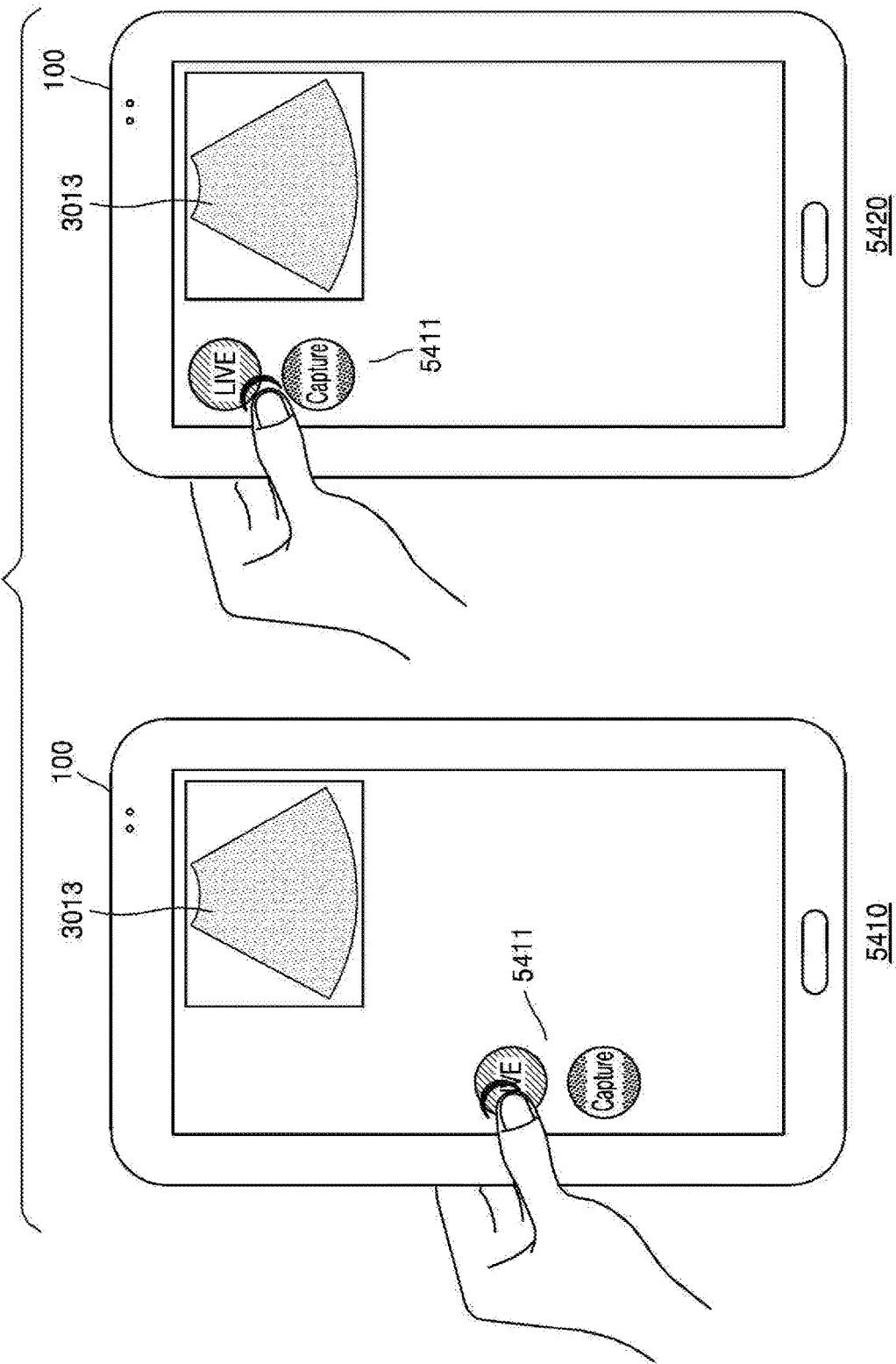
FIG. 54 illustrates examples of UIs being displayed by a medical image display apparatus at a position that changes according to a position of a user's touch, according to an exemplary embodiment.

As shown in a portion 5410 of FIG. 54, the medical image display apparatus 100 may display a UI 5411 at a position of user's touch where the user's touch is detected. As shown in a portion 5420, when the position of user's touch changes, the medical image display apparatus 100 may display the UI 5411 at the changed position of user's touch.

Based on the position where the UI is displayed, the medical image display apparatus 100 may change a position where a medical image is to be displayed so that the medical image and the UI do not overlap each other (S5330).

Figure 55:
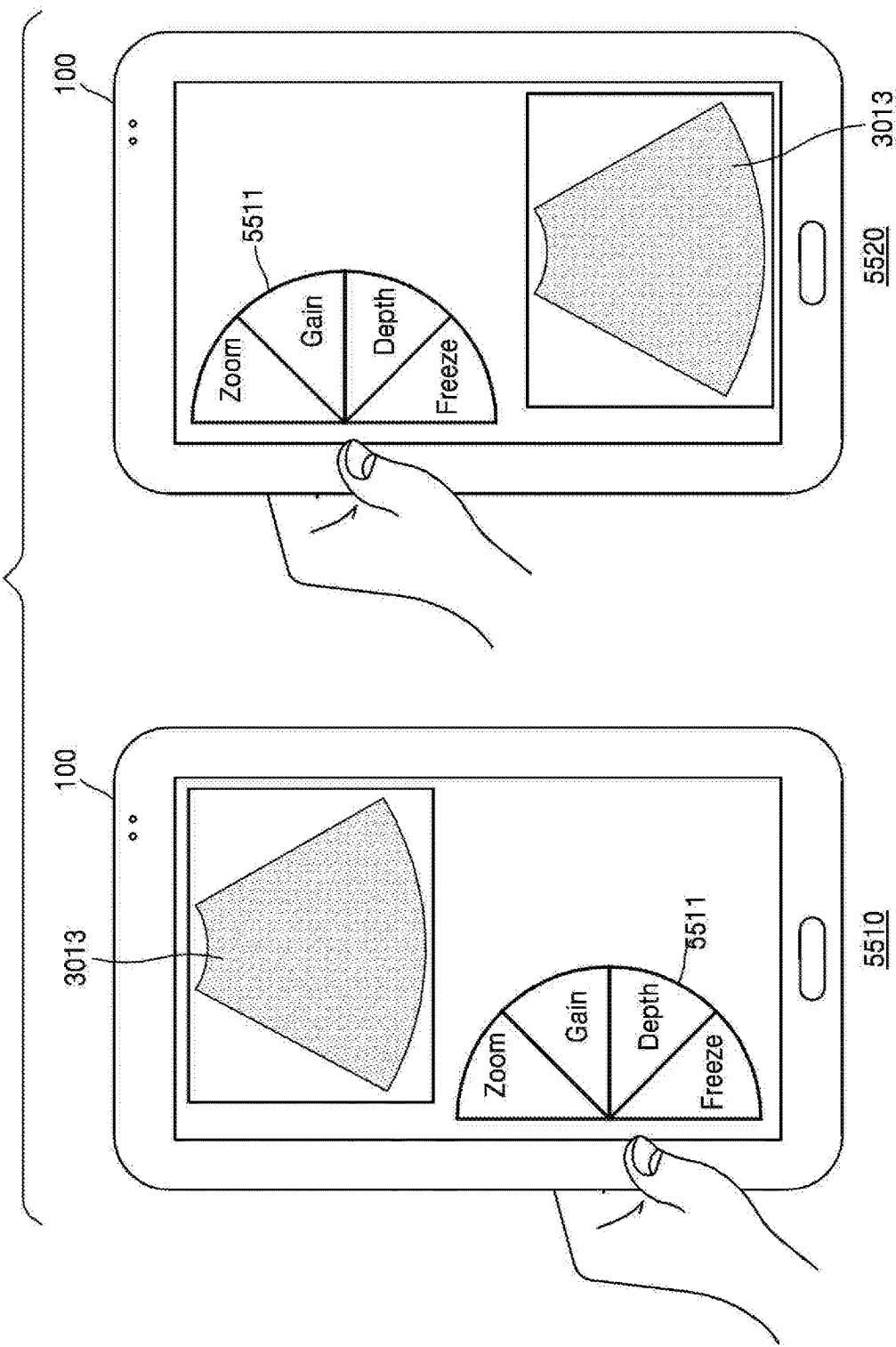
FIG. 55 illustrates an example where a medical image display apparatus changes a position where a medical image is displayed based on a position where a UI is displayed, according to an exemplary embodiment.

Referring to FIG. 55, as shown in a portion 5510, the medical image display apparatus 100 may display a medical image 3013 based on a position where a UI 5511 is displayed, so that the medical image 3013 and the UI 5511 do not overlap each other. As shown in a portion 5520, when the position where the UI 5511 is displayed changes, the medical image display apparatus 100 may change a position where the medical image 3013 is to be displayed so that the medical image 3013 and the UI 5511 do not overlap each other.

When a user holding the medical image display apparatus 100 changes, a finger-touchable range may vary accordingly.

Thus, to provide a UI suitable for each user, the medical image display apparatus 100 may provide a UI having a different size according to a size of a finger-touchable range.

Figure 56:
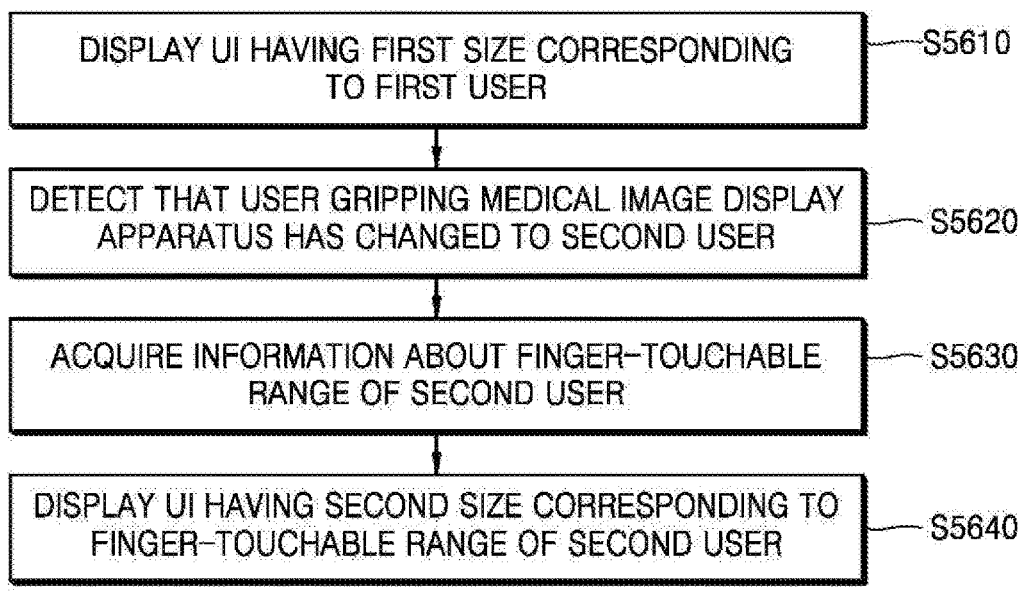
FIG. 56 is a flowchart of a method of providing, by a medical image display apparatus, UIs having sizes that vary according to users, according to an exemplary embodiment.

FIG. 56 is a flowchart of a method of providing, by the medical image display apparatus 100, UIs having sizes that differ according to users, according to an exemplary embodiment;

The medical image display apparatus 100 may display a UI having a first size corresponding to a first user (S5610).

The medical image display apparatus 100 may acquire information about a touch range of a finger of the first user from a memory included therein, a memory of an external device, or an external server. In some exemplary embodiments, the medical image display apparatus 100 may acquire the information about the touch range of the finger of the first user by analyzing a touch gesture received from the first user in response to a guide image. In addition, the medical image display apparatus 100 may receive the information about the touch range of the finger of the first user directly from the first user.

The medical image display apparatus 100 may display the UI having the first size corresponding to the touch range of the finger of the first user based on the information about the touch range. For example, the medical image display apparatus 100 may display a UI having a size that is less than or equal to the touch range of the finger of the first user.

The medical image display apparatus 100 may detect that a user gripping the medical image display apparatus 100 has changed from the first user to a second user (S5620).

For example, the medical image display apparatus 100 may detect whether a position of a user's hand used to grip the medical image display apparatus 100 has changed by using a sensing unit provided in the medical image display apparatus 100.

If the position of the user's hand used to grip the medical image display apparatus 100 has changed, the medical image display apparatus 100 may determine that the user holding the medical image display apparatus 100 has changed. If the user holding the medical image display apparatus 100 has changed, the medical image display apparatus 100 may display a GUI for receiving ID information of a new user.

The medical image display apparatus 100 may acquire information about a touch range of a finger of the second user (S5630).

The medical image display apparatus 100 may acquire the information about the touch range of the finger of the second user from a memory included therein, a memory of an external device, or an external server. In some exemplary embodiments, the medical image display apparatus 100 may acquire the information about the touch range of the finger of the second user by analyzing a touch gesture received from the second user in response to a guide image. In addition, the medical image display apparatus 100 may receive the information about the touch range of the finger of the second user directly from the second user.

The medical image display apparatus 100 may display a UI having a second size corresponding to the touch range of the finger of the second user (S5640).

Based on the touch range of the finger of the second user, the medical image display apparatus 100 may display the UI having the second size corresponding to the touch range. For example, the medical image display apparatus 100 may display a UI having a size that is less than or equal to the touch range of the finger of the second user.

Figure 57:
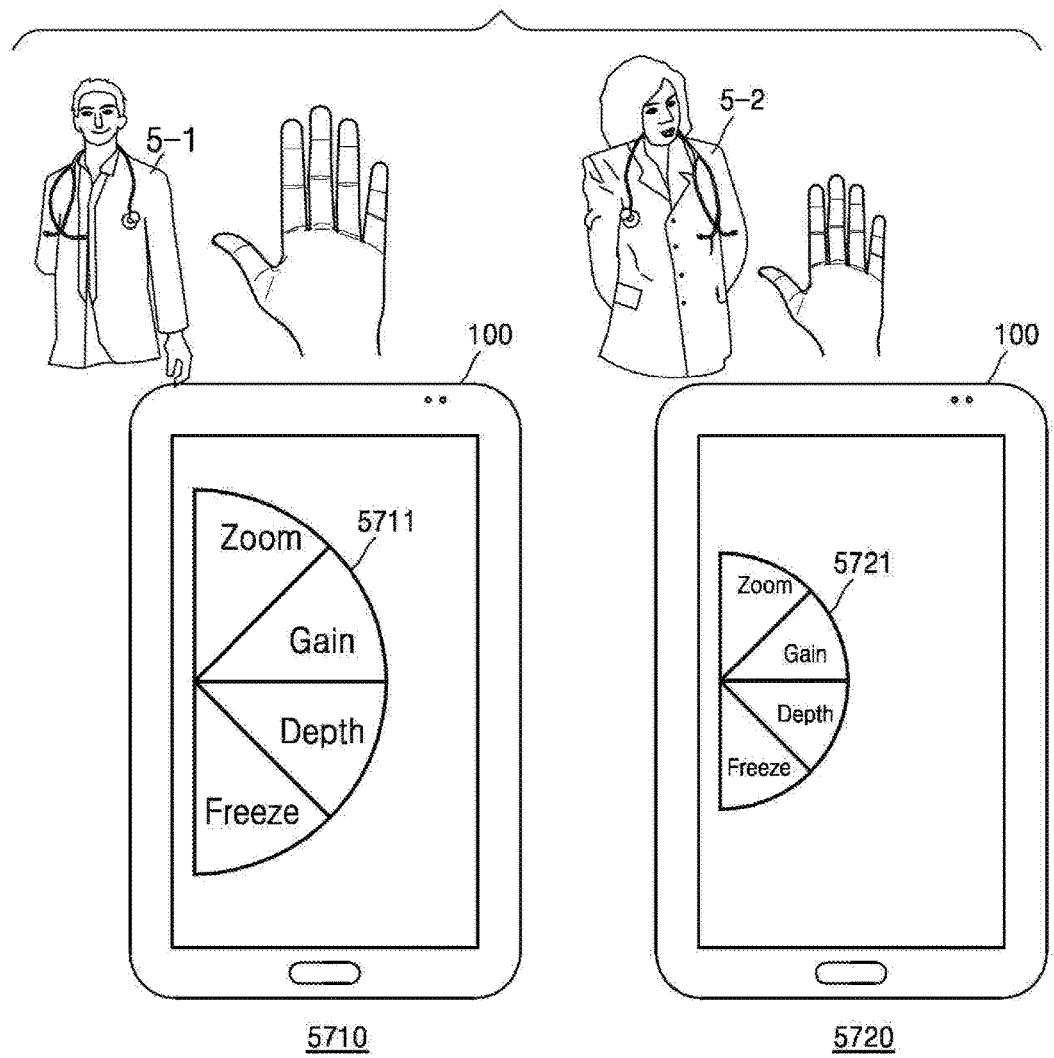
FIG. 57 illustrates examples of UIs having sizes that vary according to users, according to an exemplary embodiment.

FIG. 57 illustrates examples of UIs 5711 and 5721 having varying sizes corresponding to users according to an exemplary embodiment.

As shown in FIG. 57, different users 5-1 and 5-2 may have hands of varying sizes. For example, user 5-1 may have a hand that can be represented by hand 5710, and user 5-2 may have a hand that can be represented by hand 5720, which can be smaller than hand 5710. Thus, when a user holding the medical image display apparatus 100 changes from the user 5-1 to the user 5-2, a touch range of a finger of the user 5-1 may be changed accordingly. The medical image display apparatus 100 may provide a UI having a different size according to a finger-touchable range.

As shown in a portion 5710 of FIG. 57, the medical image display apparatus 100 may display the UI 5711 having a size corresponding to the user 5-1. As shown in a portion 5720, when the user holding the medical image display apparatus 100 changes from the user 5-1 to the user 5-2, the medical image display apparatus 100 may display the UI 5721 having a size corresponding to a touch range of a finger of the user 5-2.

As a user holding the medical image display apparatus 100, a strength of a finger touching the touch screen 110, or a posture of a finger touching the touch screen 110 changes, a contact area of a finger with the touch screen 110 when the finger touches the touch screen 110 may vary accordingly.

Thus, the medical image display apparatus 100 may display a UI based on a contact area of a user's finger.

Figure 58:
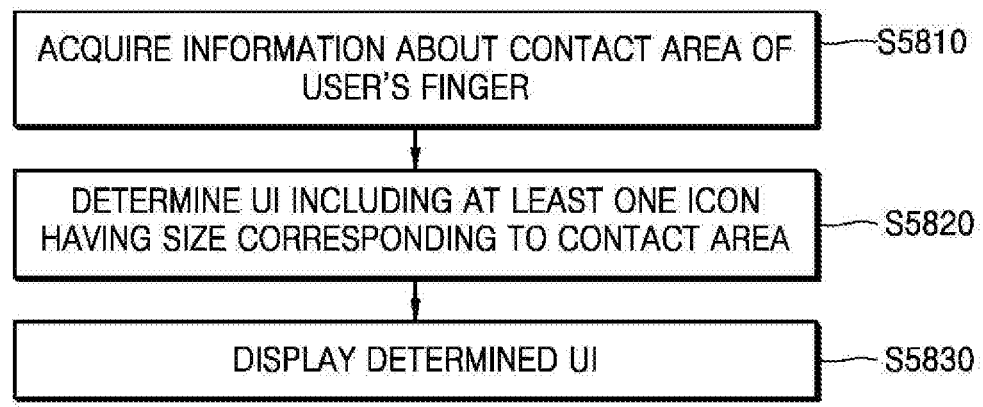
FIG. 58 is a flowchart of a method of providing a UI including an icon having a size corresponding to a contact area of a user's finger, according to an exemplary embodiment.

FIG. 58 is a flowchart of a method of providing a UI including an icon having a size corresponding to a contact area of a user's finger, according to an exemplary embodiment.

Referring to FIG. 58, the medical image display apparatus 100 may acquire information about a contact area of a user's finger (S5810).

The information about the contact area of user's finger may include information about a minimum area of user's finger with the touch screen 110 when the user's finger touches the touch screen 110. In some exemplary embodiments, the information about the contact area of user's finger may include information about an average contact area of user's finger with the touch screen 110 when the user's finger touches the touch screen 110.

Furthermore, as a thickness of a finger increases, a contact area of the finger with the touch screen 110 may increase. Furthermore, as a strength of a finger touching the touch screen 110 increases, a contact area of finger with the touch screen 110 may increase. As a finger touching the touch screen 110 becomes more perpendicular to the touch screen 110, a contact area of a finger with the touch screen 110 may decrease.

Thus, the medical image display apparatus 100 may acquire information about at least one of a thickness of a finger, a strength of a finger touching the touch screen 110, and a posture of a finger touching the touch screen 110 as information about a contact area of a user's finger.

The medical image display apparatus 110 may acquire the information about a contact area of a finger from a memory included therein, a memory of an external device, or an external server. In some exemplary embodiments, the medical image display apparatus 100 may acquire the information about the contact area of the finger by analyzing a touch gesture received from the user in response to a guide image. For example, the medical image display apparatus 100 may acquire information about the contact area of the finger by analyzing a tap touch received from the user. In addition, the medical image display apparatus 100 may receive the information about the contact area of the finger directly from the user.

When a user holding the medical image display apparatus 100 changes to a new user, the medical image display apparatus 100 may acquire information about a contact area of a user's finger again and provide a UI suitable for the new user. In some exemplary embodiments, when a position of a user's hand used to grip the medical image display apparatus 100 is changed, the medical image display apparatus 100 may acquire information about a contact area of a user's finger again and provide a UI suitable for the changed position of the user's hand.

The medical image display apparatus 100 may determine a UI including at least one icon having a size corresponding to the contact area of the user's finger (S5820).

For example, the medical image display apparatus 100 may determine a size of an icon corresponding to the contact area of the user's finger. The medical image display apparatus 100 may determine the number of icons to be included a UI based on the contact area of the user's finger. The medical image display apparatus 100 may determine a UI including a number of icons corresponding to the contact area of the user's finger.

For example, as illustrated in FIG. 5, the medical image display apparatus 100 may select a UI having a size corresponding to a finger-touchable range from among a plurality of UIs related to a medical image. The medical image display apparatus 100 may determine the number of icons to be included in the selected UI, based on a contact area of a user's finger.

If more icons are included in the UI according to the contact area of the user's finger the UI may provide a larger number of functions. As the contact area of the user's finger decreases, the medical image display apparatus may determine a UI that provides a larger number of functions.

As another example, the medical image display apparatus 100 may select from among a plurality of UIs related to a medical image a UI including at least one icon having a size corresponding to a contact area of a user's finger.

The plurality of UIs related to a medical image includes at least one of a GUI for setting parameters related to the medical image, a GUI for controlling an external device or server connected to the medical image display apparatus 100, and a UI for displaying information about the medical image.

The medical image display apparatus 100 may select a UI including an icon having a size corresponding to a contact area of a user's finger based on a result of comparing the contact area of the user's finger to a threshold value. The threshold value may be predetermined as a default value or may be set by the user. For example, if the contact area of the user's finger is greater than the threshold value, the medical image display apparatus 100 may select a UI including an icon having a first size that is greater than the threshold value. In some exemplary embodiments, if the contact area of the user's finger is less than or equal to the threshold value, the medical image display apparatus 100 may select a UI including an icon having a second size corresponding to the threshold value.

In some exemplary embodiments, the medical image display apparatus 100 may determine a UI including at least one icon having a size corresponding to the contact area of the user's finger, so that a difference between the contact area of the user's finger and a size of the icon falls within a certain range.

For example, as the contact area of the user's finger increases, the medical image display apparatus 100 may select a UI including an icon having a larger size. As the contact area of the user's finger decreases, the medical image display apparatus 100 may select a UI including an icon having a smaller size.

The medical image display apparatus 100 may display the determined UI determined in operation S5820 previously (S5830). The medical image display apparatus 100 may display the determined UI at a position determined based on a position of a user's hand or finger.

To allow a medical image provided via the medical image display apparatus 100 to be used for diagnosis or treatment of a disease, the medical image has to be provided to the user without being distorted. For example, if a UI is displayed to overlap a medical image, accuracy of diagnosis and treatment of a disease may be degraded. Thus, the medical image display apparatus 100 may change a position where the medical image is to be displayed so that a selected UI and the medical image does not overlap each other, based on a position where the selected UI is displayed.

Figure 59:
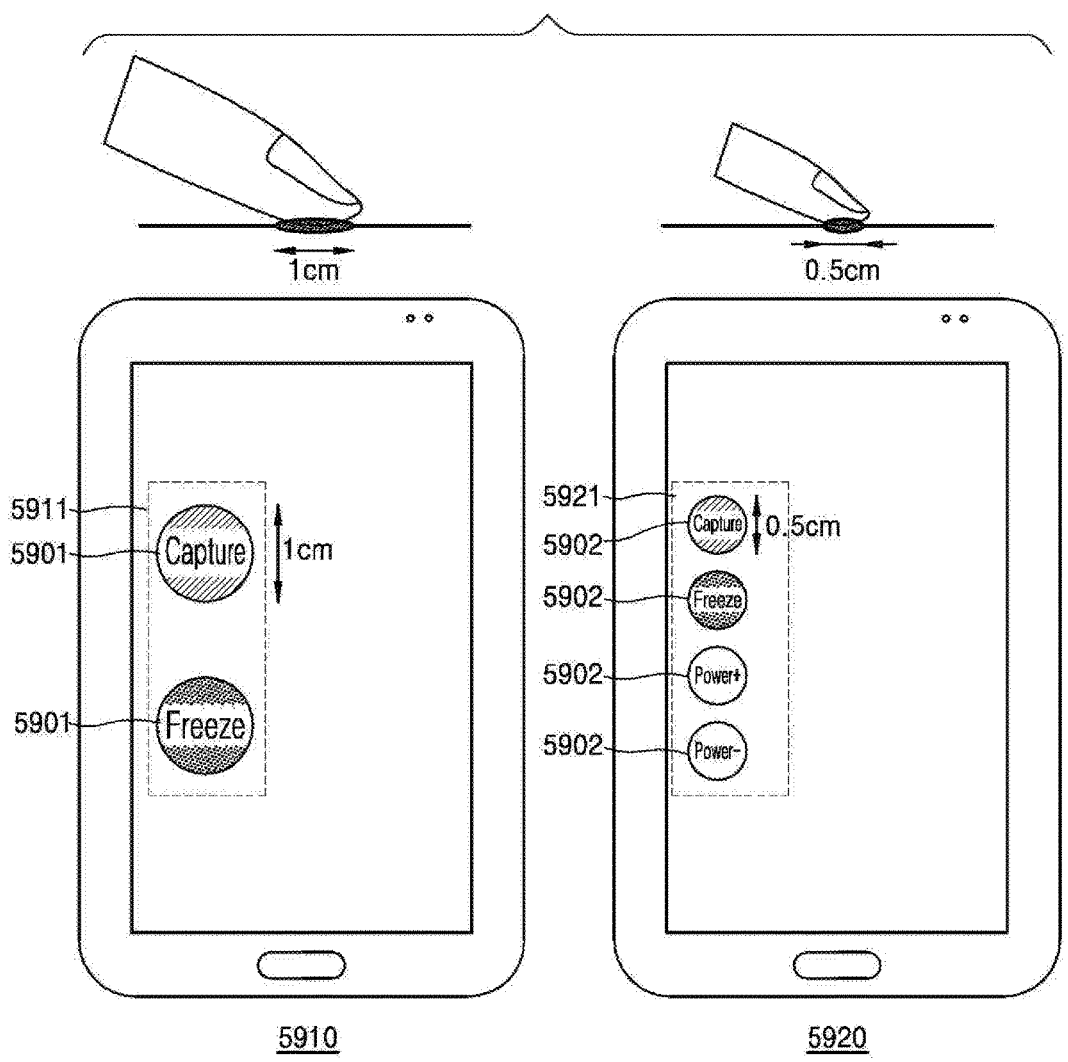
FIG. 59 illustrates examples of UIs, each including an icon having a size corresponding to a contact area of a user's finger, according to an exemplary embodiment.

FIG. 59 illustrates examples of UIs 5911 and 5921, each including an icon having a size corresponding to a contact area of a user's finger, according to an exemplary embodiment.

Referring to FIG. 59, the medical image display apparatus 100 may select the UIs 5911 and 5921 from among a plurality of UIs based on a size of a first region corresponding to a finger-touchable range and display the selected UIs 5911 and 5921.

As shown in a portion 5910, when a contact area of a user's finger corresponds to a circle having a diameter of 1 cm, the medical image display apparatus 100 may determine two icons 5901 each having the same or similar size as the contact area of the user's finger. The medical image display apparatus 100 may also determine the UI 5911 configured to include the two icons 5901 based on the size of the first region and the size of the icons 5901. As shown in the portion 5910, the medical image display apparatus 100 may display on the touch screen 110 the UI 5911 including the two icons 5901, each having a size corresponding to the contact area of the user's finger. The UI 5911 may provide a function of setting an operating mode to a live mode or a freeze mode.

As shown in a portion 5920, when a contact area of a user's finger corresponds to a circle having a diameter of 0.5 cm, the medical image display apparatus 100 may determine four icons 5902 each having the same size as the contact area of the user's finger. The medical image display apparatus 100 may also determine the UI 5921 configured to include the four icons 5902 based on the sizes of the first region and the icons 5902. As shown in the portion 5920, the medical image display apparatus 100 may display on the touch screen 110 the UI 5921 including the four icons 5902, each having a size corresponding to the contact area of the user's finger.

The UI 5921 may provide a function of setting an operating mode to a live mode or a freeze mode and a function of adjusting intensity of an ultrasound signal.

As seen in the portions 5910 and 5920, as the contact area of the user's finger decreases, the medical image display apparatus 100 may display a UI configured to provide more functions.

It has been described above that the medical image display apparatus 100 is connected to the ultrasound diagnosis device 11 or the ultrasound probe 12 and provides a UI related to an ultrasound image. However, exemplary embodiments are not limited thereto, and the medical image display apparatus 100 may provide a UI related to various types of images other than the ultrasound image. Examples of a medical image provided by the medical image display apparatus 100 may include an ultrasound image, an MR image, a CT image, a PET image, and any other type of image representing cross-section and volume data of body tissue, which may be used for diagnosis and treatment of a disease.

Figure 60:
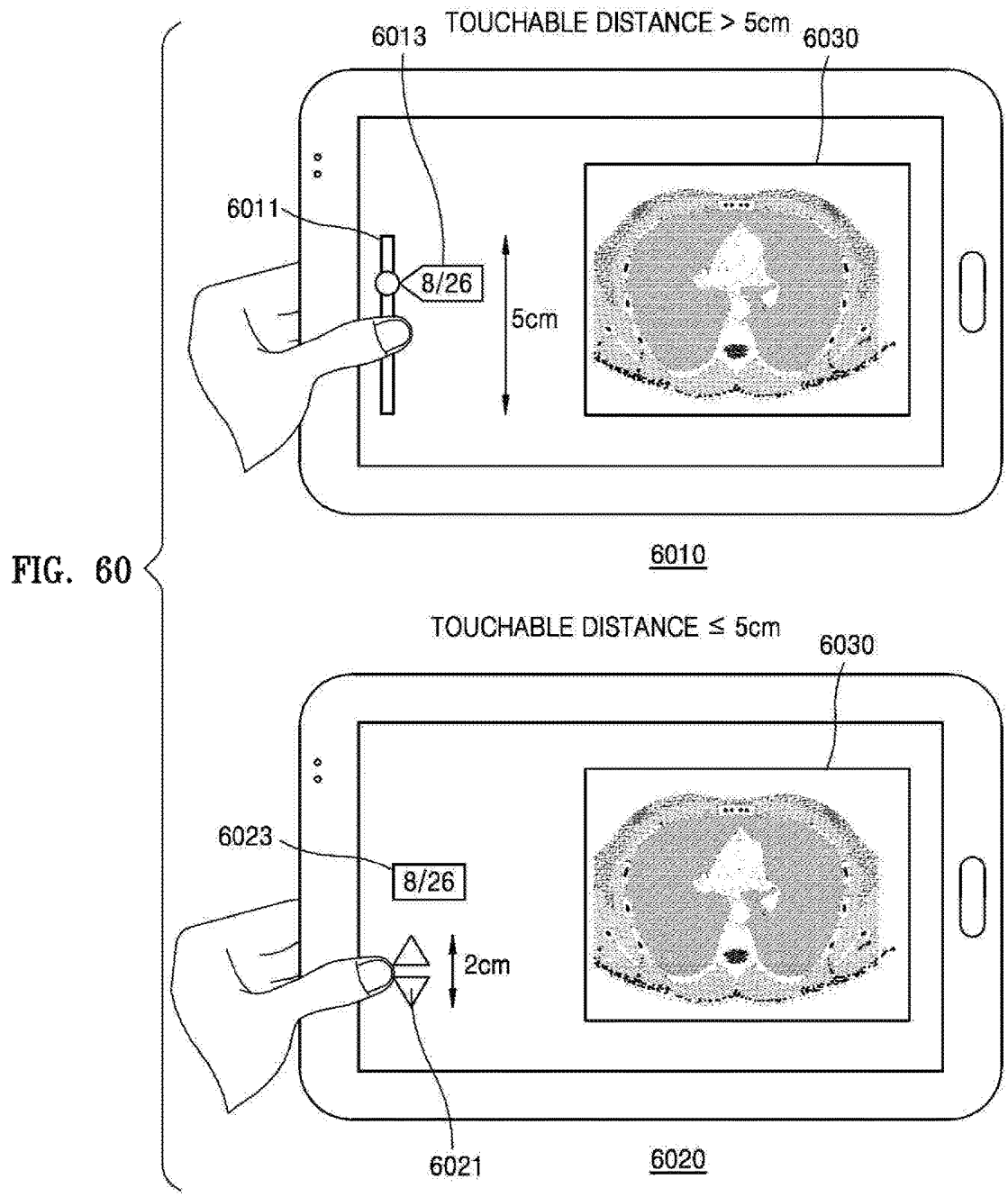
FIG. 60 illustrates examples of UIs related to a CT image displayed by a medical image display apparatus, according to an exemplary embodiment.

FIG. 60 illustrates examples of UIs 6011 and 6021 related to a CT image 6030 displayed by the medical image display apparatus 100, according to an exemplary embodiment.

Referring to FIG. 60, the medical image display apparatus 100 may provide a CT image 6030 and the UIs 6011 and 6021 related to the CT image 6030. Furthermore, the medical image display apparatus 100 may acquire a maximum finger-touchable distance as information about the first region. In other words, the medical image display apparatus 100 may acquire the maximum finger-touchable distance as a value indicative of a size of the first region.

As shown in FIG. 60, the medical image display apparatus 100 may provide the UIs 6011 and 6021 for selecting which one of a plurality of cross-sections of a chest is depicted in a CT image.

As shown in a portion 6010, the medical image display apparatus 100 may compare a maximum finger-touchable distance to a threshold value of 5 cm. When the maximum finger-touchable distance is greater than 5 cm, the medical image display apparatus 100 may select a UI 6011 from among a plurality of UIs 6011 and 6021. When the UI 6011 is selected, the medical image display apparatus 100 may display the selected UI 6011 on the touch screen 110 of FIG. 3.

The UI 6011 may, for example, be in a form of a slide bar providing a function of selecting a cross-section from among a plurality of cross-sections. As shown in the portion 6010, the medical image display apparatus 100 may display together with the UI 6011 a display window 6023 indicating a total number of cross-sections of an object and a number representing the order of a selected cross-section.

The user may select a cross-section to be examined from among the plurality of cross-sections by moving a button of the UI 6011 along a bar. As seen in the portion 6010, the medical image display apparatus 100 may display for example the CT image 6030 of an eighth cross-section among twenty-six (26) cross-sections of the chest, based on a user's touch gesture involving moving the button of the UI 6011. The medical image display apparatus 100 may display on the display window 6013 information indicating that the whole number of cross-sections is 26 and the eighth cross-section is being displayed.

As shown in a portion 6020, when the maximum finger-touchable distance is less than or equal to 5 cm, the medical image display apparatus 100 may select the UI 6021 from among the plurality of UIs 6011 and 6021. When the UI 6021 is selected, the medical image display apparatus 100 may display the selected UI 6021 on the touch screen 110.

The UI 6021 may be in a form of a button providing a function of selecting a cross-section from among a plurality of cross-sections. As shown in the portion 6020, the medical image display apparatus 100 may display together with the UI 6021 a display window 6023 indicating a total number of cross-sections of an object and a number representing the order of a selected cross-section.

The user may select a cross-section to be examined from among the plurality of cross-sections by touching a triangular button of the UI 6021. For example, by touching an upward-pointing triangle button included in the UI 6021, the user may select a cross-section with a higher order number than that of a cross-section currently being displayed. By touching a downward-pointing triangle button included in the UI 6021, the user may select a cross-section with a number lower than that of a cross-section currently being displayed.

As shown in the portion 6020, the medical image display apparatus 100 may display, for example, the CT image 6030 of an eighth cross-section among twenty-six (26) cross-sections of the chest, based on a user's touch gesture involving touching the button of the UI 6021. The medical image display apparatus 100 may display on the display window 6023 information indicating that the whole number of cross-sections is 26 and the eighth cross-section is being displayed.

As shown in FIGS. 48A and 48B, the medical image display apparatus 100 may select UIs of different sizes based on the size of the first region. Furthermore, as shown in FIG. 60, the medical image display apparatus 100 may select UIs configured to receive different types of touch gestures based on the size of the first region.

Figure 61:
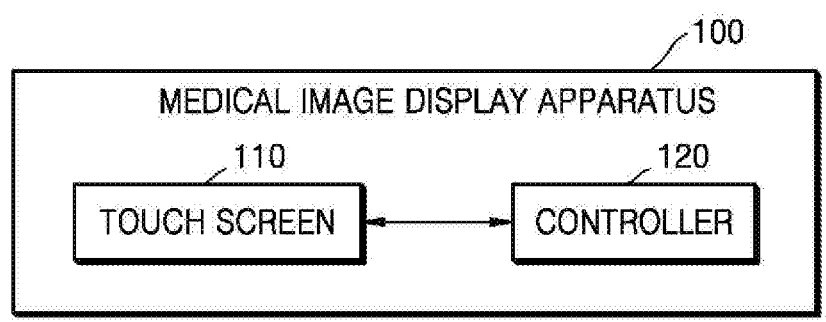
FIG. 61 and FIG. 62 are block diagrams of a medical image display apparatus according to exemplary embodiments.
Figure 62:
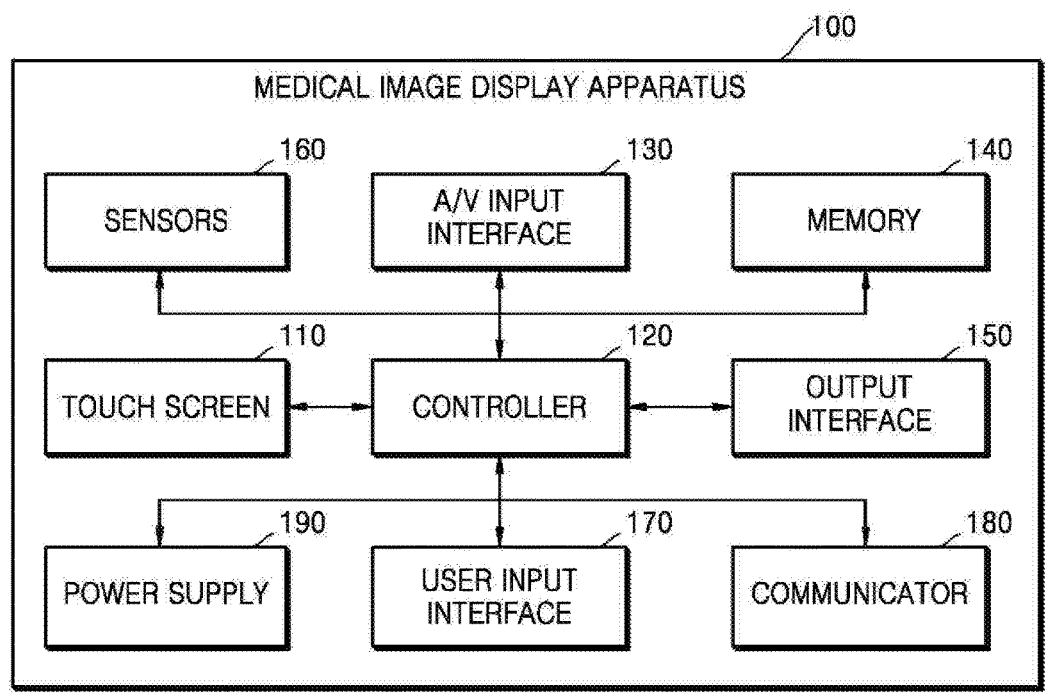

FIGS. 61 and 62 are block diagrams of medical image display apparatuses 100 according to exemplary embodiments.

Because operations of the methods of FIGS. 5, 45, 49, 53, 56, and 58 are performed by components of the medical image display apparatus 100 of FIGS. 61 and 62, the same descriptions as provided above with respect to FIGS. 5, 45, 49, 53, 56, and 58 will be omitted below.

Referring to FIG. 61, the medical image display apparatus 100 according to an exemplary embodiment may include a touch screen 110 and a controller 120.

The touch screen 110 may receive a touch input for controlling the medical image display apparatus 100 from a user and display information being processed by the medical image display apparatus 100. For example, the touch screen 110 may display a medical image or a UI related to the medical image.

The touch screen 110 may be a screen in which a display forms a layer structure with a touch pad.

To display information being processed by the medical image display apparatus 100, the touch screen 110 may include at least one of a liquid crystal display (LCD), a thin-film transistor (TFT)-LCD, an organic light-emitting diode (OLED) display, a flexible display, a 3D display, and an electrophoretic display The touch screen 110 may include various sensors configured to sense a touch or proximity touch input from the user. For example, the touch screen 110 may include a tactile sensor configured to sense a touch from the user. The tactile sensor may detect various pieces of information including the roughness of a contact surface, the hardness of an object to be touched, and the temperature of a point to be touched. Furthermore, to detect a proximity touch of a user, the touch screen 110 may include a proximity sensor. Examples of the proximity sensor may include a fiber-optic proximity sensor, a high-frequency oscillation-type proximity sensor, a capacitive proximity sensor, an electromagnetic proximity sensor, and an infrared proximity sensor.

The touch screen 110 may sense a tap touch, a touch and hold gesture, a double tap touch, a drag touch, a panning touch, a flick touch, a swipe touch, etc. input by the user.

The controller 120 may control overall operations of the medical image display apparatus 100. For example, the controller 120 may control the touch screen 110. Referring to FIG. 62, when the medical image display apparatus 100 includes more components than those shown in FIG. 61, the controller 120 may further control at least one of an audio/video (A/V) input interface 130, a memory 140, an output interface 150, sensors 160, a user input interface 170, a communicator 180, and a power supply 190.

The controller 120 may acquire information about a first region related to a finger-touchable range on the touch screen 110. For example, the controller 120 may acquire information about the first region for defining a touch range on the touch screen 110 that may be touched by a finger of a user's hand used to grip the medical image display apparatus 100.

The controller 120 may acquire the information about the first region from a memory included in the medical image display apparatus 100, a memory of an external device, or an external server. In some exemplary embodiments, the controller 120 may acquire the information about the first region by analyzing a touch gesture received from the user in response to a guide image. In addition, the controller 120 may receive the information about the first region directly from the user.

The controller 120 may select a UI corresponding to a size of the first region from among a plurality of UIs related to a medical image. The controller 120 may control the touch screen 110 to display the selected UI.

The controller 120 may select a corresponding number of functions to the size of the first region from among all functions provided by the medical image display apparatus 100 in relation to a medical image. The controller 120 may select a UI including at least one icon corresponding to the selected functions from among a plurality of UIs.

The controller 120 may select a touch gesture corresponding to the size of the first region from among different types of touch gestures. The controller 120 may select a UI configured to receive the selected touch gesture from among a plurality of UIs.

The controller 120 may select one of a plurality of UIs based on at least one of a direction in which the medical image display apparatus 100 displays content and a side of the medical image display apparatus 100 where a user's hand used to grip the medical image display apparatus 100 is located. The controller 120 may control the touch screen 110 to display the selected UI.

A medical image display apparatus 100 according to other exemplary embodiments may include more components than those shown in FIG. 61. For example, as shown in FIG. 62, the medical image display apparatus 100 may further include at least one of the A/V input interface 130, the memory 140, the output interface 150, the sensors 160, the user input interface 170, the communicator 180, and the power supply 190.

The A/V input interface 130 is a unit for inputting an audio or video signal and may include a camera, a microphone, etc. The camera may obtain image frames such as still images or moving images via an image sensor. Images captured via the image sensor may be processed via the controller 120 or a separate image processor (not shown).

Image frames processed by the camera may be stored in the memory 140 or transmitted to the outside via the communicator 180.

The microphone may receive an external audio signal and convert the received external audio signal into electrical audio data. For example, the microphone may receive an audio signal from an external device or a speaking person. The microphone may use various denoising algorithms for removing noise generated during reception of an external audio signal.

The memory 140 may store programs necessary for processing or control operations performed by the controller 120 or store data input to or output from the medical image display apparatus 100. For example, the memory 140 may store a medical image being displayed via the medical image display apparatus 100.

The memory 140 may include at least one storage medium from among a flash memory-type memory, a hard disk-type memory, a multimedia card micro-type memory, card-type memories (e.g., an SD card, an XD memory, and the like), random access memory (RAM), static random access memory (SRAM), read-only memory (ROM), electrically erasable programmable ROM (EEPROM), PROM, magnetic memory, a magnetic disc, and an optical disc.

The programs stored in the memory 140 may, for example, be classified into a plurality of modules according to their functions. For example, the programs may be classified into a UI module, a touch screen module, a notification module, etc.

The UI module may provide a UI, a GUI, etc. suitable according to user. The touch screen module may detect a user's touch gesture with respect to the touch screen 110 and transmit information about the detected touch gesture to the controller 120. The notification module may generate a signal for notifying occurrence of an event in the medical image display apparatus 100. The notification module may output a notification signal in a form of a video signal via the touch screen 110 or in a form of an audio or vibration signal via the output interface 150.

The memory 140 may store information about the first region for defining a finger-touchable range. The memory 140 may map the information about the first region corresponding to each user to ID information of the user for storage. Furthermore, the memory 140 may store a plurality of UIs related to a medical image.

The output interface 150 may output information being processed by the medical image display apparatus 100. For example, the output interface 150 may output an audio signal, a video signal, a light signal, or a vibration signal. The output interface 150 may include a separate display other than the touch screen 110 to output a video signal.

The output interface 150 may output an audio signal received from the communicator 180 or stored in the memory 140. The output interface 150 may also output audio signals associated with functions of the medical image display apparatus 100 (e.g., a message reception sound and a notification sound). The output interface 150 may include a speaker, a buzzer, etc. to output an audio signal.

Furthermore, the output interface 150 may output a vibration signal. For example, the output interface 150 may output a vibration signal corresponding to an output of an audio or video signal. Furthermore, the output interface 150 may output a vibration signal when a touch is input via the touch screen 110.

The sensors 160 may detect a status of the medical image display apparatus 100 or a status of an environment around the medical image display apparatus 100 and transmit information about the detected status to the controller 120.

For example, the sensors 160 may acquire information about whether the medical image display apparatus 100 has been detached from a medical image acquisition apparatus. The sensors 160 may detect motion information of the medical image display apparatus 100. The sensors may also detect whether a position of a user's hand used to grip the medical image display apparatus 100 has changed.

The sensors 160 may include at least one of a magnetic sensor, an acceleration sensor, a temperature/humidity sensor, an infrared sensor, a gyroscope sensor, a position sensor (e.g., global positioning system (GPS)), a barometric pressure sensor, a proximity sensor, an optical sensor, a depth sensor, and an ultrasound sensor, but is not limited thereto. Because functions of the above-descried sensors may be inferred intuitively by those of ordinary skill in the art, detailed descriptions thereof will be omitted below.

The user input interface 170 is a unit by which the user may input data necessary for controlling the medical image display apparatus 100. Examples of the user input interface 170 may include, but are not limited to, a keypad, a dome switch, a button, a wheel, a trackball, a touch pad, a jog wheel, and a jog switch.

The user input interface 170 may receive at least one of a user input for setting parameters related to a medical image, a user input for controlling operations of the medical image display apparatus 100, a user input for controlling an external device or server connected to the medical image display apparatus 100, and a user input for inputting information about the medical image.

The communicator 180 may include one or more components that enable communication between the medical image display apparatus 100 and a medical image acquisition apparatus or server. For example, the communicator 180 may include a short-range wireless communicator, a mobile communicator, and a broadcast receiving unit.

The short-range wireless communicator may include a Bluetooth communication module, a Bluetooth Low Energy (BLE) communication module, a short-range wireless communication module (Near Field Communication (NFC)/Radio Frequency Identification (RFID) module), a wireless local area network (WLAN) communication module, a Zigbee communication module, an Infrared Data Association (IrDA) communication module, a Wi-Fi Direct (WFD) communication module, and an Ultra Wideband (UWB) communication module, but is not limited thereto.

The mobile communicator transmits or receives a wireless signal to or from at least one of a base station, an external terminal, and a server in a mobile communication network. In this case, the wireless signal may be a voice call signal, a video call signal, or data in any one of various formats according to transmission and reception of a text/multimedia message.

The broadcast receiver may receive a broadcast signal and broadcast-related information from the outside via a broadcast channel. The broadcast channel may include a satellite channel, a terrestrial channel, etc. According to an exemplary embodiment, the medical image display apparatus 100 may not include the broadcast receiving unit.

The communicator 180 may receive medical image data from a medical image acquisition apparatus for acquiring medical image data from an object, such as the ultrasound diagnosis device (11 of FIG. 1), the ultrasound probe (12 of FIG. 1), or the medical image acquisition device (13 of FIG. 1) configured to acquire medical image data other than ultrasound image data. Furthermore, the communicator 180 may transmit a control signal to the medical image acquisition apparatus.

The communicator 180 may receive medical image data from, for example, the server 14 of FIG. 1. The communicator 180 may transmit or receive data to or from a hospital server connected through a picture archiving and communication system (PACS), and perform data communication with the server 14 according to the digital imaging and communications in medicine (DICOM) standard.

The power supply 190 supplies power necessary for operations of the medical image display apparatus 100 to components. The power supply 190 may include a rechargeable battery or a cable or cable port for receiving power from the outside.

Figure 63:
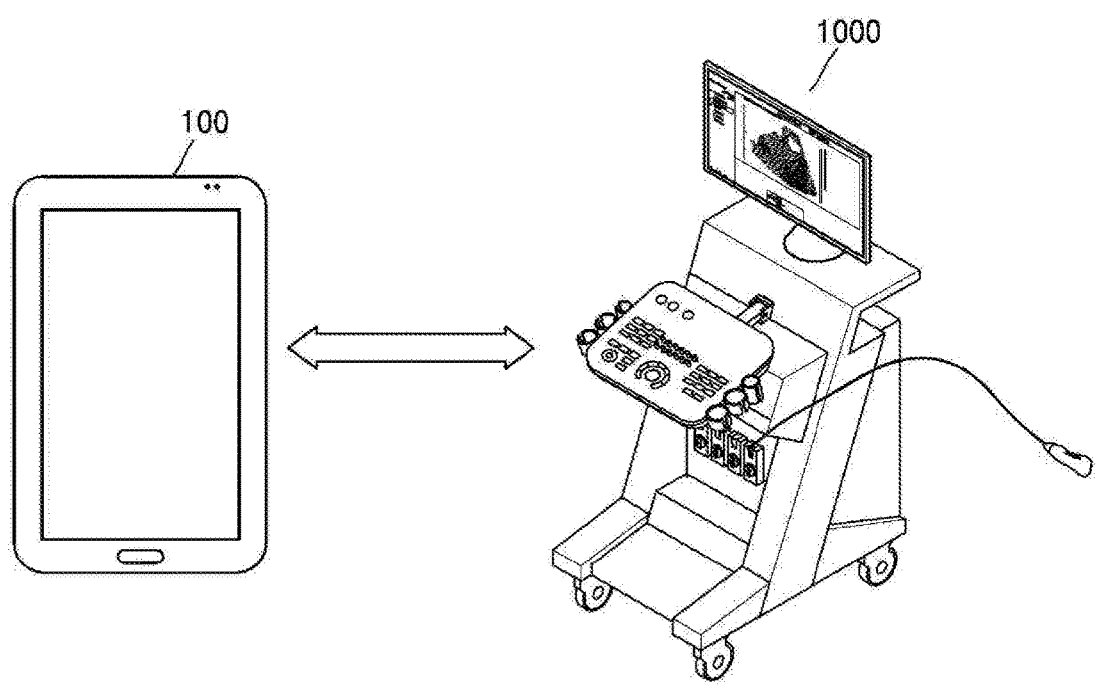
FIG. 63 illustrates a medical image display apparatus that is connectable to an ultrasound diagnosis apparatus according to an exemplary embodiment.

In addition, referring to FIG. 63, the medical image display apparatus 100 may be connected to an ultrasound diagnosis apparatus 1000 by wire or wirelessly.

The medical image display apparatus 100 may be included in the ultrasound diagnosis apparatus 1000 and attached to or detached from the ultrasound diagnosis apparatus 1000. In some exemplary embodiments, the medical image display apparatus 100 may be a separate device that is connected to the ultrasound diagnosis apparatus 1000 by wire or wirelessly and receives ultrasound image data from the ultrasound diagnosis apparatus 1000.

The medical image display apparatus 100 may display an ultrasound image based on ultrasound image data received from the ultrasound diagnosis apparatus 1000. The medical image display apparatus 100 may control the touch screen 110 and provide a UI for setting various functions related to an operation of displaying an ultrasound image. Furthermore, the medical image display apparatus 100 may control the ultrasound diagnosis apparatus 1000 and provide a UI for setting various functions related to an operation of acquiring ultrasound image data performed by the ultrasound diagnosis apparatus 1000.

Figure 64:
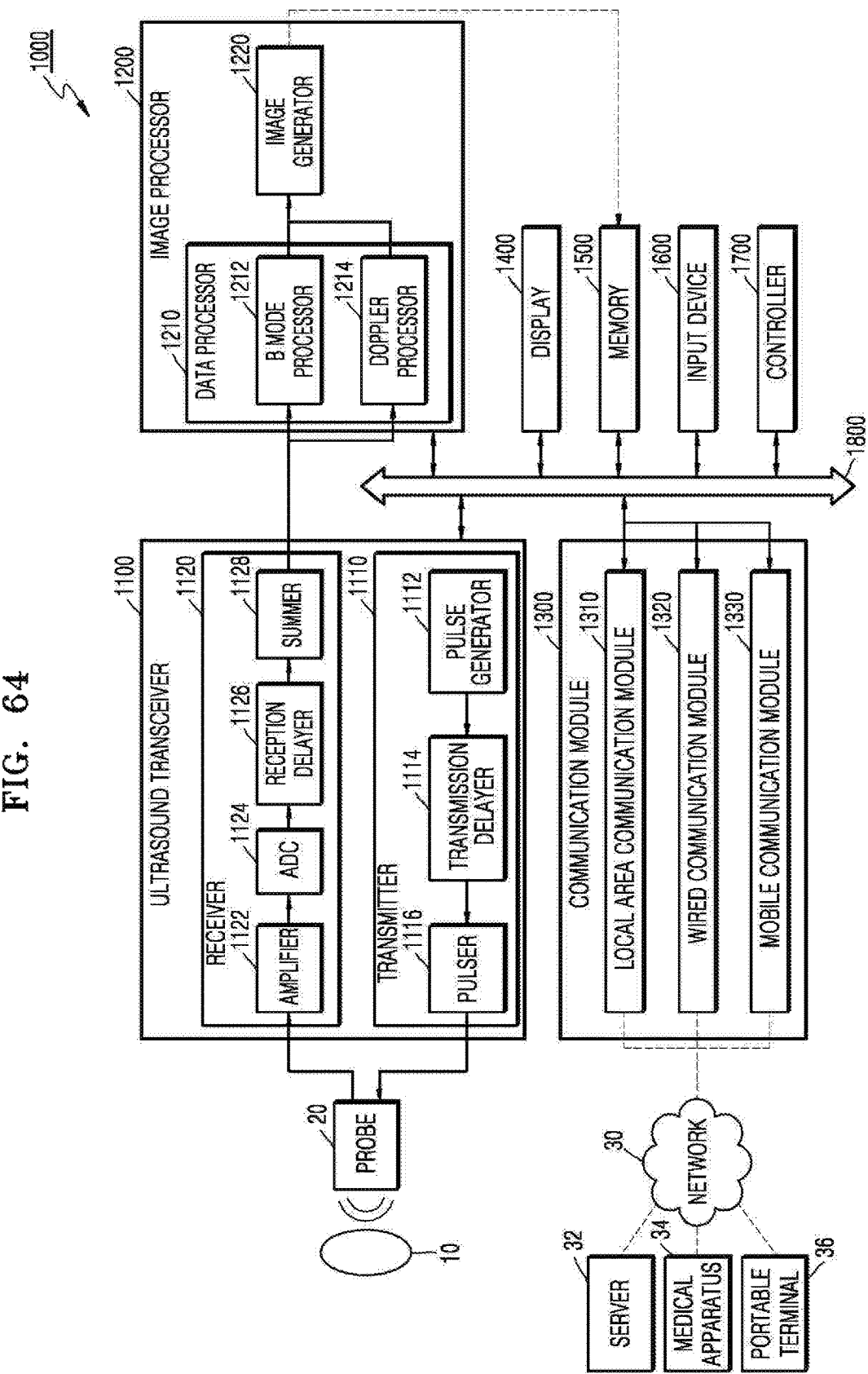
FIG. 64 is a block diagram of an ultrasound diagnosis apparatus that is connectable to a medical image display apparatus, according to an exemplary embodiment.

FIG. 64 is a block diagram of an example of an ultrasound diagnosis apparatus 1000 that is connectable to the medical image display apparatus 100, according to an exemplary embodiment.

FIG. 64 is a block diagram of a configuration of the ultrasound diagnosis apparatus 1000 according to an exemplary embodiment. Referring to FIG. 64, the ultrasound diagnosis apparatus 1000 may include a probe 20, an ultrasound transceiver 1100, an image processor 1200, a communication module 1300, a display 1400, a memory 1500, an input device 1600, and a controller 1700, which may be connected to one another via buses 1800.

The ultrasound diagnosis apparatus 1000 may be a cart type apparatus or a portable type apparatus. Examples of portable ultrasound diagnosis apparatuses may include, but are not limited to, a picture archiving and communication system (PACS) viewer, a smartphone, a laptop computer, a personal digital assistant (PDA), and a tablet PC.

The probe 20 may transmit ultrasound waves to an object 10 in response to a driving signal applied by the ultrasound transceiver 1100 and may receive echo signals reflected by the object 10. The probe 20 includes a plurality of transducers, and the plurality of transducers oscillate in response to electric signals and generate acoustic energy, that is, ultrasound waves. Furthermore, the probe 20 may be connected to the main body of the ultrasound diagnosis apparatus 1000 by wire or wirelessly, and according to exemplary embodiments, the ultrasound diagnosis apparatus 1000 may include a plurality of probes 20.

A transmitter 1110 may supply a driving signal to the probe 20. The transmitter 110 may include a pulse generator 1112, a transmission delayer 1114, and a pulser 1116. The pulse generator 1112 may generate pulses for forming transmission ultrasound waves based on a predetermined pulse repetition frequency (PRF), and the transmission delayer 1114 may delay the pulses by delay times necessary for determining transmission directionality. The pulses which have been delayed correspond to a plurality of piezoelectric vibrators included in the probe 20, respectively. The pulser 1116 may apply a driving signal (or a driving pulse) to the probe 20 based on timing corresponding to each of the pulses which have been delayed.

A receiver 1120 may generate ultrasound data by processing echo signals received from the probe 20. The receiver 120 may include an amplifier 1122, an analog-to-digital converter (ADC) 1124, a reception delayer 1126, and a summer 1128. The amplifier 1122 may amplify echo signals in each channel, and the ADC 1124 may perform analog-to-digital conversion with respect to the amplified echo signals. The reception delayer 1126 may delay digital echo signals output by the ADC 1124 by delay times necessary for determining reception directionality, and the summer 1128 may generate ultrasound data by summing the echo signals processed by the reception delayer 1166. In some exemplary embodiments, the receiver 1120 may not include the amplifier 1122. In other words, if the sensitivity of the probe 20 or the capability of the ADC 1124 to process bits is enhanced, the amplifier 1122 may be omitted.

The image processor 1200 may generate an ultrasound image by scan-converting ultrasound data generated by the ultrasound transceiver 1100. The ultrasound image may be not only a grayscale ultrasound image obtained by scanning an object in an amplitude (A) mode, a brightness (B) mode, and a motion (M) mode, but also a Doppler image showing a movement of an object via a Doppler effect. The Doppler image may be a blood flow Doppler image showing flow of blood (also referred to as a color Doppler image), a tissue Doppler image showing a movement of tissue, or a spectral Doppler image showing a moving speed of an object as a waveform.

A B mode processor 1212 may extract B mode components from ultrasound data and process the B mode components. An image generator 1220 may generate an ultrasound image indicating signal intensities as brightness based on the extracted B mode components 1212.

Similarly, a Doppler processor 1214 may extract Doppler components from ultrasound data, and the image generator 1220 may generate a Doppler image indicating a movement of an object as colors or waveforms based on the extracted Doppler components.

According to an exemplary embodiment, the image generator 1220 may generate a three-dimensional (3D) ultrasound image via volume-rendering with respect to volume data and may also generate an elasticity image by imaging deformation of the object 10 due to pressure. Furthermore, the image generator 1220 may display various pieces of additional information in an ultrasound image by using text and graphics. In addition, the generated ultrasound image may be stored in the memory 1500.

A display 1400 may display the generated ultrasound image. The display 1400 may display not only an ultrasound image, but also various pieces of information processed by the ultrasound diagnosis apparatus 1000 on a screen image via a graphical user interface (GUI). In addition, the ultrasound diagnosis apparatus 1000 may include two or more displays 1400 according to exemplary embodiments.

The communication module 1300 may be connected to a network 30 by wire or wirelessly to communicate with an external device or a server. The communication module 1300 may exchange data with a hospital server or another medical apparatus in a hospital, which is connected thereto via a PACS. Furthermore, the communication module 1300 may perform data communication according to the digital imaging and communications in medicine (DICOM) standard.

The communication module 1300 may transmit or receive data related to diagnosis of an object, e.g., an ultrasound image, ultrasound data, and Doppler data of the object, via the network 30 and may also transmit or receive medical images captured by another medical apparatus, e.g., a computed tomography (CT) apparatus, a magnetic resonance imaging (MRI) apparatus, or an X-ray apparatus. Furthermore, the communication module 1300 may receive information about a diagnosis history or medical treatment schedule of a patient from a server and utilizes the received information to diagnose the patient. Furthermore, the communication module 1300 may perform data communication not only with a server or a medical apparatus in a hospital, but also with a portable terminal of a medical doctor or patient.

The communication module 1300 may be connected to the network 30 by wire or wirelessly to exchange data with a server 32, a medical apparatus 34, or a portable terminal 36. The communication module 1300 may include one or more components for communication with external devices. For example, the communication module 1300 may include a local area communication module 1310, a wired communication module 1320, and a mobile communication module 1330.

The local area communication module 1310 refers to a module for local area communication within a predetermined distance. Examples of local area communication techniques according to an exemplary embodiment may include, but are not limited to, wireless LAN, Wi-Fi, Bluetooth, ZigBee, Wi-Fi Direct (WFD), ultra wideband (UWB), infrared data association (IrDA), Bluetooth low energy (BLE), and near field communication (NFC).

The wired communication module 1320 may refer to a module for communication using electric signals or optical signals. Examples of wired communication techniques according to an exemplary embodiment may include communication via a twisted pair cable, a coaxial cable, an optical fiber cable, and an Ethernet cable.

The mobile communication module 1330 may transmit or receive wireless signals to or from at least one selected from a base station, an external terminal, and a server on a mobile communication network. The wireless signals may be voice call signals, video call signals, or various types of data for transmission and reception of text/multimedia messages.

The memory 1500 may store various data processed by the ultrasound diagnosis apparatus 1000. For example, the memory 1500 may store medical data related to diagnosis of an object, such as ultrasound data and an ultrasound image that are input or output, and may also store algorithms or programs which are to be executed in the ultrasound diagnosis apparatus 1000.

The memory 1500 may be any of various storage media, e.g., a flash memory, a hard disk drive, EEPROM, etc. Furthermore, the ultrasound diagnosis apparatus 1000 may utilize web storage or a cloud server that performs the storage function of the memory 1500 online.

The input device 1600 may refer to a means via which a user inputs data for controlling the ultrasound diagnosis apparatus 1000. The input device 1600 may include hardware components, such as a keypad, a mouse, a touch pad, a touch screen, and a jog switch. However, embodiments are not limited thereto, and the input device 1600 may further include any of various other input units including an electrocardiogram (ECG) measuring module, a respiration measuring module, a voice recognition sensor, a gesture recognition sensor, a fingerprint recognition sensor, an iris recognition sensor, a depth sensor, a distance sensor, etc.

The controller 1700 may control all operations of the ultrasound diagnosis apparatus 1000. In other words, the controller 1700 may control operations among the probe 20, the ultrasound transceiver 1100, the image processor 1200, the communication module 1300, the display 1400, the memory 1500, and the input device 1600 shown in FIG. 64.

In some exemplary embodiments, all or some of the probe 20, the ultrasound transceiver 1100, the image processor 1200, the communication module 1300, the display 1400, the memory 1500, the input device 1600, and the controller 1700 may be implemented as software modules. Also, at least one of the ultrasound transmission/reception unit 1100, the image processor 1200, and the communication module 1300 may be included in the controller 1700; however, the exemplary embodiments are not limited thereto.

When the medical image display apparatus 100 according to an exemplary embodiment is included in the ultrasound diagnosis apparatus 1000, the medical image display apparatus 100 may perform some or all of the functions of at least one of the image processor 1200, the communication module 1300, the display 1400, the input device 1600, and the controller 1700.

In some exemplary embodiments, the medical image display apparatus 100 may be a separate device that is connected to the ultrasound diagnosis apparatus 1000 by wire or wirelessly and receives ultrasound image data from the ultrasound diagnosis apparatus 1000. In this case, the medical image display apparatus 100 may display at least some of ultrasound images displayed and output by the display 1400 of the ultrasound diagnosis apparatus 1000 and GUIs displaying various pieces of information being processed by the ultrasound diagnosis apparatus 1000.

Exemplary embodiments may be implemented through computer-readable recording media having recorded thereon computer-executable instructions such as program modules that are executed by a computer. Computer-readable media may be any available media that can be accessed by a computer and include both volatile and nonvolatile media and both detachable and non-detachable media. Furthermore, the computer-readable media may include computer storage unit media and communication media. The computer storage unit media include both volatile and nonvolatile and both detachable and non-detachable media implemented by any method or technique for storing information such as computer-readable instructions, data structures, program modules, or other data. The communication media typically embody computer-readable instructions, data structures, program modules, other data of a modulated data signal, or other transmission mechanism, and they include any information transmission media.

The above description is provided for illustration, and it will be understood by those of ordinary skill in the art that various changes in form and details may be made therein without departing from essential features and the spirit and scope of the exemplary embodiments as defined by the following claims. Accordingly, the above exemplary embodiments and all aspects thereof are examples only and are not limiting. For example, each component defined as an integrated component may be implemented in a distributed fashion. Likewise, components defined as separate components may be implemented in an integrated manner.

The scope is defined not by the detailed description thereof but by the appended claims, and all the changes or modifications within the scope of the appended claims and their equivalents will be construed as being included therein.

What is claimed is:

1. A medical image display apparatus comprising: a touch screen configured to display a medical image and receive an input from a user; a sensor configured to detect attachment and detachment of the medical image display apparatus; and a controller configured to: monitor whether the medical image display apparatus is connected to a medical image acquisition apparatus by the sensor, in response to detecting, by the sensor, detachment of the medical image display apparatus from the medical image acquisition apparatus, acquire information indicating a touch input range of the user, configure a user interface for controlling operations associated with acquiring the medical image such that the user interface corresponds to the indicated touch input range, and control the touch screen to display the user interface.

2. The medical image display apparatus of claim 1, further comprising:
a communication unit operatively coupled to a hand-held ultrasound probe,
wherein the user interface includes selectable icons associated with functions executable to alter at least one ultrasound emission of the hand-held ultrasound probe.

3. The medical image display apparatus of claim 2, wherein the medical image acquisition apparatus includes an ultrasound diagnosis device, the hand-held ultrasound probe is wiredly connected to the ultrasound diagnosis device, and
wherein the communication unit is operatively coupled to the hand-held ultrasound probe through the ultrasound diagnosis device.

4. The medical image display apparatus of claim 3, wherein the controller is further configured to:
in response to detecting a first touch input selecting an icon on the user interface, change the user interface to display a second user interface for adjusting a parameter corresponding to the selected icon,
in response to detecting a second touch input including at least one of a drag, a panning, and swipe touches in the second user interface, adjust the parameter according to movement of the drag.

5. The medical image display apparatus of claim 4, wherein a different parameter is selected for adjustment based on a type of touch input of the first touch input, and
wherein the type of touch input includes one or more of a touch-and-hold and a double-tap.

6. The medical image display apparatus of claim 1, wherein the touch input range of the user indicates an available range of motion of a particular finger of a user's hand relative to the touch screen, when the medical image display apparatus is held one-handed in the user's hand.

7. The medical image display apparatus of claim 6, wherein the user interface is configured further based on a location along a surface of the medical image display apparatus at which the medical image display apparatus is held in the user's hand.

8. The medical image display apparatus of claim 1, wherein acquiring the information indicating the touch input range further comprises: receiving identification information corresponding to the user; and retrieving a particular touch input range previously associated with the received identification information, wherein the received identification information includes at least one of a user name, a biometric marker, and a predetermined input pattern.

9. The medical image display apparatus of claim 8, wherein the controller is further configured to:
in response to detecting, by the sensor, that a position of a user's hand has changed relative to the touch screen, re-acquire the information indicating a touch input range of the user.

10. The medical image display apparatus of claim 1, wherein acquiring the information indicating the touch input range further comprises:
displaying on the touch screen at least one guide image;
detecting a touch input selecting and moving the at least one guide image; and
generating the touch input range by analyzing a range of movement indicated by the touch input selecting and moving the at least one guide image.

11. A method for medical image display in an electronic device, comprising: monitoring whether the electronic device is connected to a medical image acquisition apparatus by a sensor, in response to detecting, by the sensor, detachment of the electronic device from the medical image acquisition apparatus, acquire information indicating a touch input range of a user, configuring, by a processor, a user interface for controlling operations associated with acquiring the medical image, such that the user interface corresponds to the indicated touch input range, and displaying the configured user interface on a touch screen.

12. The method of claim 11, wherein the electronic device includes a communication unit operatively coupled to a hand-held ultrasound probe, the method further comprising:
displaying, as the user interface, selectable icons associated with functions executable to alter at least one ultrasound emission of the hand-held ultrasound probe.

13. The method of claim 12, wherein the medical image acquisition apparatus includes an ultrasound diagnosis device, and the hand-held ultrasound probe is wiredly connected to the ultrasound diagnosis device, the method further comprising:
establishing communication with the hand-held ultrasound probe through the ultrasound diagnosis device.

14. The method of claim 13, further comprising:
in response to detecting a first touch input selecting an icon on the user interface, changing the user interface to display a second user interface for adjusting a parameter corresponding to the selected icon,
in response to detecting a second touch input including at least one of a drag, a panning, and swipe touches in the second user interface, adjusting the parameter according to movement of the drag.

15. The method of claim 14, wherein a different parameter is selected for adjustment based on a type of touch input of the first touch input, and
wherein the type of touch input includes one or more of a touch-and-hold and a double-tap.

16. The method of claim 11, wherein the touch input range of the user indicates an available range of motion of a particular finger of a user's hand relative to the touch screen, when the electronic device is held one-handed in the user's hand.

17. The method of claim 11, wherein acquiring the information indicating the touch input range further comprises: receiving identification information corresponding to the user; and retrieving a particular touch input range previously associated with the received identification information, wherein the received identification information includes at least one of a user name, a biometric marker, and a predetermined input pattern.

18. The method of claim 17, further comprising:
in response to detecting, by the sensor, that a position of a user's hand has changed relative to the touch screen, re-acquiring the information indicating a touch input range of the user.

19. The method of claim 11, wherein acquiring the information indicating the touch input range further comprises:
displaying on the touch screen at least one guide image;
detecting a touch input selecting and moving the at least one guide image; and
generating the touch input range by analyzing a range of movement indicated by the touch input selecting and moving the at least one guide image.

20. A non-transitory computer-readable recording medium having recorded thereon a program for performing the method of claim 11.

* * * * *